US007250305B2

(12) United States Patent
Cosenza et al.

(10) Patent No.: US 7,250,305 B2
(45) Date of Patent: Jul. 31, 2007

(54) USE OF DYE TO DISTINGUISH SALT AND PROTEIN CRYSTALS UNDER MICROCRYSTALLIZATION CONDITIONS

(75) Inventors: Larry Cosenza, Birmingham, AL (US); Terry L. Bray, Birmingham, AL (US); Lawrence J. DeLucas, Birmingham, AL (US); Thomas E. Gester, Birmingham, AL (US); David T. Hamrick, Glencoe, AL (US)

(73) Assignee: UAB Research Foundation, Birmingham, AL (US)

( * ) Notice: Subject to any disclaimer, the term of this patent is extended or adjusted under 35 U.S.C. 154(b) by 451 days.

(21) Appl. No.: 10/208,576

(22) Filed: Jul. 30, 2002

(65) Prior Publication Data

US 2003/0180960 A1    Sep. 25, 2003

Related U.S. Application Data

(60) Provisional application No. 60/328,958, filed on Oct. 12, 2001, provisional application No. 60/308,698, filed on Jul. 30, 2001.

(51) Int. Cl.
*G01N 33/00* (2006.01)
(52) U.S. Cl. ........................................... 436/86
(58) Field of Classification Search .................. 436/86
See application file for complete search history.

(56) References Cited

U.S. PATENT DOCUMENTS

| 4,263,010 A | 4/1981 | Randolph |
| 4,517,048 A | 5/1985 | Shlichta |
| 4,668,584 A | 5/1987 | Uzgiris et al. |
| 4,755,363 A | 7/1988 | Fujita et al. |
| 4,833,233 A | 5/1989 | Carter |
| 4,886,646 A | 12/1989 | Carter et al. |
| 4,900,147 A | 2/1990 | Bowley et al. |
| 4,909,933 A | 3/1990 | Carter et al. |
| 4,919,899 A | 4/1990 | Herrmann et al. |
| 5,009,861 A | 4/1991 | Plaas-Link |

(Continued)

FOREIGN PATENT DOCUMENTS

EP    0 553539 A1    8/1993

(Continued)

OTHER PUBLICATIONS

Izit Crystal Dye User Guide, Hampton Research (2000).*

(Continued)

*Primary Examiner*—Monique T. Cole
(74) *Attorney, Agent, or Firm*—Bingham McCutchen LLP

(57) ABSTRACT

An improved method of screening crystal growth conditions is provided wherein molecules are crystallized from solutions containing dyes. These dyes are selectively incorporated or associated with crystals of particular character thereby rendering crystals of particular character colored and improving detection of the dyed crystals. A preferred method involves use of dyes in protein solutions overlayed by oil. Use of oil allows the use of small volumes of solution and facilitates the screening of large numbers of crystallization conditions in arrays using automated devices that dispense appropriate solutions to generate crystallization trials, overlay crystallization trials with an oil, provide appropriate conditions conducive to crystallization and enhance detection of dyed (colored) or undyed (uncolored) crystals that result.

55 Claims, 5 Drawing Sheets
(5 of 5 Drawing Sheet(s) Filed in Color)

U.S. PATENT DOCUMENTS

| | | |
|---|---|---|
| 5,013,531 A | 5/1991 | Snyder et al. |
| 5,076,698 A | 12/1991 | Smith et al. |
| 5,078,975 A | 1/1992 | Rhodes et al. |
| 5,096,676 A | 3/1992 | McPherson et al. |
| 5,106,592 A | 4/1992 | Stapelmann et al. |
| 5,124,935 A | 6/1992 | Wallner et al. |
| 5,130,105 A | 7/1992 | Carter et al. |
| 5,193,685 A | 3/1993 | Trevithick |
| 5,221,410 A | 6/1993 | Kushner et al. |
| 5,256,241 A | 10/1993 | Noever |
| 5,400,741 A | 3/1995 | DeTitta et al. |
| 5,419,278 A | 5/1995 | Carter |
| 5,544,254 A | 8/1996 | Hartley et al. |
| 5,581,476 A | 12/1996 | Osslund |
| 5,641,681 A | 6/1997 | Carter |
| 5,643,540 A | 7/1997 | Carter et al. |
| 5,728,559 A | 3/1998 | Nilsson et al. |
| 5,790,421 A | 8/1998 | Osslund |
| 5,855,753 A | 1/1999 | Trau et al. |
| 5,869,604 A | 2/1999 | Rousseau et al. |
| 5,872,010 A | 2/1999 | Karger et al. |
| 5,873,394 A | 2/1999 | Meltzer |
| 5,961,934 A | 10/1999 | Arnowitz et al. |
| 5,973,779 A | 10/1999 | Ansari et al. |
| 5,985,356 A | 11/1999 | Schultz et al. |
| 5,997,636 A | 12/1999 | Gamarnik et al. |
| 6,031,082 A | 2/2000 | Nielsson et al. |
| 6,036,920 A | 3/2000 | Pantoliano et al. |
| 6,039,804 A | 3/2000 | Kim et al. |
| 6,057,159 A | 5/2000 | Lepre |
| 6,069,934 A | 5/2000 | Verman et al. |
| 6,268,158 B1 | 7/2001 | Pantoliano et al. |
| 6,296,673 B1 | 10/2001 | Santarsiero et al. |
| 6,297,021 B1 | 10/2001 | Nienaber et al. |
| 6,303,322 B1 | 10/2001 | Pantoliano et al. |
| 6,402,837 B1 | 6/2002 | Shtrahman et al. |
| 6,404,849 B1 | 6/2002 | Olson et al. |
| 6,406,903 B2 | 6/2002 | Bray et al. |
| 6,409,832 B2 | 6/2002 | Weigl et al. |
| 6,413,778 B1 | 7/2002 | Carpenter et al. |
| 6,417,007 B1 | 7/2002 | Gittleman et al. |
| 6,468,346 B2 | 10/2002 | Arnowitz et al. |
| 2001/0016191 A1 | 8/2001 | Osslund |
| 2001/0016314 A1 | 8/2001 | Anderson et al. |
| 2001/0019845 A1 | 9/2001 | Bienert et al. |
| 2001/0027745 A1 | 10/2001 | Weigl et al. |
| 2001/0032582 A1 | 10/2001 | DeTitta et al. |
| 2001/0055669 A1 | 12/2001 | Schultz et al. |
| 2001/0055775 A1 | 12/2001 | Schultz et al. |
| 2002/0022250 A1 | 2/2002 | Hendrickson et al. |
| 2002/0029814 A1 | 3/2002 | Unger et al. |
| 2002/0048610 A1 | 4/2002 | Cirna et al. |
| 2002/0054663 A1 | 5/2002 | Olson et al. |
| 2002/0062783 A1 | 5/2002 | Bray |
| 2002/0064485 A1 | 5/2002 | Delucas et al. |
| 2002/0067800 A1 | 6/2002 | Newman et al. |
| 2002/0164812 A1 | 11/2002 | DeLucas |
| 2003/0022383 A1 | 1/2003 | DeLucas |
| 2003/0022384 A1 | 1/2003 | DeLucas |
| 2003/0027348 A1 | 2/2003 | DeLucas |

FOREIGN PATENT DOCUMENTS

| | | |
|---|---|---|
| JP | 02001013054 A | 1/2001 |
| WO | WO 00/60345 A1 | 10/2000 |
| WO | WO 01/26797 A2 | 4/2001 |
| WO | WO 01/92293 A2 | 12/2001 |

OTHER PUBLICATIONS

LoVerde, Marilena, "Crystallization of GABAA Receptor" Energy Research Undergraduate Fellowship, UC Berkley, pp. 1-10, Aug. 18, 2000.*

"Meeting Summaries," printed from http://www-nmr.cabm.rutgers.edu/labdocuments/mtgsummaries/mtgsummaries.html on Apr. 12, 2002 (32 pages).

"Minutes May 1-2, 2001—Biological and Environmental Research Advisory Committee (BERAC)," printed from http://www.er.doe.gov/production/ober/berac/5-01mins.html on Apr. 12, 2002 (10 pages).

"NIGMS—Advisory Council Meeting Minutes, May 1998—Minutes of the National Advisory General Medical Sciences Council—May 14-15, 1998," printed from http://www.nigms.nih.gov/about_nigms/council_may98.html on Apr. 12, 2002 (10 pages) (site last updated Jul. 17, 1998).

"NIGMS—NIGMS Structural Genomics Targets Workshop Feb. 11-12, 1999" printed from http://www.nigms.nih.gov/news/meetings/structural_genomics_targets.html on Apr. 12, 2002 (18 pages).

"NIGMS Protein Structure Initiative Meeting Summary Apr. 24, 1998," printed from http://www.nigms.nih.gov/news/reports/protein_structure.html on Apr. 12, 2002 (12 pages) (site last updated Jun. 2, 1998).

"RAMC 1999—Round Table Notes," particularly regarding Robotics (starting at bottom of 1st page), printed from www.hamptonresearch.com/stuff.RAMC99RTN.html.om Aug. 21, 2002 (7 pages).

Abbott, A. "Structures by numbers," Nature 408:130-132 (Nov. 9, 2000).

Abola et al., "Automation of X-ray crystallography," Nat. Struc. Biol. (Structural Genomics Supplement:973-977 (Nov. 2000)Mochalkin et al., "High-Throughput Structure Determination in an Informatics Environment," (2001) print from http://www.accelrys.com webzine on Aug. 1, 2002 (4 pages).

Adersen, G.R. et al., "A Spreadsheet Approach to Automated Protein Crystallization," J. Appl. Cryst. 29:236-240 (1996).

Advertisement: "The first Fully Automated Digital Imaging System specifically for crystollographers—CrystalScore. Cyber Lab," ACA Newsletter 1:28 (Spring, 2000).

Baird, J.K., "Theory of protein crystal nucleation and growth controlled by solvent evaporation," J. Cryst, Growth 204:553-562 (1999).

Baldock, P., et al., "A comparison of microbatch and vapour diffusion for initial sceening of crystallization conditions," J. Cryst. Growth 168:170-174 (1996).

Beckmann, W., et al., "The Effect of Additives on Nucleation: A Low Cost Automated Apparatus," J. Crystal Growth 99:1061-1064 (1990).

Berry, M.B., "Protein Crystallization: Theory and Practice," excerpts from "Structure and Dynamics of E. coli Adenylate Kinase," by Michael B. Berry (Sep. 17, 1995), 12 pages, printed from http://www.bioc.nce.edu/~berry/crystallization/crystallization.

Blow, D.M., et al., "Control of nucleation of protein crystals," Protein Sci. 3:1638-1643 (1994).

Brandt, D.W., "Multiplexed nanoliter transfers for high throughput drug screening using the Biomek 2000 and the high density replicating tool," J. Biomol. Screen 2:111-116 (1997).

Brochure: Automation Protein Crystallization System. Douglas Instruments Limited. (1990)(4 pages).

Brodersen, D.E., et al., "Computer Programs—XAcr : a program for construction, automated setup and bookkeeping of crystallization experiments," J. Appl. Cryst. 32:1012-1016 (1999).

Bullock, E., et al., "Apparatus for the growth of crystals from small volumes of solution," J. Physics E: Sci. Instrum. 5:412-413 (1972).

Burley, S. K., et al., "Structural genomics: beyond the Human Genome Project," Nat. Genet. 23:151-157 (1999).

Carter, C.W., "Efficient Factorial Designs and the Analysis of Macromolecular Crystal Growth Conditions," *Methods: A Comparison to Meth. Enzymol.* 1(1):12-24 (1990).

Casay, G.A., et al., "Laser scattering in a hanging drop vapor diffusion apparatus for protein crystal growth in a microgravity environment," *J. Crystal Growth* 122:95-101 (1992).

Catalog, 63 pp., Hampton Research Corporation (copyright 1999).

Chayen, N.E., et al., "An Automated System for Micro-Batch Protein Crystallization and Screening," *J. Appl. Cryst.* 23:.297-302 (1990).

Chayen, N.E., et al., "Apocrustacyanin A1 from the lobster carotenoprotein a-crustacyanin: crystallization and initial X-ray analysis involving softer X-rays," *Acta Cryst.* D56:1064-1066 (Aug. 2000).

Chayen, N.E., et al., "Control of nucleation in the crystallization of lysozyme," *Protein Sci.* 2:113-118 (1993).

Chayen, N.E., et al., "Fish muscle structure: fibre types in flatfish and mullet fin muscles using histochemistry and antimyosin antibody labeling," J. Muscle Res. Cell Motility 14:53-542 (Oct. 1993).

Chayen, N.E., et al., "Microbatch crystallization under oil—a new technique allowing many small-volume crystallization trials," *J. Crystal Growth* 122:176-180 (1992).

Chayen, N.E., et al., "Porous Silicon: an Effective Nucleation-inducing Material for Protein Crystallization," *J. Mol. Biol.* 312:591-595 (2001).

Chayen, N.E., et al., "Protein crystallization for genomics: towards high-throughput optimization techniques," *Acta Cryst.* D58:921-927 (2002).

Chayen, N.E., et al., "Purification, crystallization and initial X-ray analysis of the $C_1$ subunit of the astaxanthin protein, $V_{600}$, of the chondrophore *Velella velella*," *Acta Cryst.* D55:266-268 (1999).

Chayen, N.E., et al., "Space-grown crystals may prove their worth," *Nature* 398(6722):20 (1999).

Chayen, N.E., et al., "Trends and Challenges in Experimental Macromolecular Crystallography," *Quart. Rev. Biophysics* 29(3):227-278 (Aug. 1996).

Chayen, N.E., "A novel technique to control the rate of vapour diffusion, giving larger protein crystals," *J. Appl. Crsyt.* 30:198-202 (1997).

Chayen, N.E., "Comparative studies of Protein Crystallization by Vapour-Diffusion and Microbatch Techniques," *Acta Cryst.* D54:8-15 (1998).

Chayen, N.E., "Protocol: A novel technique for containerless protein crystallization," *Protein Enginnering* 9(10):927-929 (1990).

Chayen, N.E., "Tackling the bottleneck of protein crystallization in the post-genomic era," *Trends Biotech.* 20(3):98 (2002).

Chayen, N.E., "The role of oil in macromolecular crystallization," *Structure* 5(10):1269-1274 (1997).

Chayen, N.E., et al., "New developments of the IMPAX small-volume automated crystallization system," Acta Cryst. D50:456-458 (1994).

Cianci, M., et al., "Structure of lobster apocrustacyanin $A_1$ using softer X-rays," *Acta Cryst.* D57:1219-1229 (Apr. 2001).

Cox, M. J., et al., "An Investigation of Protein Crystallization Parameters using Successive Automated Grid Searches (SAGS)," *J. Cryst. Growth* 90(1-3):318-324 (1988).

Cox, M.J., et al., "Experiments with Automated Protein Crsytallization," *J. Appl. Cryst.* 20:366-373 (1987).

Cudney, B., et al., "Screening and Optimization Strategies for Macromolecular Crystal Growth," *Acta Cryst.* D50:414-423 (1994).

D'Arcy, A., "Crystallization Proteins—a Rational Approach?," *Acta Cryst.* D50:469-471 (1994).

DeLucas, et al., "New High-throughput Crystallization Technology," (Abstract E0014 from ACA2002 Meeting), printed from http://www.hwi.buffalo.edu/ACA on Apr. 10, 2002 (1 page).

Diller, D.J., et al., "An accurate numerical model for calculating the equilibration rate of a hanging-drop experiment," *Acta Cryst.* D55-656-663 (1999).

Dong, J., et al., "Bound-solvent structures for microgravity-, ground control-, gel- and microbatch-grown hen egg-white lysozyme crystals at 1.8 A resolution," *Acta Cryst.* D55:745-752 (Apr. 1999).

Ducruix, A., & Giege, R. (Eds.) "Crsytallization of Nucleic acids and protein. A practical approach," (Second Edition) Oxford: Oxford University Press (1999).

Elchoff, et al., "Development of a technology for automation and miniaturization of protein crystallization," *J Biotech* 85(1):7-14 (2001).

Evans, P.R., et al., "Crystallographic Structure of Allosterically Inhibited Phosphofructokinase at 7A Resolution," *J. Mol. Biol.* 191:713-720 (1986).

Fiehn, H., et al., "Microsystem Technology for Pipetting Systems: Parallel Sample Treatment in the Submicroliter Range (25)," *smallTalk2000 Association for Laboratory Automation Final Conference Program*, San Diego, CA, held Jul. 8-12, 2000 (Abstract) (1 page).

Gaasterland, T., "Feasibility of Structured Genomics and Impact on Computational Biology: Post-Workshop Review," Mathematics and Computer Science Division, Argonne National Laboratory, Jan. 26, 1998 printed from http://www-fp.mcs.anl.gov/ ~gaasterland/sg-review. html on Apr. 12, 2002 (7 pages).

Gaasterland, T., "Structural genomics: Bioinformatics in the driver's seat," *Nat. Biotech.* 16:625-627 (Jul. 1998).

Gilliland, G. L., et al., "Screening For Crystallization Conditions and Robotics: Biological Macromolecule Crystallization Database, Version 3.0: New Features, Data and the NASA Archive for Protein Crystal Growth Data," *Acta Cryst.* D50:408-413 (1994).

Gonzalez, F., et al., "Crocodile: An Automated Apparatus for Organic Crystal Growth from Solution," *Acta Astronatica* 25(12):775-784 (1991).

Heinemann, et al., Scientific concepts: The Berlin "Protein Structure Factory initiative," printed from http://www.rzpd.de/psf/s_concept2.html on Dec. 21, 2001 (16 pages).

Jancarik, J., et al., "Sparse matrix sampling: a screening method for crystallization of proteins," *J. Appl. Cryst.* 24:409-411 (1991).

Jing, H., et al., "New structural motifs on the chymotrypsin fold and their potential roles in complement factor B," *EMBO J.* 19(2):164-173 (2000).

Jing, H., et al., "Structural basis of profactor D activation: from a highly flexible zymogen to a novel self-ibhibited serine protease, complement factor D," *Euro. Mol. Bio. Org*, 18(4):804-814 (1999).

Jing, H., et al., "Structures of Native and Complexed Complement Factor D: Implications of the Atypical Analytical His57 Conformation and Self-Inhibitory Loop in the Regulation of Specific Serine Protease Activity," *J. Mol. Biol.* 282:1061-1081 (1998).

Jones, et al., "Fully Automated Preparation of Hanging Drop Protein Crystallization Plates," abstract from ACA01 meeting printed from http://www.hwi.buffalo.edu/ ACA/ACA01/abstracts/text/W0352. html on Aug. 26, 2002 (1 page).

Jones, N., et al., "Apocalypse now: update on automated protein Crystallization using the new ACA vapor diffusion plate," *Acta CrystallogrA* (1987) 43 (Supplement): C275.

Kam, et al., "On the Crystallization of Proteins," *J. Mol. Biol.* 123:539-555 (1978).

Kelders, H.A., et al., "Automated protein crystallization and a new crystal form of a subtilisin: eglin complex," *Protein Engin.* 1(4):301-303 (1987).

Koltay, P., "A Novel Fixed Volume Dispenser for the Massive Parallel Liquid Handling of Nanoliter Volumes," (Abstract for presentation scheduled for Oct. 25, 2001) printed from http://www.eurolabautomation.org on Apr. 11, 2002 (2 pages).

Korkhin, Y.M., et al., "Microseeding—Crystallization of a protein by microseeding after establishing its phase diagram," in Research Report 1 (Aug. 1995), printed from http://www douglas.co.uk/rep1.html on Apr. 11, 2002 (6 pages).

Leonidas, D.D., et al., "Refined Crystal Structures of Native Human Angiogenin and Two Active Site Variants: Implications for the Unique Functional Properties of an Enzyme Involved in Neovascularization During Tumour Growth," *J. Mol. Biol.* 285:1209-1233 (1999).

Lloyd, L.F., et al., "Many Crystal Forms of Human Immunodeficiency Virus Reverse Transcriptase," *J. Mol. Biol.* 217(1):19-22 (1991).

Lowe, J., et al., "Capital Equipment MRC Laboratory of Molecular Biology Nov. 4, 2001" (4 pages).

Luft, et al., "High Throughput Protein Crystallization: Keeping up with the Genomics,"(Abstract for presentation to be given at Gordon Research Conference "Diffraction Methods in Molecular Biology" on Jul. 3, 2000 at Andover, NH, USA) printed from http://www.imca.aps.anl.gov/~ahoward/luft_ab.html (1 page).

Luft, et al., "Macromolecular crystallization in a high throughput laboratory-the search phase," *J. Cryst, Growth* 232:591-595 (2001).

Luft, et al., "Microbatch macromolecular crystallization in micropipettes," *J. Cryst. Growth* 196:450-455 (1999).

Luft, et al., "Microbatch macromolecular crystallization on a thermal gradient," *J. Cryst. Growth* 196:447-449 (1999).

Luo, M., "Structural Genomics of *C. elegans*," (Abstract W0027 from ACA2002 Meeting) printed from http://www.hwi.buffalo.edu/ACA/ACA02/abstracts/text/W0027.html on Apr. 10, 2002 (1 page).

McPherson, A., "Crystallization of Macromolecules: General Principles," in *Methods in Enzymology* 114:112-120 (1985).

McPherson, A., "Crystallization of Proteins by Variation of pH or Temperature," in *Methods in Enzymology* 114:125-127 (1985).

McPherson, A., "Two approaches to the rapid screening of crystallization conditions," *J. Cryst. Growth* 122:161-167 (1992).

McPherson, A., "Use of Polyethylene Glycol in the Crystallization of Macromolecules," in *Methods in Enzymology* 114:120-125 (1985).

Meeting Summary: "NIH Protein Structure Initiative Meeting: Target Selection, Feb. 1999, Washington, D.C." printed from http:///www-nmr.cabm.ruters.edu/labdocuments/mtgsummaries/nih_prot_struct_init/nih on Apr. 12, 2002 (23 pages).

Meeting Summary: "NIGMS Structural Genomics Project Planning Meeting—The Protein Structure Initiative, Bethesda, MD, Nov. 24, 1998," printed from http://www-nmr.cabm.rutgers.edu/labdocuments/mtgsummaries/nigms.html on Apr. 12, 2002 (17 pages).

Montelione, G.T., et al., "Structural genomics: keystone for a Human Proteome Project," *Nat. Struct. Biol.* 6(1):11-12 (Jan. 1999).

Morris, D.W., et al., "Automation of Protein Crystallization Trials: Use of a Robot to Deliver Reagents to a Novel Multi-Chamber Vapor Diffusion Plate," *Biotechniques* 7(5):522-527 (1989).

Mueller, et al., "Development of a technology for automation and miniaturization of protein crystallization," *J. Biotech.* 85(1):7-14 (2001).

Needleman and Wunsch, "A General Method Applicable to the Search for Similarities in the Amino Acid Sequence of Two Proteins." *J. Mol Biol* 48:443-453 (1970).

Newman, A.R., "Send in the Robots," *Anal. Chem.* 62(1):29A-34A (1990).

News Release: "Large-scale Xn: 'The use of Microbatch for Large Scale Crystallization Projects,'" Douglas Instruments, Hungerford, UK (indicated on website as news from Feb. 1999), printed from http://www.douglas.co.uk/proposal.html on Feb. 22, 2001 (5 pages).

Nyarsik, et al., "High Throughput Screening Station for Automated Protein Crystallization," (Abstract) (1 page).

Oct. 2, 2002 Press Release: "Minutes Apr. 22-23, 1999—Biological and Environmental Research Advisory Committee (BERAC)," this meeting was announced in the Federal Register for Apr. 22-23, 1999 (Public Law 92-463, 86 Stat. 770) American Geophysical Union, Washington, D.C., printed from http://www.er.doe.gov/production/ober/berac/4-99mins.html on Apr. 12, 2002 (8 pages).

Oldfield, T.J., et al., "A Flexible Approach to Automated Protein Crystallization," *J. Appl. Cryst.* 24:255-260 (1991).

Pearson and Lipman, "Improved tools for biological sequence comparison." *Proc Natl Acad Sci USA* 85:2444-2448 (Apr. 1988).

Pebay-Peyroula, E., et al., "X-ray Structure of Bacteriorhodopsin at 2.5 Angstroms from Microcrystals Grown in Lipidic Cubic Phases," *Science* 277:1676-1681 (1997).

Perrakis, A., et al., "Protein microcrystals and the design of a micro-diffractometer: current experience and plans at EMBL and ESRF/ID13," *Acta Cryst.* D55:1765-1770 (1999).

Presentation by Chair Graham Fleming, University of California, Berkeley: "Working Group on Biosciences," pp. 175-198, printed from http://www-als.lbl.gov/als/workshops/scidirecthtml/9BioSci/Word_Work_File_L_646, index of /als/workshops/scidirecthtml/9BioSci indicates file available in multiple formats, indicates file last modified Nov. 1998.

Presentation: NASA, Marshall Space Flight Center—Lab-on-a-Chip Based Protein Crystallization, by van der Woerd, M., dated Oct. 25, 2001, printed from worldwide web in 2002 (27 pages).

Press Release: "Berkeley Lab Research Review Summer 2000—The Crystal Robot," by Preuss, P., printed from http://www.lbl.gov/ Science- Articles/Research-Review/Magazine/2000/Winter/features on Feb. 28, 2002 (3 pages).

Press Release: "Bringing the Genome to Life Report—From the Archives: Bringing the Genome to Life—Energy Related Biology in the New Genomic World. A New Research Program for the Department of Energy's Office of Biological and Environmental Research recommended by the Biological and Environmental Research Advisory Committee. (Jun. 2000)" printed from http://doegenomestolife.org/history/genome-to-life-rpt.html on Apr. 12, 2002 (23 pages).

Press Release: "Crystallomics Core @ JCSG—Crystallomics Core," printed from http://bioinfo-core.jcsg.org/ bic/links/crystallomics.htm on Feb. 25, 2002 (2 pages with page indicating links last updated Apr. 18, 2001).

Press Release: "For Immediate Release (Sep. 25, 2000): Joint Center for Structural Genomics Funded to Advance High-Throughput Protein Structure Determination," printed from http://www.sdsc.edu/Press/00/092600.html on Feb. 20, 2002 (3 pages).

Press Release: "Large-scale Xn—The use of Microbatch for Large-Scale Crystallization Projects," by Douglas Instruments printed from http://douglas.co.uk./proposal.htm on Apr. 11, 2002 (5 pages).

Press Release: "Products —Products Feb. 2001," printed from http://www.douglas.co.uk/products.html on Mar. 2, 2002 (2 pages).

Press Release: "RAMC 2001—Poster Abstracts," printed from http//www.hamptonresearch.com/stuff/RAMC01/RAMC01PA.html on Apr, 10, 2002 (17 pages).

Press Release: "Research and Innovation: Genomics Institute of the Novartis Research Foundation (GNF), Novartis Institute for Genomics," (copyright, 1999) printed from http://www.pharma.novartis.com/research on Dec. 18, 2001 (2 pages).

Press Release: "Response to a Dec. 8, 2000, charge from the Director of the DOE Office of Science," printed from http://www.er.doe.gov/production (19 pages).

Press Release: "System Users—IMPAX and Oryx Users Feb. 2002," printed from http://www.douglas.co.uk/users.htm on Mar. 2, 2002 (3 pages).

Press Release: "TECAN Compound dissolution—Automating Drug Discovery at Zeneca," (Oct. 1998) printed from http://www.tecan.com/pr/tec_pr_DDElisa.html on Apr. 15, 2002 (1 page).

Press Release: "TECAN Genesis Workstation—Genesis Workstation," printed from http://www.tecan.com/ tec_main_genesis_workstation.html on Apr. 15, 2002 (1 page).

Press Release: "The Robot—X-ray Crystallography in Leiden," printed fro http://www.chem.Leidemuniv.nl/bfsc/robot.html on Mar. 2, 2002 (2 pages).

Press Release: "The Scripps Research Institute—News and Views—Life After the Human Genome Project: TSRI Researchers Spearhead Protein Structure Initiative," by Mika Ono Benedyk, printed from http://www.scripps.edu/newsandviews/e_20010226/print-jcsg.hml on Feb. 28, 2002 (3 pages).

Press Release: "Winners—NASA Selects Research Proposals in Cellular and Macromolecular Biotechnology" printed from http://research.hq.nasa,gov/code_u/nra/current/NRA-00-HEDS-03/winners.html.

Press Release: "PBD/Research/Research Areas/AUTOMATION," printed from http://www.lbl.gov/ LBL-Programs/pbd/xl_research/automation.html on Feb. 28, 2002 (4 pages).

Press Release: "RAMC 1999—Presentation Abstracts. Presentations T1-T16." printed from http://www.hamptonresearch.com/stuff/RAMC99/RAMC99TA.html on Apr. 8, 2002 (11 pages).

Press Release: "RAMC 2001—Presentation Abstracts. Presentations T1-T15" printed from http://www.hamptonresearch.com/stuff/RAMC01/RAMC01TA.html on Apr. 8, 2002 (12 pages).

Press Release: "Structural Biology—Charge Jun. 10, 1997—Report of the Structural Biology Subcommittte of the Biological and Environmental Research Advisory Committee—In response to the charge letter of Dr. Martha Krebs, Jun. 10, 1997," printed from http://www.er.doe.gov/ production/ober/berac/final697.html on Feb. 26, 2002 (29 pages).

Press Release: East of England Innovation Relay Centre: Pharma—Technology Offers from Europe, particularly High-throughput protein crystallization screening and polymorph screening (Reference: PAN4159) on p. 15 of document printed from http://www.stjohns.co.uk/eeirc/pharma%20offers.htm on Apr. 11, 2002 (32 pages).

Press Release: Functional Genomics. http://www.bmb.psu.edu/simpson/16genome/Function.html (1 page).

Press Release: High-throughput protein crystallization screening and polymorph screening. http://www.steinbeis- europa.de/db/ircnet_details.php? Bereich=Life&Typ=Offer&BB (Abstract).

Press Release: Jaklevic et al., "Protein Microcrystallization and Structure Determination," printed from http://www.berkeleylab.com.

Press Release: LabAutomation 2001- Annual Conference and Exhibition—LabAutomation2002—Jan. 26-30, 2002—Palm Springs California—"Preliminary Poster Program" printed on Apr. 11, 2002 from http://labautomation.org/LA/LA02/program/action.lasso?-database=LA2002Abs&-layout Apr. 11, 2002d (166 pages).

Press Release: Letter to DOE Health and Environmental Research Advisory Committee Chairman dated Jun. 10, 1997, printed from http://www.er.doe.gov/production/ober/berac/97stbio.html on Feb. 26, 2002 (2 pages).

Press Release: Letter to DOE Health and Environmental Research Advisory Committee Chairman dated May 28, 1998, printed from http://www.er.doe.gov/production/ober/berac/stbiochg.html on Feb. 26, 2002 (2 pages).

Press Release: Minutes Nov. 5-6, 1998—Biological and Environmental Research Advisory Committee (BERAC). The meeting was announced in the Federal Register for Nov. 5-6, 1998 (Pub. L. No. 92-463, 86 Stat. 770) American Geophyscial Union, Washington, D.C., printed from http://www.er.doe.gov/production/berac/11-5-98mins.html on Apr. 12, 2002 (15 pages).

Press Release: Stewart, P.S., et al., "Using Microbatch for Large-Scale Crystallization Projects," Large-scale xn—visual—printed from http://www.douglas/co.uk/glasgow.htm Aug. 1, 2002 (3 pages).

Press Release: Structural Biology, Charge May 28, 1998—Report of the Structural Biology Subcommittee of the Biological and Environmental Research Advisory Committee—In response to the charge letter of Dr. Martha Krebs, May 28, 1998 Executive Summary—Improvements recommended for current beamlines http://www.er.doe.gov/production/ober/berac/final598.html (11 pages).

Press Release: Tecan Genesis NPS—Nanopipetting for plate and array-based applications: *Miniaturize your Application with GENESIS NPS* printed from. http://www.tecan.com/tec_main_nps.html on Apr. 13, 2002 (3 pages).

Press Release: Tecan Product News—Product News from 1998, printed from http://www.tecan.com/ tec_main_product_news_98.html on Apr. 13, 2002 (3 pages).

Press Release: Tecan Product News—Product News from 1999, printed from http://www.tecan.com/tec_main_product_news_99.html on Apr. 13, 2002 (3 pages).

Press Release: Tecan Product News—Product News from 2000, printed from http://www.tecan.com/ lec_main_product_news_00.html on Apr. 13, 2002 (2 pages).

Pusey, M., et al., "Growth Kinetics of Tetragonal Lysozyme Crystals," *J. Cryst. Growth* 76:593-599 (1986).

Pusey, M.L., et al., "Protein Crystal Growth—Growth Kinetics for Tetragonal Lysozyme Crystals," *J. Biol. Chem.* 261:6524-6529 (1985).

Rawas, A., et al., "Preliminary Crystallographic Studies on Duck Ovotransferrin," *J. Mol. Biol.* 208:213-214 (1989).

Report entitled, "Physical Biosciences Division," particularly section entitled "Protein Microcrystallization Robotic System," (pp. 14-17), printed from http://www-nsd.lbl.gov/LBL-Publications/LDRD/1998/PB/index.html#Jaklevic, on Aug. 28, 2002, page indicated as last modified on Feb. 19, 1999 (17 pages).

Rippon, G.D., et al., "Improved Microdroplet Method for Quantitative X-Ray Microanalysis of Small Fluid Samples," *Micron* 24(1):17-21 (1993).

Rost, B., "Marrying structure and genomics," *Structure* 6:259-263 (1998).

Rubin, B., et al., "Minimal intervention robotic protein crystallization," *J. Cryst. Growth*. 110:156-163 (1991).

Sali, A., "100,000 protein structures for the biologist," Avalon Meeting Review, document generated Jan. 22, 1998, printed Apr. 1, 1999 from http://guitar.rockefeller.edu./avalon/review/avalon.html (7 pages).

Sanchez, et al., "Protein structure modeling for structural genomics," *Nat. Struc. Biol.* (*Structural Genomics Supplement*) 986-990 (2000).

Santarsiero, B.D., et al., "Protein Micro-Crystallization Robotics System," W0251:Protein Micro-Crystallization Robotics System (09.07:Crystallization Techniques-Lectures-Room 106- Thursday, May 27 (Abstract for ACA99 meeting) printed from http://www.hwi.buffalo.edu/ACA/ACA99/abstracts/text/W0251.html on Feb. 28, 2002 (2 pages) (website indicates last updated on May 18, 1999).

Saridakis, E., et al., "Improving protein crystal quality by decoupling nucleation and growth in vapor diffusion," *Protein Sci.* 9:755-757 (2000).

Schuetz, et al., "A novel nano-pipetting system for the development of high quality BioChip *arrays*," printed from www.tecan.com/la2000_nanopip.pdf (1 page).

Section of report entitled, "Protein Microcrystallization and Structure Determination," printed from http://www-nsd.lbl.gov/LBL-Publications/LDRD/1999/PBD.html#Stevens on Aug. 28, 2002, page indicated as last modified on Apr. 4, 2000 (3 pages).

Shapiro, L., et al., "The Argonne Structural Genomics Workshop: Lamaze class for the birth of a new science," *Structure* 6(3):265-267 (1998).

Shumate, "Low-volume (nanoliter) automated pipetting," *Am. Biotechnol Lab*. 11(6):14 (1993).

Sibille, L., et al., "Solvent evaporation rates in the closed capillary vapor diffusion method of protein crystal growth," *J. Cryst. Growth* 110:80-88 (1991).

Smith and Waterman, "Comparison of Biosequences." *Adv Appl Math* 3:482-489 (1981).

Snell, E.H., et al., "Partial Improvement of Crystal Quality for Microgravity-Grown Apocrustacyanin $C_1$," *Acta Cryst.* D53:231-239 (1997).

Soriano, Theirry M.B., et al., "ASTEC: an Automated System for Sitting-Drop Protein Crystallization," *J. Appl. Cryst.* 26:558-562 (1993).

Stevens, et al., "Global Efforts in Structural Genomics," *Science* 294:89-92 (2001).

Stevens, "High-throughput protein crystallization." [review]. *Curr. Opin. Struct. Biol.* 10(5):558-563 (2000).

Stevens, R.C., et al., Research Proposal for development and testing of a system of robotics workstations dedicated to protein crystallization., E.O. Lawrence Berkeley National Laboratory and The Scripps Research Institute, pp. 2, 29-31, 33-52, unknown date.

Stevens, Raymond C., "Design of high-throughput methods of protein production for structural biology," Structure (with Folding & Design) 8(9):R177-R185 (Sep. 15, 2000) (Available online Sep. 8, 2000).

Stevenson, "The world of Separation Science- Lab Automation '01: A Market Preparing for transition?," pp. 4-5 (2001).

Stewart, et al., "Practical experimental design techniques for automatic and manual protein crystallization," *J. Cryst. Growth* 196:665-673 (1999), printed from http://www.douglas.co.uk.rat_des.html on Mar. 2, 2002 (12 pages).

Stura, E.A., et al., "Reverse Screening," *Acta Cryst.* D50:448-455 (1994).

Swartzendruber, J.K., et al., "Apocalypse: an automated protein crystallization system. III. In the beginning: The genesis of software," (1988) p. 81, Abstract PF5, Annual Meeting of the American Crystallographic Association, Philadelphia, PA.

Tebbutt, J.S., et al., "Monitoring of crystallisation phenomena by ultrasound," *Electron. Lett.* 35(1):90-92 (1999).

Tisone, T.C., et al., "The Role of Non Contact Microfluids in High Throughput Protein Crystallization," (Abstract W0282 from ACA2002 Meeting) printed from http://www.hwl.buffalo.edu/ACA/ACA02/abstracts/text/W0282.html on Apr. 10, 2002(1 page).

Tisone, T.C., "Dispensing systems for miniaturized diagnostics," *IVD Technology Magazine*, printed from http://devicelink.com/ivdt/archive/98 (IVDI archive, May 98).

Tutorial On: the Role of Computation Biology In High-Throughput Structure Determination: Computation Before, During, and After Structural Genomics. The Role of Computational Biology in Structural Genomics, document dated Feb. 17, 1998, printed Apr. 1, 1999 from http://www.fp.mcs.anl.gov/gaasterland/sg-review-slides.htm; (14 pages).

van der Woerd, M., et al., "About Small Streams and Shiny Rocks: Macromolecular Crystal Growth in Microfluidics," (Abstract W0210 from ACA2002 Meeting) printed from http://www.hwibuffalo.edu/ACA/ACA02/abstracts/text/W0210.html.

van der Woerd, M.J., "Lab-on-a-chip Based Protein Crystallization [P-66]," *smallTalk 2001 Association for Laboratory Automation Final Conference Program*, San Diego, CA, held Aug. 27-31, 2001 (Abstract) (2 pages).

Varadarajan, R., et al., "Crystallographic Structures of Ribonuclease S Variants with Nonpolar Substitution at Position 13: Packing and Cavities," *Biochem*. 31(49):12315-12326 (1992).

Villasenor, et al., "Fast Drops: A Speedy Approach to Setting Up Protein Crystallization Trials," (Abstract W0309) from ACA01 meeting printed from http://www.hwi.buffalo.edu/ ACA/ACA01/abstracts/text/W0309.html on Dec. 21, 2001 (1 page).

Ward, K.B., et al., "Automatic Preparation of Protein Crystals Using Laboratory Robotics and Automated Visual Inspection," *J. Cryst, Growth* 90:325-399 (1988).

Ward, K.B., et al., "Automating crystallization experiments," in Crystallization of Nucleic Acids and Proteins: A Practical Approach eds. A. Ducruiz & R. Giege, Oxford Univ. Press, New York, pp. 291-310.

Weber, P.C., "Overview of Protein Crystallization Methods," *Methods in Enzymology* 276:13-22 (1997).

Weber, P.C., et al., "Experiments with automated protein crystal growth," (1987) p. 28, Abstract H5, Annual Meeting of the American Crystallographic Association, Philadelphia, PA.

Webpage: "Harvesting, Harvesting Crystals from Microbatch for Cryocrystallography," Douglas Instruments—Research Report 3, Oct. 1995, printed from http://www.douglas.co.uk/rep3.htm on Apr. 11, 2002 (4 pages).

Webpage: "Poster Session 7—Genomics, Proteomics and New Target Discovery," The Society for Biomolecular Screening~7th Annual Annual Conference and Exhibition (2001), see #7014-7015, printed from http://www.hwi.buffalo.edu/ (5 pages).

Webpage: Eickhoff, et al., "An Automated Platform for Miniaturized protein Crystallization," Greiner Bio-One (Abstract), date of last modification on web indicated as Mar. 30, 2001, printed May 2002 (1 page).

Website listing Abstracts for Oral Presentations: S7—Instrumentation—Instrumentation and Techniques for crystallization. pp. 1-3 (Nancy 20000 XIX European Crystallographic Meeting (held Aug. 25-31).

Website listing products available from Gilson, printed from http://www.gilson.com/cyberprd.htm on Feb. 22, 2001 (1 page).

Website: "A day on High-Throughput Techniques in Structural Biology," printed from http://www.embl-heidelberg.de/courses/StructureSolution02/satellite.html (5 pages) text dated Aug. 1998 and Feb. 1999.

Website: "A Recipe to grow crystals of lysozyme by the gel acupuncture technique: Granada Crystallization Box," printed from http://lec.ugr.es/GranadaCrystBox/GCG on Apr. 11, 2002 (7 pages).

Website: "Differences—The Major Differences between Oryx 6 and IMPAX 1-5," Douglas Instuments, dated Mar. 2001, printed from http://www.douglas.co.uk/differen1.htm on Apr. 11, 2002 (1 page).

Website: "General Interest II—Invited Abstracts," (Jul. 26, 2001) printed from http://www.hwi.buffalo.edu/ACA/ACA01/abstracts on Apr. 13, 2002 (2 pages).

Website: "Harima Workshop on Implementation for High-throughput Structure Determination by Protein Crystallography-Present Status and Future Goal—A Satellite of International Conference on Stuctural Genomics 2000 at Spring-8." printed from http://www.spring8.or.ip/english/conference on Dec. 19, 2001 (4 pages).

Website: "News" printed from http://www.douglas.co.uk/news.htm on Apr. 15, 2002 (2 pages).

Website: "Nobel Prize" printed from http://www.douglas.co.uk/walker.htm on Mar. 2, 2002 (1 Page).

Website: "Oryx 6—Using Oryx 6 for Crystallization with Microbacth: Microbatch operation in identical to IMPAX 1-5" printed from http://www.douglas.co.uk/oryx.htm.

Website: "PhysicsWeb—Protein crystallography: the human genome in 3-D," http://physicsweb.org/article/world/11/5/8 (May 1998), printed from website Apr. 11, 2002 (9 pages).

Website: "Publications—Journals—Trade Journals: Events Index-Abstracts and Proceedings—Achema 2000," printed from http://www.combichem.net/files/abstract1.htm on Aug. 1, 2002 (18 pages).

Website: "Impax: IMPAX 1-5 for Crystallization with Microbatch" printed from http://www.douglas.co.uk/impax.htm on Mar. 2, 2002.

Website: *Bio*Robotics http://www.biorobotics.com (Pamphlet), printed on Oct. 7, 1999 (12 pages).

Website: Garcia-Ruiz, J.M., "The role of gravity in protein crystallization: Is there an effect of gravity on the crystallization process," printed from http://lec.ugr.es/esatt/Role_of_gravity/Role.html on Apr. 11, 2002 (3 pages).

Website: Micro-Arraying with the *Micro* Grid http://www.biorobotics.com/MicroArray.html, printed Oct. 20, 1999 (6 pages).

Wilson, S.A., et al., "Crystallization of and Preliminary X-ray Data for the Negative Regulator (AmiC) of the Amidase Operon of *Pseudomonas aeruginosa,"* *J. Mol. Biol*. 222(4):869-871 (1991).

Yakovlev, Y.O., et al., "A Laboratory Apparatus for Crystal Growth from Solution," *Instruments and Exp. Tech*. 41(2):292-296 (1998).

Yegian, D., "Task-specific robotics for sample loading, centering and retrieval," printed from http://smb.slac.stanford.edu/jcsg/robotics/abstracts/dy_abs.html on Apr. 12, 2002 (1 page) (site last modified Oct. 16, 2000).

Zeelen, J. Ph., et al., "Crystallization Experiments with 2-Enoyl-CoA Hydratase, Using an Automated 'Fast Screening' Crystallization Protocol," *Acta Cryst*. D50:443-447 (1994).

Zeppezauer, M., "Microdiffusion cells for the growth of single protein crystals by means of equilibrium dialysis," *Arch. Biochem. Biophys*. (1968) 564-573.

"BMST Pervasive Technologies—Concept Paper, BMST Initiative Thrust Area: Emerging of Breakthrough Process Technologies—Definition of the Thrust Area—NACFAM," printed from http://www.nacfam.org/bmst/bmstemergingtechnologies.html on Feb. 26, 2002 (5 pages).

"Hampton Research—Solutions for Crystal Growth," printed from http://www.hamptonresearch.com on Feb. 22, 2001 (2 pages).

"High throughput protein crystallization—EMBL Practical Course on Protein Expression, Purification and Crystallization—Aug. 14th-20th, 2000 EMBL Outstation Hamburg, Germany," printed from http://www.structure.llnl.gov/Xray/tutorial/High_Throughput_EMBL_full.html on Apr. 12, 2002 (10 pages).

"High-Throughput Structure Determination in an Informatics Environment," (2001) printed from http://www.accelrys.com/webzine on Aug. 1, 2002 (4 pages).

\* cited by examiner

Figure One

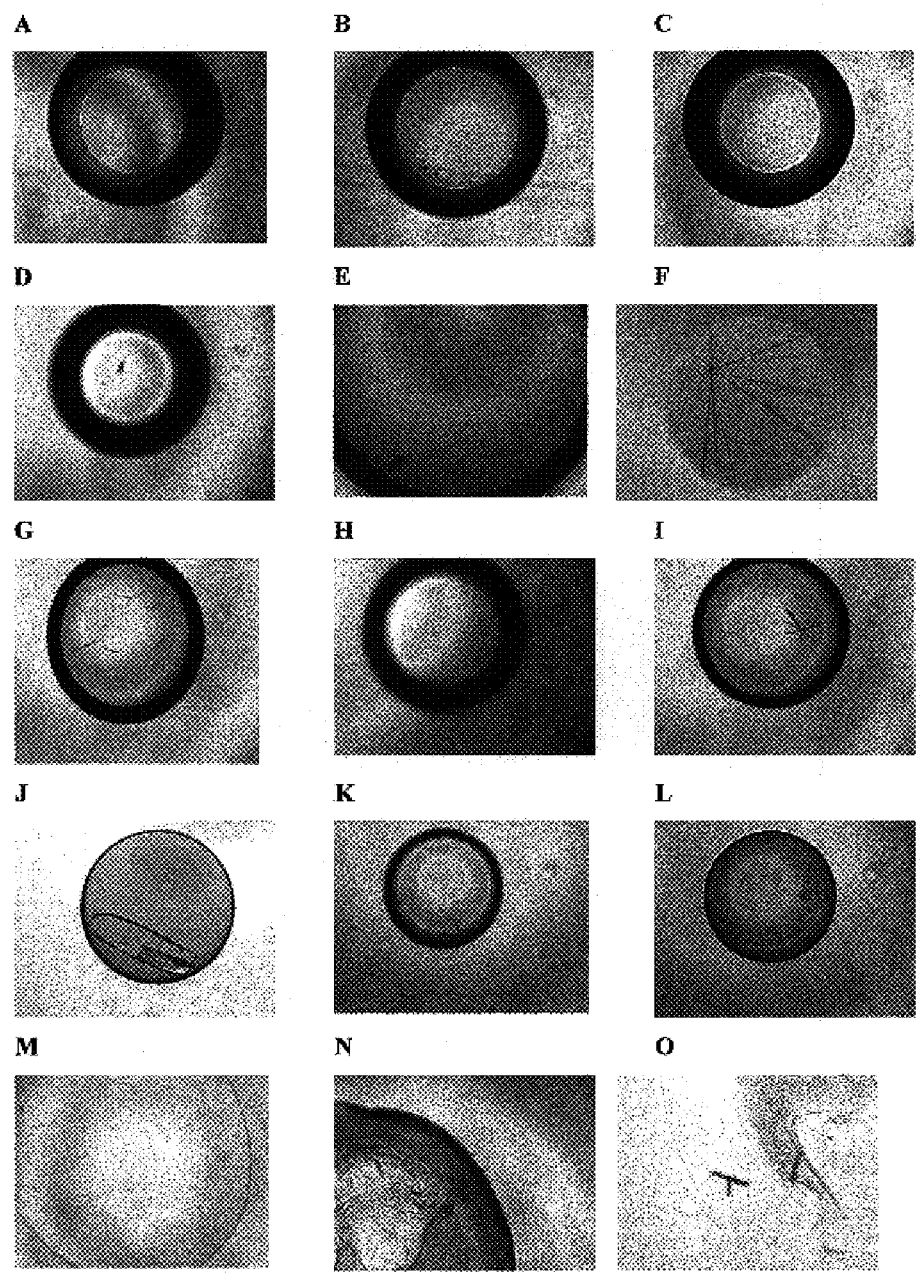
Figure Five

US 7,250,305 B2

USE OF DYE TO DISTINGUISH SALT AND PROTEIN CRYSTALS UNDER MICROCRYSTALLIZATION CONDITIONS

CROSS-REFERENCE TO RELATED APPLICATIONS

This application claims the benefit of priority of U.S. Provisional Application No. 60/308,698, filed Jul. 30, 2001, to Provisional Application Ser. No. 60/328,958, filed Oct. 12, 2001, and to U.S. application Ser. No. 09/543,326, filed Apr. 5, 2000, which claims benefit of U.S. Provisional Application 60/128,018, filed Apr. 6, 1999, each of which are hereby incorporated in their entirety herein by reference.

STATEMENT OF GOVERNMENT SUPPORT

This invention was made with government support under NASA Cooperative Agreement No. NCC8-246. The government may have certain rights in the invention.

FIELD OF THE INVENTION

This invention relates generally to the method of using detectable agents in crystallization of proteins, wherein the detectable agents are preferentially incorporated in the crystals of proteins or preferentially not incorporated in the crystals of proteins such that protein crystals can be readily distinguished from crystals of other substances which can form under the crystallization conditions, thereby allowing rapid and straightforward characterization of crystals and evaluation of crystallization conditions used to obtain the crystals.

SUMMARY OF THE INVENTION

In accordance with the purpose(s) of this invention, as embodied and broadly described herein, this invention relates to a method of using dyes to facilitate the characterization of protein crystals present in volumes of one microliter or less. Specifically, it relates to the crystallization of proteins from protein solutions containing dyes under conditions wherein the proteins which crystallize and the other components of the protein solutions which crystallize can be distinguished from one another on the basis of whether or not they form dyed crystals.

In a first aspect, this invention relates to a method for forming a dyed protein crystal including the steps of: (1) providing a protein solution, wherein the protein solution contains at least one dye, which dye is capable of dyeing at least a portion of protein crystals formed from the protein solution; (2) subjecting the protein solution to environmental conditions effective to form protein crystals; and (3) detecting the presence of dyed protein crystals, whereby the presence of the dyed protein crystals indicates the presence of protein crystals.

In various preferred embodiments of the first aspect of the invention, the dye can be chosen from the group consisting of methylene blue, methylene green, Izit[1] and crystal violet.

In various preferred embodiments of the first aspect of the invention, the protein solution is partitioned from the atmosphere. When the protein solution is partitioned from the atmosphere, the partitioning can be done so as to lower the rate at which transfer of solvent from the protein solution occurs. The protein solution can be partitioned from the atmosphere by overlaying the protein solution with an oil. The overlaying oil can be selected from the group consisting of paraffin oil, silicone oil or a combination thereof, for example, AL's oil[1] (a 1:1 mixture of paraffin and silicone oil). The particular mixture of oil selected can be optimized for the rate at which transfer of solvent from a protein solution occurs when the protein solution is overlayed with a particular mixture of oil. Further, the amount of oil overlaying the protein solution can be selected so as to optimize the rate of solvent transfer from the protein solution, in particular, from the protein solution to the oil and from the oil to the atmosphere.

[1]Reagent is commercially available from Hampton Research, Inc. (www.hamptonresearch.com)

In various preferred embodiments of the first aspect of the invention, the protein solution further includes a component selected from the group consisting of salts, buffers, precipitants, crystallization aids and any combination thereof. The component selected can crystallize under the controlled environmental conditions to which the protein solution is subjected, thereby producing component crystals. The conditions under which the component crystallizes, can include the step or process of adding a precipitate solution. The component crystals formed can be undyed component crystals.

In various preferred embodiments of the first aspect of the invention, any crystals formed in the provided protein solution can be detected. If crystals are detected, dyed protein crystals can be distinguished from undyed component crystals. The protein crystals and component crystals can be detected by microscopy.

In a second aspect, this invention relates to a method for screening protein crystal growth conditions, including the steps of: (1) providing a set of at least two protein solutions, wherein the protein solutions contain a dye, which is capable of dyeing at least a portion of protein crystals formed from the protein solution and which does not dye a significant portion of component crystals formed from the protein solution; (2) subjecting the protein solutions to predetermined conditions, wherein the environmental conditions to which each member of the set of protein solutions is subjected is not identical to the environmental conditions to which another member of the set is subjected; and (3) detecting the presence or non-presence of dyed protein crystals and/or undyed component crystals, wherein the presence of the dyed protein crystals indicates the formation of protein crystals; and the presence of undyed component crystals indicates formation of component crystals.

In various preferred embodiments of the second aspect of the invention, the set of protein solutions consists of greater than 10, 50, 100, 250, 500, 1000, 1500, 2000 or 5000 protein solutions.

In various preferred embodiments of the second aspect of the invention, the dye can be chosen from the group consisting of methylene blue, methylene green, Izit[1] and crystal violet.

In various preferred embodiments of the second aspect of the invention, the protein solutions are partitioned from the atmosphere. When the protein solutions are partitioned from the atmosphere, the partitioning can be done so as to lower the rate at which transfer of solvent from the protein solutions occurs. The protein solutions can be partitioned from the atmosphere by overlaying the protein solutions with an oil. The overlaying oil can be selected from the group consisting of paraffin oil, silicone oil or a combination thereof, for example, AL's oil[1] (a 1:1 mixture of paraffin and silicone oil). The particular mixture of oil selected can be optimized for the rate at which transfer of solvent from a protein solution occurs when the protein solution is overlayed with a particular mixture of oil. Further, the amount of oil overlaying the protein solution can be selected so as to optimize the rate of solvent transfer from the protein solution, in particular, from the protein solution to the oil and from the oil to the atmosphere.

In various preferred embodiments of the second aspect of the invention, the protein solutions further include a component selected from the group consisting of salts, buffers, precipitants, crystallization aids and any combination thereof. The component selected can crystallize under the controlled environmental conditions to which the protein solution is subjected, thereby producing component crystals. The conditions under which the component crystallizes, can include the step or process of adding a precipitate solution. The component crystals formed can be undyed component crystals.

In various preferred embodiments of the second aspect of the invention, any crystals formed in the provided protein solutions can be detected. If crystals are detected, dyed protein crystals can be distinguished from undyed component crystals. The protein crystals and component crystals can be detected by microscopy.

In various preferred embodiments of the second aspect of the invention, the detection of dyed protein crystals indicates a combination of environmental conditions to promote crystal growth of a protein in the provide protein solutions. When dyed proteins are detected, the dyed protein crystals can be evaluated in respect to protein crystal quality. Evaluation of protein crystal quality can include consideration of criteria selected from the group consisting of, but not limited to, size of crystals, volume of crystals, intensity of coloration of crystals by dye, color of coloration of crystals by dye, sharpness of crystal edges, and crystal shape.

In various preferred embodiments of the second aspect of the invention, the suitability of crystallization conditions can include evaluation of the protein crystal quality of the crystals obtained by a certain set of environmental conditions.

In a third aspect, this invention relates to a method of forming a dyed component crystal including the steps of: (1) providing a component solution, wherein the component solution contains at least one dye, which dye is capable of dyeing at least a portion of component crystals formed from the component solution; (2) subjecting the component solution to environmental conditions effective to form component crystals; and (3) detecting the presence of dyed component crystals, whereby the presence of the dyed component crystals indicates the presence of component crystals.

In various preferred embodiments of the third aspect of the invention, the component solution is partitioned from the atmosphere. When the component solution is partitioned from the atmosphere, the partitioning can be done so as to lower the rate at which transfer of solvent to or from the component solution occurs. The component solution can be partitioned from the atmosphere by overlaying the component solution with an oil. The overlaying oil can be selected from the group consisting of paraffin oil, silicone oil or a combination thereof, for example, AL's oil[1] (a 1:1 mixture of paraffin and silicone oil). The particular mixture of oil selected can be optimized for the rate at which transfer of solvent to or from the component solution occurs when the component solution is overlayed with a particular mixture of oil. Further, the amount of oil overlaying the component solution can be selected so as to optimize the rate of solvent transfer to or from the component solution, in particular, from the component solution to the oil, or vice versa, and from the oil to the atmosphere, or vice versa.

In various preferred embodiments of the third aspect of the invention, the component solution further includes a protein. The protein selected can crystallize under the controlled environmental conditions to which the component solution is subjected, thereby producing protein crystals. The conditions under which the protein crystallizes, can include the step or process of adding a precipitate solution. The protein crystals formed can be dyed protein crystals.

In various preferred embodiments of the third aspect of the invention, any crystals formed in the provided component solution can be detected. If crystals are detected, protein crystals can be distinguished from component crystals on the basis that the protein crystals are undyed protein crystals and the component crystals are dyed component crystals. The protein crystals and component crystals can be detected by microscopy.

In a fourth aspect, this invention relates to a method for screening protein crystal growth conditions including the steps of: (1) providing a set of at least two protein solutions, wherein the protein solutions contain a dye, which is capable of dyeing at least a portion of component crystals formed from the protein solution and which does not dye a significant portion of protein crystals formed from the protein solution; (2) subjecting the protein solutions to predetermined conditions, wherein the environmental conditions to which each member of the set of protein solutions is subjected is not identical to the environmental conditions to which another member of the set is subjected; and (3) detecting the presence or non-presence of undyed protein crystals and/or dyed component crystals. The presence of the undyed protein crystals can indicate the formation of protein crystals and the presence of the dyed component crystals can indicate formation of component crystals.

In various preferred embodiments of the fourth aspect of the invention, the set of protein solutions consists of greater than 10, 50, 100, 250, 500, 1000, 1500, 2000 or 5000 protein solutions.

In various preferred embodiments of the fourth aspect of the invention, the protein solutions are partitioned from the atmosphere. When the protein solutions are partitioned from the atmosphere, the partitioning can be done so as to lower the rate at which transfer of solvent from the protein solutions occurs. The protein solutions can be partitioned from the atmosphere by overlaying the protein solutions with an oil. The overlaying oil can be selected from the group consisting of paraffin oil, silicone oil or a combination thereof, for example, AL's oil[1] (a 1:1 mixture of paraffin and silicone oil). The particular mixture of oil selected can be optimized for the rate at which transfer of solvent from a protein solution occurs when the protein solution is overlayed with a particular mixture of oil. Further, the amount of oil overlaying the protein solution can be selected so as to optimize the rate of solvent transfer from the protein solution, in particular, from the protein solution to the oil and from the oil to the atmosphere. The overlaying oil used, or the amount of overlaying oil used, to partition any single protein solution from the atmosphere can be the same or can be different than the overlaying oil used to partition any other protein solution from the atmosphere.

In various preferred embodiments of the fourth aspect of the invention, the protein solutions can further include a component selected from the group consisting of salts, buffers, precipitants, crystallization aids and any combination thereof. The component selected can crystallize under the controlled environmental conditions to which the protein solution is subjected, thereby producing component crystals. The conditions under which the component crystallizes, can include the step or process of adding a precipitate solution. The component crystals formed can be dyed component crystals.

In various preferred embodiments of the fourth aspect of the invention, crystals formed in the provided protein solutions can be detected. If crystals are detected, protein crystals can be distinguished from component crystals on the basis that the protein crystals are undyed protein crystals and the component crystals are dyed component crystals. The protein crystals and component crystals can be detected by microscopy.

In various preferred embodiments of the fourth aspect of the invention, the detection of undyed protein crystals indicates a combination of environmental conditions to promote crystal growth of a protein in the provided protein solutions. When undyed proteins are detected, the undyed protein crystals can be evaluated in respect to protein crystal quality. Evaluation of protein crystal quality can include consideration of criteria selected from the group consisting of, but not limited to, size of crystals, volume of crystals, intensity of coloration of crystals by dye, color of coloration of crystals by dye, sharpness of crystal edges, and crystal shape.

In various preferred embodiments of the fourth aspect of the invention, the method of screening the suitability of crystallization conditions can include an evaluation of the characteristics, numbers or types of component crystals formed.

Additional advantages of the invention will be set forth in part in the description, which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

For instance, one advantage provided by one aspect of the invention is that the use of the dye to distinguish between salt and protein crystals allows rapid screening of crystals formed in volumes of less than or equal to approximately one microliter to distinguish between those formed of salt and those formed of protein. The methods known to the art at this time that are used to distinguish between crystals of salt and crystals of protein are not able to achieve this result. The methods used now: (1) the "crush test" where an investigator feels and listens for the sound of salt cracking; (2) bombardment of a crystal by x-rays and subsequent diffraction pattern analysis; and (3) addition of dye after a crystal has been grown and observation of staining; each require a crystal of suitable size (0.3 mm×0.3 mm×0.3 mm). Crystals grown from volumes of solution less than or equal to approximately one microliter are too small for these classical methods of analysis. The salt and protein crystals formed are too small to crush or to manipulate effectively for x-ray bombardment. Also, because the volumes in which the crystals are formed are so small, addition of any feasibly manipulated volume of dye solution has significant effects on the composition of the solution containing the crystals and, therefore, significant effects on the crystals therein. Furthermore, as use of such small volumes requires that the crystals be grown in solutions partitioned from the atmosphere, generally by an overlaying oil, it is extremely difficult to add a dye reagent to protein solutions containing crystals. Inclusion of protein solutions prior to crystal growth provides an extremely efficient and simple method to screen for protein crystals in volumes of less than one microliter. Further, this method reduces the time, cost, and skill labor requirements for screening procedures as well as lending itself to forms of automated screening, including for example, methods of automated screening described in U.S. application Ser. No. 09/543,326 incorporated herein by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Izit under oil. (FIG. 1B) NaCl under oil. (FIG. 1C) NaCl+dye under oil. (FIG. 1D) Lysozyme under oil. (FIG. 1E) Lysozyme+dye under oil. (FIG. 1F) Thaumatin under oil. (FIG. 1G) Thaumatin+dye under oil. (FIG. 1H) Catalase under oil. (FIG. 1I) Catalase+dye under oil. (FIG. 1J) Trypsin under oil. (FIG. 1K) Trypsin+dye under oil using CS15. (FIG. 1L) Trypsin+dye under oil using CS16. In each trial, the oil was AL's oil, 50:50 mixture of paraffin oil and silicone oil and the dye was Izit.

FIG. 5 depicts micrograph images of additional crystallization trials. FIGS. 5A–5D depict trials conducted using Izit w/o any added protein under various screening conditions. 5E–5F depict trials with added β-lactoglobulin. FIGS. 5G–5I depict trials with added myristol transferase. FIG. 5J depicts trials with added pepsin. FIGS. 5K and 5L depict trials with protein Renac2. FIGS. 5M and 5N depict trials with protein ROB1. FIG. 5O depicts a trial with protein B10.

DESCRIPTION OF THE PREFERRED EMBODIMENTS

Figure 1:
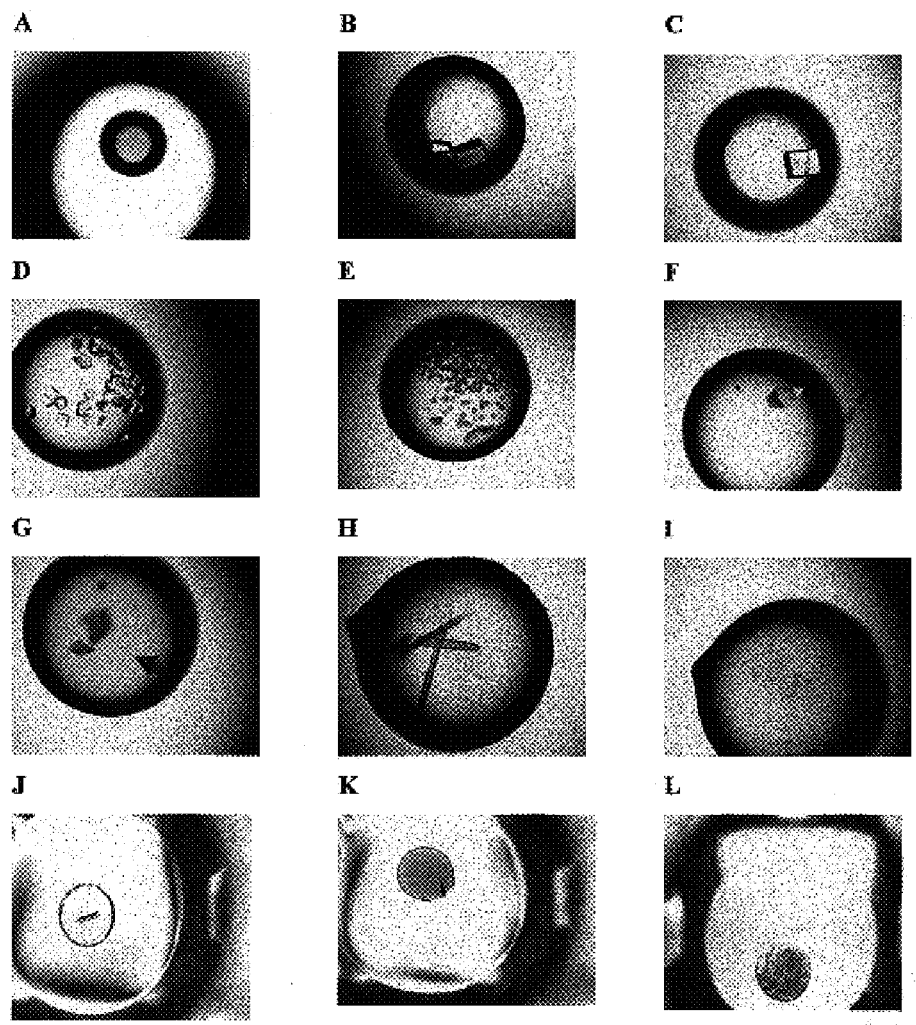
FIG. 1 depicts micrograph images of crystallization trials.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific methods of using dye to distinguish between crystals of interest and crystals of other character, specific dyes, to specific methods of detecting dyed crystals or to particular uses of the method disclosed herein, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a dye" includes mixtures of dyes, reference to "a component" includes mixtures of two or more such components, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims, which follow, reference will be made to a number of terms, which shall be defined to have the following meanings:

"Optional" or "optionally" means that the subsequently described event or circumstance may or may not occur, and that the description includes instances where said event or circumstance occurs and instances where it does not. For example; the phrase "solution optionally containing precipitate" means that the solution may or may not contain precipitate and that the description includes both a solution without precipitate and a solution with a precipitate.

"Detectable," as used herein, means that the presence or absence of the molecule or species so described can be determined. Alternatively, "detectable," as used herein, means that the presence or absence of a certain property or characteristic of a molecule or species so described can be determined. For example, a visually detectable characteristic or property of a species or object, such as a crystal, includes, but is not limited to, the intensity, shade and hue of the species or object.

"Dye," as used herein, means an agent which renders another molecule or species detectable by its action on or association with the other molecule or species. Generally, a dye will refer to a visually detectable small molecule, which interacts with, i.e. stains or colors, another molecule. However, dye, as used herein, may also mean an agent that acts on another molecule to render it detectable. Dye, as used herein, may also mean an agent, which absorbs or emits electromagnetic radiation outside of the visible spectrum, e.g., electromagnetic radiation within the ultraviolet spectrum.

"Environment" or "environmental conditions," as used herein, means the sum total of all the conditions and elements that make up the surroundings and influence the development of any species subject to the environment. The environmental conditions of a protein in solution can be defined in part by description of a limited number of conditions and elements, including but not limited to the identity and abundance of atoms or molecules in solution, including but not limited to solvents, solutes and precipitates; other conditions such as but not limited to pH, temperature and pressure; and the magnitude and orientation of other forces, including but not limited to gravitational forces, magnetic forces and electrostatic forces.

It will be recognized by one of skill in the art that individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and 6) Phenylalanine (F), Tyrosine (Y), Tryptophan (W).

Further, it will be recognized by one of skill in the art that two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The dye(s) used in the practice of the invention may have no effect on the crystallization of a protein contained in the solution. While not being bound by theory, it is contemplated that the nature of the interaction between the selected dyes and protein crystals is such that it has no effect on the structure, stability or growth characteristics of the protein crystals of interest.

The dye(s) used in the practice of the invention may have a negligible effect on the crystallization of proteins contained in the solution. For example, protein crystals formed in the presence of the dye may be functionally equivalent in respect to their use to determine the structure of the crystallized protein, even though the protein crystals grown in the presence of the dye can be distinguished from the protein crystals grown in the absence of the dye on the basis of criteria that can be used to evaluate protein crystal quality, including the size of crystals, volume of crystals, sharpness of crystal edges and crystal shape.

The dye(s) used in the practice of the invention may have a significant effect on the crystallization of proteins contained in the solution. For example, the protein crystals' growth may be significantly slower when the protein solution contains the dye or the protein crystals' growth may be significantly faster when the protein solution contains the dye. Significant differences in the growth rate of protein crystals are those greater than 5, 10, 15, 25, 50, 75, 100, 500 or 1000 fold different. Also, the quality of the crystals may be significantly different, as measured by the criteria for determining a protein crystal's quality, for example, size of crystals, volume of crystals, intensity of coloration of crystals by dye, color of coloration of crystals by dye, sharpness of crystal edges, and crystal shape.

It will be recognized that under some conditions, for example, when using Izit dye under high salt conditions and at low pH, colored dye crystals can be formed in the absence of protein. It will also be recognized that under some conditions, certain buffer components or salts can crystal with the dyes used to form colored crystals. Formation of such colored dye-only or colored component crystals can be detected by screening for the formation of colored crystals in the absence of any added protein or biomolecule of interest. Detection of the presence or absence of such colored crystals under such conditions can be used by one of skill in the art to evaluate the authenticity of colored crystals formed under such conditions when protein or the biomolecule of interest is present.

Screening protein crystal growth conditions, as is described herein, refers broadly to the process of providing at least two protein solutions and subjecting them to different conditions and then determining whether or not the conditions allow for the crystallization of proteins included in the protein solution. The protein solutions, unless otherwise indicated, contain the same protein species, which is the protein of interest. When the protein solutions contain the same protein of interest, the environmental conditions that a given protein solution is subjected to can differ. The protein solutions can also contain different protein species. When the protein species contained in the different protein solutions differ, the protein species that differ may be either the protein of interest and/or other proteins. The protein of interest, as will be recognized by those of skill in the art, is the protein for which the evaluation of protein crystallization conditions is intended. In other words, if an investigator is seeking to establish suitable conditions for the crystallization of protein X, then protein X is the protein of interest.

The volume of a protein solution used in the method of forming dyed or undyed protein crystals or in screening protein crystallization conditions, as is described herein, can be greater than 1, 5, 10, 25, 50, 75, 100, 150, 200, 250, 300, 400, 500, 600, 700, 800 or 900 pico-, nano-, or micro-liters. The volume of a protein solution used in the method of forming dyed or undyed protein crystals or in screening protein crystallization conditions, as is described herein, can be less than 5, 10, 25, 50, 75, 100, 150, 200, 250, 300, 400, 500, 600, 700, 800, 900, or 1000 milli-, micro-, nano- or pico-liters.

"Partitioned," as used herein, refers to the segregation of the protein solution from the atmosphere such that the transfer of at least one species present in the solution from the solution to the atmosphere occurs at a lower rate than when the protein solution is not partitioned from the atmosphere. For example, segregation of the protein solution from the atmosphere by the interposition of a semipermeable membrane, which allows the passage of certain solvent molecules, but not others, would partition the protein solution from the atmosphere. When the protein solution is partitioned from the atmosphere, the partitioning may be done so as to lower the rate at which transfer of solvent from the protein solution occurs. The protein solution may be partitioned from the atmosphere by overlaying the protein solution with an oil. The overlaying oil may be selected from the group consisting of paraffin oil, silicone oil or a combination thereof, for example, AL's oil[1] (a 1:1 mixture of paraffin and silicone oil). The particular overlaying oil selected may be optimized for the rate at which transfer of solvent from a protein solution occurs when the protein solution is overlayed with a particular mixture of oil. Paraffin oil is more restrictive to evaporation of water from the overlayed protein solution than either silicone oil or mixtures containing paraffin oil and silicone oil. Mixtures of the two oils can be used where the rate of evaporation to be allowed falls between the rate allowed when 100% paraffin oil is used and when 100% silicone oil is used. Mixtures of the two oils having higher paraffin oil/silicone oil ratios are more restrictive to transfer of water molecules than those mixtures of oil having lower paraffin oil/silicone oil ratios. In mixtures of the two oils, the %(v/v) of either of the two oils, either the paraffin oil or the silicone oil, can be 5, 10, 15, 20, 25, 30, 35, 40, 45, 50, 55, 60, 65, 70, 75, 80, 85, 90 or 95%.

The practice of protein crystallization to provide crystals suitable for x-ray diffraction and/or other methods of analysis is often hampered by the difficulty in obtaining crystals of sufficient size and quality for analysis. Thus, the most powerful technique currently available for studying the structure of large molecules can often not be applied to molecules for which there is a need for greater understanding to solve pressing questions relating to the health and welfare of humankind. While the barrier of insufficient crystal quality can often be breached with the application of sufficient resources, the elucidation of the conditions required to produce suitable crystals for x-ray analysis is a significant undertaking. The process for determining suitable conditions generally requires large amounts of both highly skilled labor and highly purified protein.

The application and use of the invention greatly decreases both the quantity of labor and protein required to screen potential crystallization conditions to obtain effective crystallization conditions to provide the suitable high quality crystals required for x-ray crystallography of biomolecules for the use in structure based drug design and the attendant benefits thereof.

The significance of the improvement provided by the invention can be appreciated better in light of what is provided by other state-of-the-art practices relating to x-ray crystallographic analysis. In particular, the current automated processes, the availability of intense x-radiation from synchrotron sources and improvements in calculating phases, either from molecular replacement or multiple anomalous dispersion (MAD) strategies, all appear able to handle large numbers of crystallized proteins for structure determination. However, none of these aforementioned processes provide the information necessary, or the means, for identifying the proper environmental conditions to form crystals of molecules for growth, diffraction and/or analysis.

The method of the present invention produces a significant aid in determining the conditions suitable for crystallizing proteins, thereby greatly facilitating the production of suitable protein crystals for structural determination without the excessive expenditure of limited resources.

In particular, the presently disclosed method can facilitate a great reduction in the quantity of protein needed for the screening of large numbers of crystallization conditions and the time required to analyze the outcome of each crystallization condition trial. It does so by allowing rapid discrimination between crystals of protein and crystals of other components present in a crystallization trial in very small volumes. Furthermore, the ease in discrimination between protein crystals of interest and crystals of other materials (e.g., salt, buffer, precipitants) is of particular usefulness when the presently disclosed use of dye to distinguish between protein and salt crystals is applied to pico, nano or meso scale crystallization trials performed in a microarray or other micro-device.

In accomplishing the presently disclosed method, the crystallization trials, or necessary parts thereof, can be automated. As the method used to characterize the nature of crystals present does not require physical contact between the crystal of interest and a probe or other such element, as is required for testing of crystals using conventional means, the method is more amenable to automation than conventional methods now used to determine that a crystal is a protein crystal. Embodiments of the method that are automated are contemplated and provide for the preparation and/or rapid analysis of many samples in high throughput applications.

Automated systems to form solutions for preparing crystallization trials, to conduct trials and to monitor the resulting crystallizations, can include any of those features and aspects as described in U.S. provisional application 60/128, 018 and U.S. utility application Ser. No. 09/543,326 both of which are incorporated herein by reference in their entirety. However, the automated systems or components thereof need not include all features described in the previous applications. Minimally, a fully automated system need only include an automated dispensing system to deliver crystallization trial volumes to receptacles, a capability to provide an environment in which crystals can form under at least some conditions, and an ability to detect the presence or absence of formed crystals. The present invention includes the use of dye to facilitate the detection of crystals. Thus, devices of the present invention adapted for automated screening do provide solutions containing the appropriate selected dye and do provide an environment that allows detection of dyed crystals. In one aspect, provision of that environment is effected by use of wells having clear sides or a clear path for optical detection. As will be recognized by one of skill in the art, such an environment need not provide such a clear optical path provided other means for detecting the presence of the dyed crystals is provided. Examples of such other means include, but are not limited to, detectors present within the wells, devices for removal of crystals from wells, and detectors as are known in the art that do not rely upon the presence of a clear optical path, but instead rely on other physical or chemical properties.

In particularly useful embodiments contemplated, the method can include use of an automated system that dispenses the appropriate solutions to form a crystallization trial that includes the presence of a dye useful in the practice of the invention and overlays the crystallization trial with an oil. Such an automated solution can include a microarray for crystallization trials, an automated dispensing mechanism for dispensing the solutions, an automated dispensing mechanism for dispensing the overlaying oil, and an automated means for detecting crystal growth.

In particularly useful embodiments contemplated, the method can encompass use of an analysis station that detects the color of crystals in samples that are provided to the analysis station in an automated fashion. As will be recognized by those of ordinary skill in the art, detection of crystal color can include the monitoring and detection of selected portions of the spectra of electromagnetic radiation that are absorbed, reflected or transmitted by a crystal, whereby detection of said selected portions of the spectra are indicative of a color.

Such automated methods can further include the sorting of crystals in regard to their determined characteristics. Such sorting can be of a physical nature (i.e., the samples containing the crystals are segregated according to the nature of crystals contained therein) or can be of an informational nature (i.e., the identity of samples containing crystals of a particular nature and/or the location of crystals of a particular nature within a sample are recorded).

Such automated methods can also include determination of the number of crystals or objects of specified character or identity within a given sample, set of samples or other groups. Further, the number and identity relating to obtained crystals can also be used as a descriptor of conditions used to obtain crystals. For example, the total number of biomolecule crystals obtained and/or the fraction of crystals obtained that are biomolecule crystals can be used to describe results obtained using specific sets of conditions that can be used to form crystals of a specified character.

The automated method can monitor samples or crystals within samples. The automated method can operate in response to a predetermined program. The predetermined program can include input or instructions from the user. Input or instructions can be provided prior to the screening process or can be provided during the screening process either in response to queries generated by the predetermined program or by the initiative of the user.

Data obtained from the method can include images and data sets representing images or data derived from both images or selected portions of images. Images can be acquired automatically, with user action or with a combination of both automated and non-automated processes. Particular details regarding details of data analysis and determination of whether a biomolecule or a nonbiomolecule (i.e., a protein crystal or a salt crystal) will, of course, vary depending on the characteristics of the crystallization conditions and the dye being used. Optimization of such particular details are well understood by those of skill in the art and would be recognized not to rise to the level of undue experimentation.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE ONE

Crystallization of Selected Proteins from Protein Solutions Containing Izit

Introduction

The ability to distinguish between salt and protein crystals has been a problem solved by conventional x-ray crystallographers in a variety of methods. Those methods include the "crush" test whereby a crystal is crushed and determined to be salt if it makes a cracking sound. A second method involves placing the crystal in a x-ray beam and looking for diffraction resolution. A third method includes the addition of a dye composed of methylene blue under the commercial name of Izit to the volume containing a crystal. Theoretically, a crystal of protein contains large channels of solvent and will readily uptake the dye, while a crystal of salt is so well packed that the dye will not be taken up into the salt crystal. Each of these methods has their pros and cons. The crush test con is readily apparent, crush your protein crystal and you're back to the starting point. Mounting crystals and shooting to ascertain their ability to diffract takes a significant amounts of time and effort. The addition of dye to stain protein crystals is clearly useful, even if not 100% accurate. However, the addition of dye to stain crystals resulting from a crystallization trial cannot be easily used under certain circumstances, particularly those circumstances where small volumes are required.

The process for high through put screening for protein crystallization conditions has been miniaturized which thus improves efficiency, but results in the growth of unmanageably small crystals. The crystals are too small for either the crush test or x-ray analysis, due to difficulty in handling, indeed, even addition of dye to the small volumes and to the small crystals is difficult. A simple solution to the problem, the scaling up of various trials to determine if crystals were salt or protein, results in the creation of a bottleneck for high flux structure determination projects, thus negating one of the primary advantages sought in the miniaturization of the screening process.

Herein, an alternative method of discriminating between protein and salt crystals is disclosed. As described in this example for the purpose of illustration, it includes the addition of a blue dye to crystallization trials of approximately one microliter or lower volumes under paraffin oil as an aid to the detection and the characterization of protein crystals and/or the characterization of crystals as protein crystals.

Materials and Methods:

The proteins screened in this example were: hen egg white lysozyme (Boehringer Mannheim, 1243004), 30 mg/ml in 0.1 M sodium acetate (pH 4.7); thaumatin (Sigma, T7638), 30 mg/ml in 100 mM Tris-HCl (pH 6.5); bovine catalase (Sigma, C40), 30 mg/ml in 50 mM HEPES (pH 7.0); cellulase from *T viride* (Sigma, C40), 40 mg/ml in 100 mM Tris-HCl (pH 8.5); bovine trypsin (Sigma, T8253), 60 mg/ml in 25 mM HEPES (pH 7.0), 10 mM $CaCl_2$, 10 mg/ml benzamidin HCl; porcine pepsin (Sigma, P6887), 60 mg/ml in 100 mM cacodylate buffer (pH 6.5), 0.2 M Ca acetate; equine serum albumin (Sigma, A3434), 50 mg/ml in 50 mM sodium acetate (pH 5.5); *Bacillus lichenformis* α-amylase (Sigma, A4551), 25 mg/ml in 50 mM cacodylate buffer (pH 6.75), 2 mM $CaCl_2$; Barley β-amylase (Sigma, A7130), 8 mg/ml in 100 mM HEPES (pH 7.5); bovine β-lactoglobulin (Sigma, L3908), 10 mg/ml in 100 mM Tris-HCl (pH 6.5). Precipitants were prepared using reagents from Sigma or Hampton Research. Paraffin oil and Izit were purchased from Hampton Research. Izit is a commercial preparation of methylene blue dye, a planar aromatic dye with a molecular weight of 319 daltons. Crystallization trials were performed in Labsystems 384 clinical plates under 40 μl of paraffin oil. Crystallization buffers used for: lysozyme (100 mM sodium acetate (pH 4.7), 7% NaCl); thaumatin (1.5 M sodium potassium tartrate); catalase (Crystal Screen 36 (Hampton Research), 100 mM Tris (pH 8.5), 8% PEG8000)); cellulase (1.4 M ammonium sulfate); trypsin (Crystal Screens 4, 15, 16, 20, 28,30, 31 (Hampton Research), namely for, (4) 0.1 M Tris-HCl (pH 8.5), 2.0 M ammonium sulfate; (15) 0.2 M ammonium sulfate, 0.1 M sodium cacodylate (pH 6.5), 30% PEG8000; (16) 0.1 M HEPES (pH7.5), 1.5 M lithium sulfate monohydrate; (20) 0.2 M ammonium sulfate, 0.1 M sodium acetate trihydrate (pH 4.6), 25% PEG4000; (28) 0.2 M sodium acetate trihydrate, 0.1 M sodium cacodylate (pH 6.5), 30% PEG8000; (30) 0.2 M ammonium sulfate, 30% PEG8000;(31) 0.2 M ammonium sulfate 30% PEG4000; pepsin, 18% PEG8000; equine serum albumin, 2.0 M ammonium sulfate; α-amylase, 1 N NaOH; β-amylase, 0.17 M ammonium sulfate, 15% PEG8000; β-lactoglobulin, 2.0 M ammonium sulfate.

Crystallization trials were initiated by mixing equal portions of protein and precipitant solutions prior to depositing a 0.5 μl protein solution drop in the bottom of a crystallization chamber. Protein solutions were then covered with 40 μl of paraffin oil. The crystallization chambers were left unsealed to incubate at 20° C. Crystal growth was monitored daily.

Results

The dye added to, and present in, the protein solutions of the nanoliter volume crystallization trials conducted under oil did not appear to diffuse into the paraffin oil. The dye did not stain salt crystals formed during the trials, nor did the presence of the dye interfere with salt crystal formation. As a further control, a 0.5 μl drop of undiluted Izit under 40 μl of paraffin or Al's (Hampton Research) oil was allowed to incubate at 20° C. After 72 hours the dye did not appear to have diffused into the surrounding oils. Even after evaporation of the Al's oil, the blue dye remained in place. As further controls, four 0.5 μl samples of saturated NaCl solution were deposited into four separate containers. In three of these, crystallization trials were initiated with the addition of Izit in quantities of 1 part per 30 parts solution, 1 part per 60 parts solution, and 1 part per 100 parts solutions. Crystals of NaCl were formed under oil in both the absence and the presence of Izit. In none of the trials, under any of the dilutions tested, did the blue dye enter, and thereby color, the salt crystals. As reported, Izit itself will crystallize under conditions of high salt. When this occurs, the crystallized Izit form distinctive networks of blue fibers or sea urchin crystals. (Note: in Example Three, evidence is presented that suggests that other crystalline forms of Izit or dyed crystals of component(s) can occur. In particular, it is noted that sodium thiocyanate might form dyed crystals under particular conditions.)

For most proteins, the addition of dye to the protein samples tested did not interfere with crystal formation, and furthermore, resulted in the production of colored protein crystals, i.e. the dye was taken up by the protein crystals (Table 1; FIG. 1). For each test protein, equal volumes of sample and crystallization buffer were mixed. These crystallization samples were either taken as is, "neat," or Izit was added at a ratio of 1:30, 1:60, or 1:100 in respect to the crystallization sample volume. After preparation of the crystallization samples, the samples were deposited into the crystallization chambers as described in the Materials and Methods section. Crystal trial samples were then covered with 40 μl of paraffin oil and the experiments monitored for the formation of protein crystals. Seven out of ten test proteins crystallized in the absence of dye, specifically, lysozyme, thaumatin, cellulase, pepsin, trypsin, equine serum albumin and catalyse crystals formed in the absence of the blue dye. Each of these test proteins also crystallized in the presence of dye, but crystallization of only four definitively resulted in blue crystals, specifically, lysozyme, thaumatin, trypsin and equine serum albumin. Equine serum albumin displayed phase changes in the absence and presence of dye. Crystallization of cellulase resulted in small flat square plates that appeared to display staining intensity, but it was not possible to definitively characterize the cellulase crystals as blue due to the thinness of the resultant crystals and the resulting similarity of the coloration to the background. The color of cellulase crystals was similar to background hence it was not evident if these crystals absorbed the dye. In addition, characterization of the cellulase crystals was further complicated by their small size. The background intensity due to unincorporated dye present in each sample was similar for each protein tested. The amount of dye incorporated into the protein crystals, and therefore the intensity of resulting coloration, depended on the concentration of dye used and the number and size of the crystals (FIG. 1). The reason(s) for the inability of catalase and pepsin to form crystals in the presence of Izit are unknown. It is reasonable to postulate that the failure of catalase and pepsin crystals to form in the presence of Izit is only isolated to the single set of conditions used in this trial. As evidenced by the results when attempting to crystallize trypsin, alteration of the environmental conditions to which a protein solution is subjected can effect changes in the incorporation of dye into a protein crystal.

The addition of blue dye to micro and even nano crystallization trials under oil, or in a miniaturized crystallization condition screening device, such as a microarray, will provide significant savings in material, time and money. In large part, the savings result from the ability to determine that crystals formed in a miniaturized system, under a specific set of conditions, are protein crystals, without having to replicate the specific set of conditions on a larger scale, thereby negating much of the initial benefit of miniaturization. While this improved method of screening crystallization conditions is by no means a replacement for growing suitable sized crystals for analysis, it offers a significant improvement to the process of determining appropriate conditions to grow the suitable sized crystals required.

EXAMPLE TWO

Screening Crystallization Conditions for Crystallization of Selected Proteins from Protein Solutions Containing Izit Introduction The blue dye Izit facilitated the screening of crystallization conditions suitable for producing crystals of lysozyme, pepsin and β-lactoglobulin. The experimental design used in conjunction with the ability to detect nano-scale crystals, facilitated by the use of the dye, allowed 450 different sets of conditions to be screened. This set of trials, performed in duplicate and systematically screening 10 variables, consumed only a few micrograms of protein. Each crystallization variable was represented by several implementations. For example, the variable organic precipitant was represented by five levels: 1,2-methyl-2,4-pentanediol (MPD); 2, polyethylene glycol 400 (PEG400); 3, PEG2000; 4, PEG4000; and 5, PEG8000. This is in stark contrast to classical approaches normally used in crystallography that use tens of milligrams of protein to screen approximately 24–48 sets of conditions. The ease and economy in which protein crystallization conditions can be screened using these disclosed methods allows a thorough sampling of crystallization parameters for any given protein. This allows an investigator to readily identify conditions optimal for crystallization and can be used to determine conditions suitable for the growth of protein crystals of suitable size and quality for analysis and characterization.

Materials and Methods:

The proteins used as test proteins for this example were: hen egg white lysozyme (Boehringer Mannheim, 1243004), 30 mg/ml in 0.1 M sodium acetate (pH 4.7); porcine pepsin (Sigma, P6887), 60 mg/ml in 100 mM cacodylate buffer (pH 6.5), 0.2 M Ca acetate; bovine β-lactoglobulin (Sigma, L3908), 10 mg/ml in 100 mM Tris-HCl (pH 6.5). The concentrations and buffer solutions used for the nano crystallization screen are identical to those used in the 0.5 µl scale experiments described earlier. Prior to the initiation of the nano crystallization screen IZIT was added to each sample using a dilution of 1 part dye to 19 parts protein (v/v).

Paraffin oil and Izit were purchased from Hampton Research. Nanoliter crystallization screens were initiated by deploying various ratios of protein sample containing blue dye and crystallization buffer (described in Appendix One) into a chamber and then overlaying with 40 µl of Al's oil. The final volume of the experiments were 80 nl. The ratio of protein to precipitating buffer was either 1:2, 1:1, or 2:1. The exact composition of each of the 450 recipes used is recorded in the table of screen conditions (Appendix One). The pH of the recipes can be calculated using the Henderson-Hasselback equation. Unless otherwise indicated, the buffer components included in the crystallization trial condition recipes are the base (HEPES and MES). MPD and β-OG are 2-methyl-2,4-pentanediol and N-octyl-β-d-glu-ocpyranoside. PEG400, PEG2K, PEG4000 and PEG 8K are polyethylene glycols of indicated size/mass as is known to those of skill in the art.

The experimental nanoliter crystallization volumes were sealed during the trials. Data were collected four days after the initiation of the experiment and recorded. The results were scored by visual inspection.

Crystallization trials were conducted using the precipitant solutions described in Appendix one at the ratios indicated. 450 trial conditions, repeated in duplicate, were tested for each of the proteins. The total volume for each trial protein solution was 80 nanoliters at the beginning of the trial. Each volume of protein solution was overlayed with 40 µl of Al's oil. The crystallization chambers were sealed and left to incubate at 4° C. and 20° C. Crystal growth was recorded on the fourth day.

Results

Figure 2:
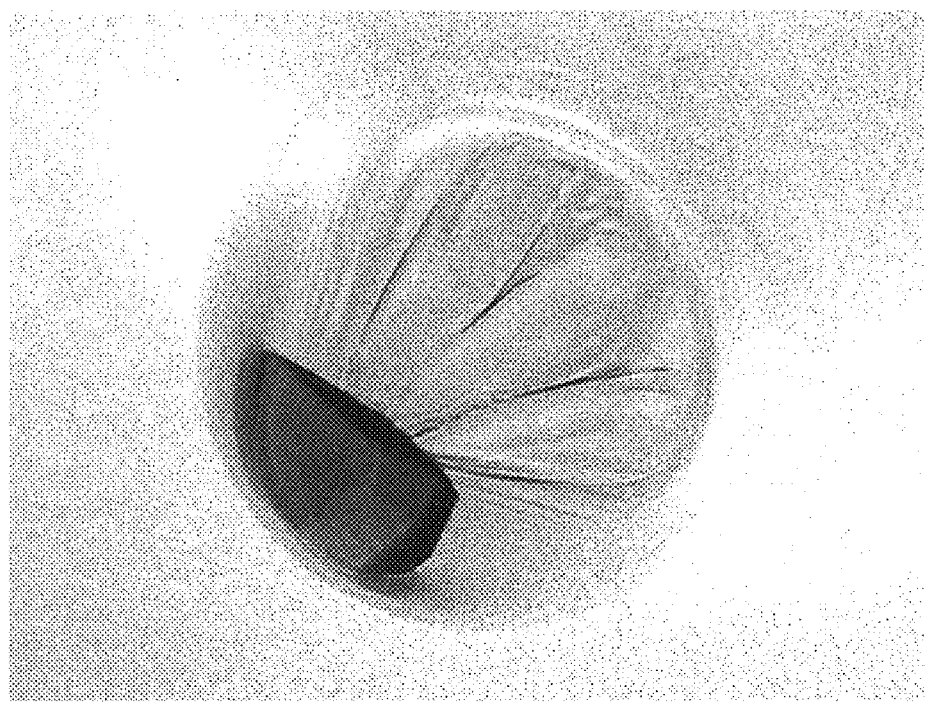
FIG. 2 depicts a lysozyme crystal. This dyed protein crystal, at the lower left quadrant of the well, was grown in the presence of Izit and has incorporated blue dye.
Figure 3:
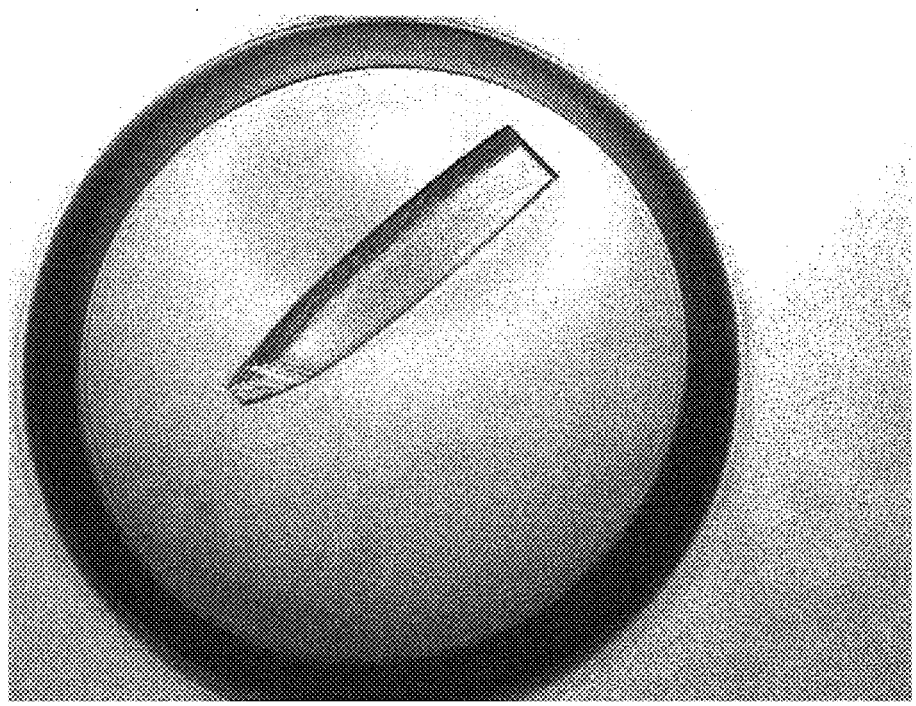
FIG. 3 depicts a pepsin crystal. This dyed protein crystal was grown in the presence of Izit and has incorporated blue dye.
Figure 4:
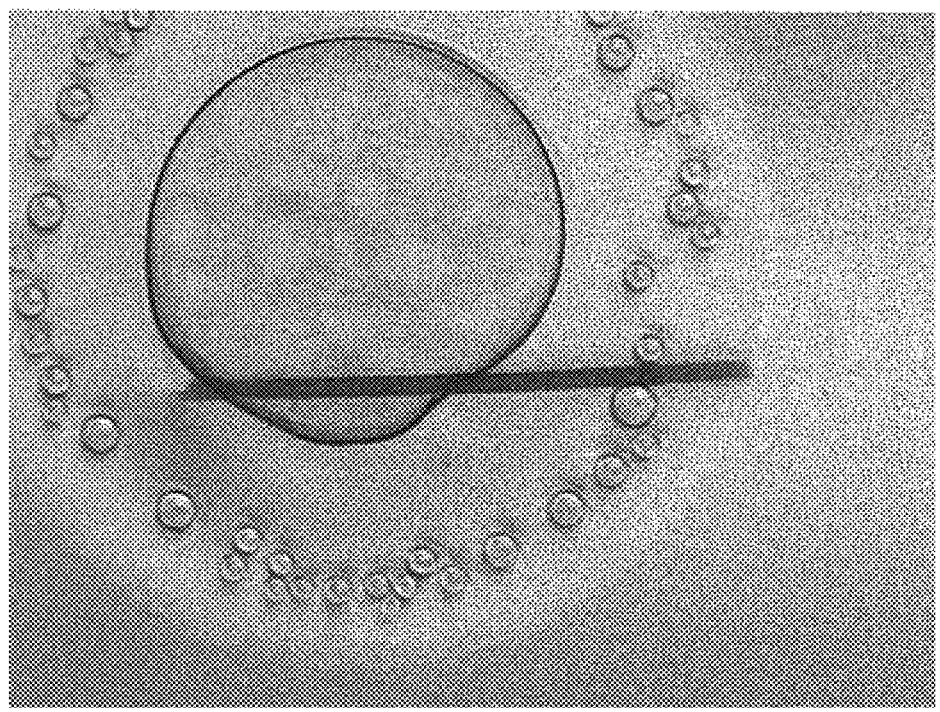
FIG. 4 depicts a β-lactoglobulin crystal. This dyed protein crystal was grown in the presence of Izit and has incorporated blue dye.

Conditions which promoted crystallization for each of the three proteins tested were identified. The numbers and types of crystals formed in the trials can be found in Table 2. For each of the three proteins, i.e., lysozyme, pepsin and β-lactoglobulin, there were 900 total trial results (450 trial screening conditions performed in duplicate). Results for each trial, i.e., each separate volume of protein solution, were analyzed and categorized. These categories include: (1) a clear drop, (2) phase separation, (3) precipitate (regular, granular), (4) microcrystals/precipitate, (5) rosettes or spherulites, (6) needles (one-dimensional growth), (7) plates (two-dimensional growth), (8) small crystals (three-dimensional growth of less than 0.2 mm) and (9) crystals (three-dimensional growth of greater than 0.2 mm). The categories or scores used for the nanoliter crystallization trials were adopted from those suggested by Hampton Research. Scoring of individual experiments to assign each to a category was performed by visual inspection. As the titles of the categories suggest, the results of each experiment were scored based upon presence or absence of detectable species and upon the species' morphology. For example, needle-like crystals are those appear to have one axis that is very long compared to the others, while plates have two axes of approximately equivalent size, each significantly larger than the third. A three dimensional crystal appears to have growth in three dimensions and looks like a brick. For the other categories, precipitate looks like sand, while both phase separations and rosettes look like mixtures of oil and water. The rosettes usually appear to have dense staining in their centers. In some instances, there is greater ambiguity as to the proper categorical assignment. In addition, the total number of trials in which blue crystals formed is also indicated. The number of blue crystals is calculated from visual inspection of categories 6–9, i.e., needles, plates, small three dimensional crystals and larger three dimensional crystals. A representative micrograph of blue crystals formed from each of the three proteins screened is shown in FIGS. 2–4. Specifically: FIG. 2 shows a blue lysozyme crystal grown in the presence of Izit using screening condition 361; FIG. 3 shows a blue pepsin crystal grown in the presence of Izit using screening condition 75; and FIG. 4 shows a blue β-lactoglobulin crystal grown in the presence of Izit using screening condition 213.

EXAMPLE THREE

Screening Crystallization Conditions for Crystallization of Selected Proteins from Protein Solutions Containing Izit and Controls Methods similar to those described in Example 2 were used to test the method of the invention using additional proteins and conditions. FIG. 5 shows micrographs of these trials wherein proteins, buffer, conditions and dye were varied in character and quantity. Trials were conducted as described before and using the noted screening Expt. #[Stock] conditions outlined in Appendix One. In the following example; T1=4° C., T2=15° C., and T3=22° C.

Crystallization conditions using Izit dye w/o any added protein were examined. For example, screening conditions 251 (at T3), 254 (at T3), 285 (at T2), 266 (at T3) and 339 (at T3) were conducted. Results from conditions 251, 285, 266, and 339 are shown in FIGS. 5A, B, C, and D, respectively. Condition 254, results not shown, resulted in no observable precipitation or crystallization. Condition 251 (FIG. 5A) also does not result in any observable crystal formation. However, condition 285, which includes acetate buffer at pH 4.5, 42 mM Ammonium Sulfate, 3.7% MPD, 1% glycerol and 2 mM magnesium chloride, and condition 339, which includes acetate buffer at pH 4.5, 460 mM thiocyanate, 0.8% PEG 8000, 0.5% glycerol and 8 mM arginine-HCl, both result in apparent crystals.

Crystallization conditions with various proteins were also examined. FIGS. 5E and 5F show results from β-lactoglobulin under conditions with phosphate buffer at pH 8 and with PEG 400 (at T1) and with phosphate buffer at pH 6, PEG 8000, 10% glycerol, 0.008 M Arg-HCl (at T3), respectively. FIGS. 5G, 5H, and 5I show results from myristol transferase under conditions 291 (at T3), 197 (at T2) and 259 (at T3), respectively. FIG. 5J shows results from pepsin under condition 347 (at T3). FIGS. 5K and 5L show results from Renac2 under conditions 41 (at T1) and 339 (at T3), respectively. FIGS. 5M and 5N show results from Rob1 under conditions 212 (at T2) and 337 (at T3), respectively. FIG. 5O shows results from B10 in acetate buffer at pH 4.5, with 450 mM thiocyanate, 0.8% PEG 8000, 0.5% glycerol and 8 mM arginine HCl (at T3).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

TABLE 1

Summary of IZIT Crystallization Results

| Protein | Neat | 1:30 | 1:60 | 1:100 | Condition | Initial pH |
|---|---|---|---|---|---|---|
| Lysozyme | Xtl | Bxtl | Bxtl | Bxtl | | 4.7 |
| Thaumatin | Xtl | Bxtl | Bxtl | Bxtl | HR | 6.5 |
| Catalase | Xtl | — | — | — | CS36 | 8.0 |
| Cellulase | Xtl | Xtl | Xtl | Xtl | | 8.5 |
| Pepsin | Xtl | — | — | — | | 6.5 |
| Equine serum albumin | Pc | BPc | BPc | BPc | | 5.5 |
| α-amylase | — | — | — | — | | 7.0 |
| β-amylase | — | — | — | — | | 7.5 |
| β-lactoglobulin | — | — | — | — | | 6.5 |
| Trypsin | Xtl | Bxtl | Bxtl | Bxtl | CS4 | 7.0 |
| Trypsin | Xtl | Xtl | Xtl | Xtl | CS15 | 7.0 |
| Typsin | Xtl | Bxtl | Bxtl | Bxtl | CS16 | 7.0 |
| Trypsin | Xtl | Xtl | Xtl | Xtl | CS20 | 7.0 |
| Trypsin | Xtl | Xtl | Xtl | Xtl | CS28 | 7.0 |
| Trypsin | Xtl | Xtl | Xtl | Xtl | CS30 | 7.0 |
| Trypsin | Xtl | Xtl | Xtl | Xtl | 31 | 7.0 |

Xtl = crystal, Bxtl = blue crystal, Pc = phase change, BPc = blue phase change, neat = absence of Izit in crystallization trial. Condition = the crystallization buffer used. CS = crystal screen. HR = Hampton Research web page http://www.hamptonresearch.com/.

TABLE 2A

Lysozyme

| Score[1] | Frequency |
|---|---|
| 1 | 795 |
| 2 | 58 |
| 3 | 17 |
| 4 | 3 |
| 5 | 1 |
| 6 | 4 |
| 7 | 1 |
| 8 | 21 |
| Number of blue crystals | 10 |

TABLE 2B

Pepsin

| Score[1] | Frequency |
|---|---|
| 1 | 591 |
| 2 | 24 |
| 3 | 30 |
| 4 | 9 |
| 5 | 0 |
| 6 | 25 |
| 7 | 164 |
| 8 | 57 |
| Number of blue crystals | 2 |

TABLE 2C

β-Lactoglobulin

| Score[1] | Frequency |
|---|---|
| 1 | 807 |
| 2 | 58 |
| 3 | 8 |
| 4 | 13 |
| 5 | 1 |
| 6 | 5 |
| 7 | 7 |
| 8 | 1 |
| Number of blue crystals | 5 |

1 Score Definitions

| Score | Score Descriptor |
|---|---|
| 1 | Clear Drop |
| 2 | Phase Separation |
| 3 | Precipitate (Regular Granular) |
| 4 | MicroCrystals / Precipitate |
| 5 | Rosettes or Spherulites |
| 6 | Needles (1D Growth) |
| 7 | Plates (2D Growth) |
| 8 | Crystals (3D Growth < 0.2 mm) |
| 9 | Crystals (3D Growth > 0.2 mm) |

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 1 | 62 | 0 | 9 | 0 | 0 | 0 | 0 | 40 | 203 | 0 | 0 | 0 | 0 | 0 | 0 | 0 | 31 | 41 | 614 | 1000 | 3 | 1 |
| 2 | 0 | 62 | 83 | 0 | 0 | 0 | 0 | 114 | 0 | 0 | 0 | 125 | 0 | 0 | 0 | 31 | 0 | 0 | 585 | 1000 | 3 | 1 |
| 3 | 62 | 0 | 11 | 48 | 0 | 0 | 0 | 0 | 0 | 0 | 0 | 0 | 240 | 0 | 0 | 0 | 31 | 41 | 552 | 1000 | 3 | 1 |
| 4 | 0 | 62 | 215 | 0 | 75 | 0 | 0 | 0 | 0 | 0 | 0 | 83 | 0 | 15 | 15 | 31 | 0 | 21 | 499 | 1000 | 3 | 1 |
| 5 | 62 | 0 | 151 | 0 | 0 | 152 | 0 | 0 | 14 | 83 | 0 | 0 | 0 | 0 | 15 | 0 | 3 | 41 | 566 | 1000 | 3 | 1 |
| 6 | 62 | 0 | 204 | 0 | 75 | 0 | 0 | 0 | 0 | 0 | 0 | 0 | 11 | 0 | 15 | 0 | 31 | 21 | 509 | 1000 | 3 | 1 |
| 7 | 0 | 62 | 7 | 121 | 0 | 0 | 0 | 0 | 0 | 0 | 0 | 0 | 0 | 0 | 0 | 0 | 31 | 41 | 729 | 1000 | 3 | 1 |
| 8 | 62 | 0 | 11 | 40 | 0 | 0 | 0 | 0 | 0 | 13 | 0 | 196 | 0 | 0 | 0 | 0 | 31 | 21 | 641 | 1000 | 3 | 1 |
| 9 | 62 | 0 | 4 | 115 | 0 | 0 | 0 | 0 | 0 | 0 | 0 | 0 | 127 | 0 | 0 | 31 | 31 | 21 | 626 | 1000 | 3 | 1 |
| 10 | 0 | 62 | 301 | 0 | 152 | 0 | 0 | 0 | 0 | 13 | 0 | 0 | 0 | 0 | 0 | 0 | 31 | 41 | 385 | 1000 | 3 | 1 |
| 11 | 0 | 62 | 51 | 0 | 0 | 39 | 149 | 0 | 0 | 0 | 0 | 194 | 0 | 15 | 0 | 0 | 31 | 0 | 608 | 1000 | 3 | 1 |
| 12 | 62 | 0 | 8 | 0 | 0 | 0 | 0 | 0 | 0 | 13 | 0 | 0 | 16 | 15 | 0 | 0 | 31 | 21 | 753 | 1000 | 3 | 1 |
| 13 | 0 | 62 | 11 | 182 | 0 | 0 | 0 | 0 | 0 | 0 | 0 | 0 | 0 | 15 | 0 | 0 | 0 | 21 | 694 | 1000 | 3 | 1 |
| 14 | 62 | 0 | 98 | 0 | 0 | 95 | 0 | 0 | 0 | 105 | 0 | 0 | 0 | 0 | 0 | 0 | 31 | 21 | 573 | 1000 | 3 | 1 |
| 15 | 0 | 62 | 4 | 0 | 0 | 0 | 182 | 48 | 0 | 0 | 16 | 0 | 0 | 15 | 0 | 0 | 0 | 0 | 701 | 1000 | 3 | 1 |
| 16 | 62 | 0 | 39 | 0 | 0 | 0 | 0 | 95 | 244 | 0 | 108 | 0 | 0 | 0 | 0 | 31 | 31 | 21 | 556 | 1000 | 3 | 1 |
| 17 | 0 | 62 | 94 | 0 | 0 | 0 | 0 | 181 | 16 | 0 | 0 | 0 | 0 | 0 | 0 | 0 | 31 | 21 | 591 | 1000 | 3 | 1 |
| 18 | 62 | 0 | 40 | 0 | 0 | 48 | 0 | 0 | 0 | 0 | 129 | 0 | 0 | 15 | 0 | 31 | 0 | 0 | 670 | 1000 | 3 | 1 |
| 19 | 62 | 0 | 43 | 0 | 0 | 0 | 0 | 114 | 0 | 0 | 0 | 235 | 0 | 0 | 0 | 0 | 31 | 0 | 566 | 1000 | 3 | 1 |
| 20 | 62 | 0 | 47 | 0 | 0 | 0 | 0 | 183 | 0 | 16 | 14 | 0 | 0 | 0 | 15 | 31 | 31 | 0 | 617 | 1000 | 3 | 1 |
| 21 | 62 | 0 | 7 | 0 | 0 | 0 | 0 | 0 | 0 | 0 | 0 | 0 | 0 | 0 | 0 | 31 | 31 | 41 | 661 | 1000 | 3 | 1 |
| 22 | 0 | 62 | 164 | 0 | 0 | 152 | 0 | 0 | 0 | 106 | 0 | 0 | 0 | 15 | 0 | 31 | 0 | 41 | 522 | 1000 | 3 | 1 |
| 23 | 62 | 0 | 3 | 0 | 0 | 0 | 96 | 0 | 0 | 197 | 0 | 0 | 0 | 0 | 15 | 31 | 0 | 41 | 661 | 1000 | 3 | 1 |
| 24 | 62 | 0 | 37 | 0 | 0 | 0 | 0 | 0 | 0 | 0 | 0 | 197 | 127 | 0 | 0 | 31 | 0 | 21 | 598 | 1000 | 3 | 1 |
| 26 | 0 | 62 | 3 | 40 | 0 | 0 | 0 | 0 | 0 | 0 | 0 | 0 | 106 | 15 | 0 | 0 | 31 | 41 | 611 | 1000 | 3 | 1 |
| 27 | 62 | 0 | 124 | 0 | 0 | 115 | 0 | 0 | 0 | 0 | 0 | 0 | 0 | 0 | 15 | 0 | 31 | 21 | 536 | 1000 | 3 | 1 |
| 28 | 0 | 62 | 105 | 96 | 0 | 96 | 0 | 0 | 0 | 106 | 0 | 0 | 0 | 0 | 0 | 0 | 0 | 41 | 590 | 1000 | 3 | 1 |
| 29 | 62 | 0 | 7 | 0 | 0 | 0 | 0 | 0 | 0 | 0 | 0 | 0 | 0 | 0 | 15 | 31 | 31 | 21 | 642 | 1000 | 3 | 1 |
| 30 | 62 | 0 | 17 | 116 | 0 | 0 | 0 | 0 | 0 | 0 | 0 | 0 | 0 | 0 | 0 | 31 | 0 | 41 | 672 | 1000 | 3 | 1 |
| 31 | 0 | 62 | 4 | 0 | 0 | 0 | 0 | 182 | 0 | 0 | 0 | 0 | 0 | 15 | 15 | 0 | 0 | 41 | 647 | 1000 | 3 | 1 |
| 32 | 62 | 0 | 4 | 0 | 0 | 0 | 181 | 0 | 131 | 0 | 0 | 0 | 16 | 0 | 0 | 0 | 0 | 0 | 738 | 1000 | 3 | 1 |
| 33 | 62 | 0 | 11 | 48 | 0 | 0 | 0 | 0 | 0 | 237 | 0 | 126 | 0 | 0 | 15 | 0 | 0 | 0 | 628 | 1000 | 3 | 1 |
| 34 | 0 | 62 | 7 | 0 | 0 | 0 | 115 | 0 | 0 | 0 | 0 | 0 | 0 | 0 | 0 | 0 | 31 | 21 | 639 | 1000 | 3 | 1 |
| 35 | 62 | 0 | 104 | 0 | 0 | 96 | 0 | 181 | 0 | 0 | 0 | 0 | 16 | 15 | 15 | 0 | 31 | 41 | 546 | 1000 | 3 | 1 |
| 36 | 62 | 0 | 127 | 0 | 0 | 0 | 0 | 152 | 0 | 13 | 0 | 16 | 0 | 0 | 0 | 31 | 31 | 0 | 584 | 1000 | 3 | 1 |
| 37 | 62 | 0 | 142 | 0 | 0 | 0 | 0 | 0 | 0 | 0 | 11 | 0 | 13 | 0 | 0 | 0 | 0 | 41 | 590 | 1000 | 3 | 1 |
| 38 | 0 | 62 | 130 | 0 | 0 | 149 | 0 | 0 | 85 | 0 | 0 | 0 | 0 | 15 | 15 | 31 | 31 | 0 | 615 | 1000 | 3 | 1 |
| 39 | 0 | 62 | 8 | 0 | 0 | 0 | 118 | 0 | 0 | 0 | 0 | 0 | 0 | 0 | 0 | 0 | 0 | 0 | 756 | 1000 | 3 | 1 |
| 40 | 62 | 0 | 87 | 0 | 0 | 75 | 0 | 151 | 0 | 0 | 0 | 0 | 0 | 15 | 0 | 31 | 0 | 21 | 655 | 1000 | 3 | 1 |
| 41 | 0 | 62 | 107 | 0 | 0 | 0 | 0 | 0 | 0 | 13 | 0 | 0 | 13 | 0 | 0 | 0 | 31 | 21 | 616 | 1000 | 3 | 1 |
| 42 | 0 | 62 | 8 | 0 | 0 | 0 | 151 | 0 | 0 | 0 | 0 | 0 | 0 | 15 | 0 | 31 | 31 | 21 | 700 | 1000 | 3 | 1 |

-continued

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 42 | 62 | 0 | 7 | 149 | 0 | 0 | 0 | 0 | 0 | 0 | 0 | 13 | 0 | 0 | 15 | 0 | 0 | 0 | 754 | 1000 | 3 | 1 |
| 43 | 0 | 62 | 92 | 0 | 31 | 0 | 0 | 0 | 0 | 158 | 0 | 0 | 0 | 0 | 15 | 0 | 31 | 21 | 592 | 1000 | 3 | 1 |
| 44 | 0 | 62 | 84 | 0 | 0 | 76 | 0 | 0 | 0 | 84 | 0 | 0 | 0 | 0 | 15 | 0 | 0 | 41 | 638 | 1000 | 3 | 1 |
| 45 | 62 | 0 | 11 | 0 | 0 | 0 | 75 | 0 | 0 | 0 | 0 | 83 | 0 | 15 | 0 | 31 | 0 | 21 | 702 | 1000 | 3 | 1 |
| 46 | 62 | 0 | 354 | 0 | 152 | 0 | 0 | 0 | 0 | 0 | 0 | 0 | 13 | 0 | 0 | 31 | 0 | 41 | 347 | 1000 | 3 | 1 |
| 47 | 0 | 62 | 12 | 0 | 0 | 0 | 48 | 0 | 0 | 0 | 245 | 0 | 0 | 0 | 0 | 31 | 31 | 21 | 546 | 1000 | 3 | 1 |
| 48 | 62 | 0 | 164 | 0 | 76 | 0 | 0 | 0 | 0 | 158 | 86 | 0 | 0 | 15 | 0 | 31 | 0 | 41 | 525 | 1000 | 3 | 1 |
| 49 | 62 | 0 | 9 | 0 | 0 | 0 | 0 | 32 | 0 | 0 | 0 | 0 | 0 | 15 | 0 | 31 | 0 | 41 | 668 | 1000 | 3 | 1 |
| 50 | 62 | 0 | 112 | 0 | 40 | 0 | 0 | 0 | 202 | 242 | 0 | 0 | 0 | 0 | 0 | 31 | 0 | 21 | 518 | 1000 | 3 | 1 |
| 51 | 0 | 73 | 151 | 0 | 49 | 0 | 0 | 0 | 0 | 0 | 150 | 0 | 0 | 0 | 0 | 0 | 36 | 0 | 449 | 1000 | 3 | 1 |
| 52 | 0 | 73 | 75 | 0 | 30 | 0 | 0 | 0 | 0 | 0 | 0 | 16 | 79 | 0 | 0 | 0 | 36 | 24 | 611 | 1000 | 3 | 1 |
| 53 | 73 | 0 | 197 | 0 | 72 | 0 | 0 | 0 | 0 | 0 | 0 | 0 | 0 | 0 | 18 | 0 | 36 | 48 | 477 | 1000 | 3 | 1 |
| 54 | 0 | 73 | 193 | 30 | 0 | 0 | 0 | 0 | 0 | 149 | 0 | 0 | 0 | 18 | 0 | 36 | 0 | 48 | 479 | 1000 | 3 | 1 |
| 55 | 73 | 0 | 9 | 49 | 0 | 185 | 0 | 0 | 0 | 0 | 0 | 0 | 0 | 0 | 0 | 36 | 36 | 0 | 655 | 1000 | 3 | 1 |
| 56 | 73 | 0 | 4 | 0 | 0 | 0 | 29 | 0 | 251 | 0 | 0 | 0 | 0 | 0 | 18 | 0 | 0 | 48 | 537 | 1000 | 3 | 1 |
| 57 | 0 | 73 | 9 | 95 | 0 | 0 | 0 | 0 | 0 | 0 | 0 | 0 | 145 | 0 | 0 | 36 | 0 | 48 | 690 | 1000 | 3 | 1 |
| 58 | 73 | 0 | 8 | 0 | 0 | 0 | 0 | 0 | 0 | 0 | 108 | 0 | 0 | 0 | 18 | 0 | 36 | 0 | 613 | 1000 | 3 | 1 |
| 59 | 73 | 0 | 18 | 0 | 0 | 0 | 0 | 29 | 106 | 0 | 148 | 0 | 0 | 0 | 0 | 36 | 0 | 48 | 696 | 1000 | 3 | 1 |
| 60 | 73 | 0 | 223 | 0 | 94 | 0 | 0 | 0 | 0 | 0 | 0 | 0 | 147 | 0 | 18 | 0 | 36 | 0 | 425 | 1000 | 3 | 1 |
| 61 | 0 | 73 | 87 | 0 | 30 | 114 | 0 | 0 | 0 | 10 | 0 | 0 | 0 | 0 | 0 | 0 | 0 | 24 | 640 | 1000 | 3 | 1 |
| 62 | 0 | 73 | 127 | 0 | 0 | 0 | 0 | 0 | 0 | 0 | 0 | 13 | 0 | 18 | 0 | 0 | 36 | 24 | 591 | 1000 | 3 | 1 |
| 63 | 0 | 73 | 4 | 151 | 49 | 0 | 0 | 0 | 0 | 0 | 0 | 244 | 0 | 18 | 0 | 36 | 0 | 48 | 674 | 1000 | 3 | 1 |
| 64 | 0 | 73 | 161 | 0 | 0 | 0 | 0 | 0 | 0 | 16 | 0 | 0 | 0 | 0 | 18 | 36 | 0 | 48 | 389 | 1000 | 3 | 1 |
| 65 | 73 | 0 | 13 | 188 | 0 | 0 | 119 | 0 | 0 | 0 | 0 | 130 | 0 | 18 | 0 | 0 | 36 | 0 | 652 | 1000 | 3 | 1 |
| 66 | 0 | 73 | 9 | 0 | 0 | 49 | 0 | 0 | 0 | 0 | 249 | 0 | 0 | 18 | 0 | 0 | 0 | 48 | 585 | 1000 | 3 | 1 |
| 67 | 0 | 73 | 53 | 0 | 49 | 0 | 0 | 0 | 13 | 0 | 0 | 0 | 246 | 0 | 18 | 0 | 36 | 24 | 533 | 1000 | 3 | 1 |
| 68 | 0 | 73 | 143 | 0 | 0 | 0 | 148 | 0 | 0 | 13 | 0 | 0 | 10 | 18 | 18 | 0 | 0 | 48 | 423 | 1000 | 3 | 1 |
| 69 | 73 | 0 | 4 | 0 | 0 | 0 | 112 | 0 | 0 | 0 | 0 | 129 | 13 | 0 | 18 | 36 | 0 | 0 | 744 | 1000 | 3 | 1 |
| 70 | 0 | 73 | 13 | 0 | 0 | 0 | 0 | 118 | 0 | 0 | 0 | 196 | 0 | 0 | 18 | 0 | 36 | 24 | 714 | 1000 | 3 | 1 |
| 71 | 73 | 0 | 8 | 149 | 0 | 0 | 0 | 0 | 0 | 0 | 0 | 0 | 77 | 18 | 0 | 36 | 0 | 24 | 678 | 1000 | 3 | 1 |
| 72 | 73 | 0 | 49 | 0 | 40 | 111 | 0 | 0 | 0 | 0 | 0 | 0 | 0 | 0 | 18 | 0 | 36 | 24 | 607 | 1000 | 3 | 1 |
| 73 | 0 | 73 | 132 | 0 | 0 | 0 | 0 | 0 | 0 | 104 | 0 | 0 | 0 | 18 | 0 | 73 | 0 | 48 | 457 | 1000 | 3 | 1 |
| 74 | 0 | 73 | 120 | 0 | 0 | 0 | 70 | 0 | 13 | 0 | 10 | 0 | 0 | 0 | 18 | 0 | 36 | 0 | 669 | 1000 | 3 | 1 |
| 75 | 73 | 0 | 4 | 94 | 0 | 0 | 0 | 0 | 0 | 0 | 0 | 0 | 0 | 18 | 0 | 0 | 36 | 24 | 646 | 1000 | 3 | 1 |
| 76 | 0 | 73 | 14 | 0 | 0 | 0 | 0 | 0 | 0 | 0 | 0 | 0 | 77 | 0 | 0 | 36 | 0 | 48 | 730 | 1000 | 3 | 1 |
| 77 | 73 | 0 | 132 | 0 | 0 | 151 | 0 | 0 | 13 | 0 | 0 | 0 | 0 | 18 | 0 | 36 | 36 | 24 | 529 | 1000 | 3 | 1 |
| 78 | 73 | 0 | 116 | 0 | 0 | 112 | 0 | 0 | 0 | 0 | 0 | 130 | 0 | 0 | 18 | 0 | 0 | 48 | 611 | 1000 | 3 | 1 |
| 79 | 73 | 0 | 6 | 0 | 49 | 0 | 0 | 118 | 0 | 0 | 107 | 0 | 0 | 0 | 0 | 36 | 0 | 0 | 649 | 1000 | 3 | 1 |
| 80 | 73 | 0 | 14 | 0 | 0 | 0 | 70 | 94 | 79 | 0 | 0 | 0 | 0 | 18 | 0 | 0 | 0 | 24 | 689 | 1000 | 3 | 1 |
| 81 | 0 | 73 | 9 | 0 | 0 | 0 | 0 | 0 | 17 | 0 | 0 | 0 | 0 | 0 | 18 | 0 | 36 | 0 | 733 | 1000 | 3 | 1 |
| 82 | 73 | 0 | 4 | 188 | 0 | 0 | 0 | 0 | 0 | 0 | 0 | 0 | 13 | 0 | 0 | 0 | 0 | 24 | 678 | 1000 | 3 | 1 |
| 83 | 73 | 0 | 129 | 0 | 0 | 148 | 0 | 0 | 0 | 0 | 0 | 0 | 0 | 0 | 0 | 36 | 0 | 0 | 601 | 1000 | 3 | 1 |

-continued

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 84 | 0 | 73 | 4 | 0 | 0 | 0 | 39 | 0 | 0 | 0 | 200 | 0 | 0 | 18 | 0 | 0 | 36 | 24 | 605 | 1000 | 3 | 1 |
| 85 | 0 | 73 | 14 | 30 | 0 | 0 | 0 | 0 | 0 | 149 | 0 | 0 | 0 | 0 | 0 | 36 | 0 | 48 | 650 | 1000 | 3 | 1 |
| 86 | 73 | 0 | 75 | 0 | 30 | 0 | 0 | 0 | 0 | 0 | 0 | 0 | 147 | 0 | 0 | 0 | 0 | 24 | 651 | 1000 | 3 | 1 |
| 87 | 73 | 0 | 19 | 0 | 0 | 0 | 0 | 39 | 198 | 0 | 0 | 0 | 0 | 0 | 0 | 0 | 0 | 0 | 671 | 1000 | 3 | 1 |
| 88 | 73 | 0 | 42 | 0 | 0 | 30 | 0 | 0 | 0 | 0 | 0 | 148 | 0 | 0 | 0 | 0 | 0 | 48 | 604 | 1000 | 3 | 1 |
| 89 | 0 | 73 | 158 | 0 | 49 | 0 | 0 | 0 | 0 | 0 | 0 | 0 | 242 | 0 | 18 | 36 | 0 | 0 | 442 | 1000 | 3 | 1 |
| 90 | 73 | 0 | 89 | 0 | 30 | 0 | 0 | 0 | 152 | 0 | 0 | 0 | 0 | 0 | 0 | 36 | 0 | 48 | 553 | 1000 | 3 | 1 |
| 91 | 0 | 73 | 14 | 0 | 0 | 72 | 0 | 0 | 0 | 0 | 134 | 0 | 0 | 0 | 0 | 36 | 36 | 48 | 576 | 1000 | 3 | 1 |
| 92 | 73 | 0 | 65 | 0 | 49 | 0 | 0 | 0 | 81 | 145 | 0 | 0 | 0 | 0 | 18 | 0 | 0 | 24 | 625 | 1000 | 3 | 1 |
| 93 | 0 | 73 | 152 | 119 | 0 | 0 | 0 | 0 | 0 | 0 | 0 | 0 | 244 | 0 | 0 | 36 | 0 | 0 | 403 | 1000 | 3 | 1 |
| 94 | 73 | 0 | 9 | 0 | 94 | 0 | 0 | 0 | 106 | 0 | 0 | 0 | 0 | 0 | 0 | 0 | 0 | 0 | 744 | 1000 | 3 | 1 |
| 95 | 73 | 0 | 203 | 29 | 0 | 0 | 0 | 186 | 0 | 0 | 17 | 0 | 0 | 0 | 18 | 0 | 36 | 24 | 463 | 1000 | 3 | 1 |
| 96 | 73 | 0 | 43 | 0 | 0 | 0 | 0 | 0 | 0 | 0 | 0 | 0 | 129 | 0 | 0 | 0 | 36 | 24 | 620 | 1000 | 3 | 1 |
| 97 | 0 | 73 | 9 | 0 | 0 | 0 | 117 | 0 | 0 | 0 | 0 | 0 | 0 | 0 | 18 | 36 | 0 | 0 | 618 | 1000 | 3 | 1 |
| 98 | 73 | 0 | 14 | 0 | 0 | 0 | 148 | 0 | 13 | 0 | 0 | 10 | 0 | 0 | 0 | 0 | 0 | 0 | 753 | 1000 | 3 | 1 |
| 99 | 73 | 0 | 13 | 0 | 0 | 148 | 49 | 0 | 0 | 246 | 0 | 0 | 0 | 0 | 18 | 0 | 0 | 0 | 516 | 1000 | 3 | 1 |
| 100 | 0 | 0 | 148 | 0 | 0 | 0 | 0 | 0 | 13 | 0 | 0 | 0 | 0 | 0 | 0 | 36 | 0 | 48 | 582 | 1000 | 2 | 1 |
| 101 | 0 | 100 | 203 | 0 | 0 | 0 | 0 | 214 | 0 | 19 | 0 | 0 | 0 | 0 | 0 | 0 | 0 | 0 | 464 | 1000 | 2 | 2 |
| 102 | 0 | 100 | 6 | 167 | 0 | 0 | 0 | 0 | 292 | 0 | 15 | 0 | 117 | 25 | 0 | 50 | 0 | 67 | 570 | 1000 | 2 | 2 |
| 103 | 0 | 100 | 33 | 0 | 0 | 0 | 0 | 31 | 0 | 0 | 156 | 0 | 0 | 0 | 0 | 50 | 0 | 67 | 554 | 1000 | 2 | 2 |
| 104 | 0 | 100 | 50 | 0 | 0 | 0 | 0 | 114 | 0 | 0 | 0 | 10 | 0 | 0 | 0 | 0 | 50 | 33 | 643 | 1000 | 2 | 2 |
| 105 | 0 | 100 | 21 | 0 | 0 | 0 | 0 | 167 | 0 | 0 | 15 | 0 | 0 | 0 | 0 | 0 | 50 | 67 | 580 | 1000 | 2 | 2 |
| 106 | 100 | 0 | 322 | 0 | 106 | 0 | 0 | 0 | 0 | 0 | 0 | 0 | 0 | 25 | 0 | 0 | 0 | 67 | 289 | 1000 | 2 | 2 |
| 107 | 100 | 0 | 54 | 0 | 0 | 57 | 0 | 0 | 0 | 78 | 0 | 0 | 0 | 0 | 0 | 0 | 0 | 67 | 405 | 1000 | 2 | 2 |
| 108 | 100 | 0 | 76 | 0 | 0 | 71 | 0 | 0 | 0 | 0 | 153 | 0 | 0 | 25 | 0 | 0 | 50 | 67 | 649 | 1000 | 2 | 2 |
| 109 | 100 | 0 | 7 | 0 | 0 | 0 | 0 | 0 | 0 | 0 | 156 | 116 | 0 | 0 | 0 | 0 | 0 | 0 | 555 | 1000 | 2 | 2 |
| 110 | 100 | 0 | 61 | 0 | 0 | 44 | 0 | 106 | 224 | 0 | 0 | 0 | 0 | 0 | 0 | 0 | 0 | 0 | 454 | 1000 | 2 | 2 |
| 111 | 100 | 0 | 18 | 0 | 0 | 0 | 135 | 0 | 0 | 0 | 0 | 0 | 0 | 0 | 25 | 50 | 0 | 67 | 544 | 1000 | 2 | 2 |
| 112 | 100 | 0 | 6 | 0 | 0 | 0 | 31 | 57 | 0 | 0 | 0 | 0 | 0 | 0 | 0 | 50 | 0 | 0 | 641 | 1000 | 2 | 2 |
| 113 | 100 | 0 | 27 | 0 | 138 | 0 | 0 | 0 | 289 | 0 | 0 | 0 | 0 | 0 | 25 | 0 | 0 | 33 | 443 | 1000 | 2 | 2 |
| 114 | 100 | 0 | 296 | 0 | 43 | 0 | 0 | 0 | 156 | 0 | 0 | 0 | 216 | 0 | 0 | 50 | 0 | 67 | 194 | 1000 | 2 | 2 |
| 115 | 100 | 0 | 129 | 0 | 0 | 0 | 167 | 0 | 0 | 0 | 0 | 0 | 15 | 0 | 25 | 0 | 0 | 33 | 403 | 1000 | 2 | 2 |
| 116 | 100 | 0 | 18 | 0 | 0 | 0 | 0 | 0 | 0 | 0 | 0 | 10 | 0 | 25 | 0 | 50 | 50 | 67 | 559 | 1000 | 2 | 2 |
| 117 | 100 | 0 | 11 | 114 | 0 | 0 | 0 | 0 | 0 | 0 | 0 | 0 | 0 | 0 | 25 | 50 | 0 | 33 | 655 | 1000 | 2 | 2 |
| 118 | 100 | 0 | 5 | 104 | 0 | 0 | 0 | 0 | 19 | 115 | 0 | 0 | 0 | 0 | 0 | 0 | 50 | 33 | 567 | 1000 | 2 | 2 |
| 119 | 0 | 100 | 6 | 218 | 0 | 0 | 0 | 43 | 221 | 0 | 0 | 0 | 0 | 0 | 0 | 0 | 0 | 67 | 565 | 1000 | 2 | 2 |
| 120 | 0 | 100 | 41 | 0 | 0 | 0 | 0 | 0 | 0 | 0 | 154 | 0 | 0 | 25 | 25 | 50 | 0 | 33 | 511 | 1000 | 2 | 2 |
| 121 | 100 | 0 | 18 | 0 | 0 | 0 | 136 | 0 | 289 | 0 | 0 | 0 | 0 | 0 | 0 | 50 | 0 | 33 | 483 | 1000 | 2 | 2 |
| 122 | 100 | 0 | 163 | 0 | 57 | 218 | 0 | 0 | 0 | 0 | 0 | 0 | 0 | 25 | 25 | 50 | 0 | 67 | 282 | 1000 | 2 | 2 |
| 123 | 100 | 0 | 232 | 0 | 0 | 108 | 0 | 0 | 0 | 0 | 0 | 116 | 19 | 0 | 0 | 0 | 50 | 33 | 339 | 1000 | 2 | 2 |
| 124 | 100 | 0 | 111 | 0 | 0 | 0 | 0 | 0 | 0 | 0 | 0 | 0 | 0 | 0 | 0 | 50 | 50 | 67 | 426 | 1000 | 2 | 2 |
| 125 | 0 | 100 | 163 | 0 | 0 | 0 | 0 | 167 | 15 | 0 | 0 | 0 | 0 | 0 | 25 | 0 | 0 | 67 | 438 | 1000 | 2 | 2 |

-continued

| Expt # (Stock) | 1 MES [0.5M] | 4 HEPE [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 126 | 0 | 100 | 41 | 0 | 0 | 0 | 0 | 43 | 218 | 0 | 0 | 0 | 0 | 0 | 0 | 0 | 50 | 0 | 548 | 1000 | 2 | 2 |
| 127 | 100 | 0 | 53 | 0 | 0 | 44 | 0 | 0 | 0 | 0 | 224 | 0 | 0 | 25 | 0 | 50 | 0 | 67 | 437 | 1000 | 2 | 2 |
| 128 | 0 | 100 | 19 | 0 | 0 | 0 | 56 | 0 | 0 | 0 | 287 | 0 | 0 | 25 | 0 | 0 | 0 | 0 | 513 | 1000 | 2 | 2 |
| 129 | 100 | 0 | 37 | 0 | 57 | 0 | 0 | 116 | 0 | 0 | 0 | 10 | 0 | 0 | 0 | 50 | 0 | 67 | 620 | 1000 | 2 | 2 |
| 130 | 100 | 0 | 142 | 0 | 138 | 0 | 0 | 0 | 0 | 152 | 0 | 151 | 0 | 0 | 25 | 0 | 50 | 67 | 266 | 1000 | 2 | 2 |
| 131 | 0 | 100 | 429 | 0 | 31 | 0 | 0 | 0 | 0 | 0 | 117 | 0 | 0 | 25 | 0 | 50 | 50 | 67 | 40 | 1000 | 2 | 2 |
| 132 | 100 | 0 | 96 | 0 | 103 | 0 | 0 | 0 | 0 | 0 | 156 | 0 | 0 | 0 | 25 | 0 | 0 | 67 | 479 | 1000 | 2 | 2 |
| 133 | 0 | 100 | 294 | 0 | 0 | 0 | 0 | 0 | 292 | 0 | 0 | 0 | 0 | 0 | 25 | 50 | 0 | 0 | 311 | 1000 | 2 | 2 |
| 134 | 100 | 0 | 18 | 138 | 0 | 0 | 0 | 0 | 19 | 0 | 0 | 81 | 0 | 25 | 0 | 0 | 50 | 67 | 497 | 1000 | 2 | 2 |
| 135 | 0 | 100 | 6 | 57 | 0 | 0 | 0 | 214 | 292 | 0 | 0 | 0 | 0 | 0 | 0 | 50 | 0 | 0 | 428 | 1000 | 2 | 2 |
| 136 | 100 | 0 | 88 | 0 | 0 | 0 | 73 | 0 | 19 | 0 | 15 | 0 | 0 | 0 | 0 | 0 | 50 | 67 | 579 | 1000 | 2 | 2 |
| 137 | 100 | 0 | 11 | 0 | 0 | 167 | 0 | 0 | 0 | 19 | 0 | 0 | 0 | 25 | 0 | 50 | 0 | 67 | 593 | 1000 | 2 | 2 |
| 138 | 0 | 100 | 172 | 0 | 0 | 0 | 0 | 216 | 0 | 0 | 0 | 10 | 0 | 0 | 0 | 50 | 0 | 0 | 429 | 1000 | 2 | 2 |
| 139 | 100 | 0 | 24 | 0 | 0 | 43 | 0 | 0 | 0 | 218 | 0 | 0 | 0 | 0 | 0 | 50 | 50 | 33 | 558 | 1000 | 2 | 2 |
| 140 | 100 | 0 | 11 | 116 | 0 | 0 | 0 | 0 | 19 | 0 | 0 | 0 | 0 | 25 | 0 | 0 | 0 | 67 | 621 | 1000 | 2 | 2 |
| 141 | 100 | 0 | 52 | 0 | 216 | 0 | 0 | 0 | 0 | 0 | 0 | 0 | 0 | 25 | 0 | 50 | 50 | 33 | 480 | 1000 | 2 | 2 |
| 142 | 0 | 100 | 662 | 0 | 0 | 0 | 116 | 0 | 0 | 0 | 10 | 0 | 0 | 0 | 25 | 50 | 0 | 67 | 81 | 1000 | 2 | 2 |
| 143 | 100 | 0 | 11 | 0 | 0 | 136 | 0 | 0 | 0 | 0 | 0 | 150 | 0 | 0 | 0 | 50 | 0 | 33 | 621 | 1000 | 2 | 2 |
| 144 | 100 | 0 | 140 | 0 | 114 | 0 | 112 | 0 | 0 | 0 | 0 | 10 | 0 | 25 | 0 | 0 | 50 | 33 | 365 | 1000 | 2 | 2 |
| 145 | 0 | 100 | 347 | 0 | 0 | 0 | 138 | 0 | 0 | 0 | 0 | 10 | 0 | 0 | 25 | 0 | 0 | 33 | 345 | 1000 | 2 | 2 |
| 146 | 0 | 100 | 6 | 0 | 0 | 30 | 0 | 0 | 0 | 0 | 0 | 0 | 152 | 25 | 0 | 0 | 50 | 0 | 697 | 1000 | 2 | 2 |
| 147 | 100 | 0 | 5 | 0 | 0 | 116 | 0 | 0 | 0 | 0 | 0 | 10 | 147 | 0 | 0 | 50 | 0 | 67 | 488 | 1000 | 2 | 2 |
| 148 | 0 | 100 | 49 | 0 | 0 | 43 | 0 | 0 | 0 | 0 | 0 | 0 | 0 | 25 | 0 | 0 | 50 | 0 | 675 | 1000 | 2 | 2 |
| 149 | 100 | 0 | 129 | 0 | 0 | 48 | 0 | 0 | 0 | 0 | 219 | 0 | 0 | 0 | 0 | 0 | 0 | 67 | 553 | 1000 | 2 | 2 |
| 150 | 100 | 0 | 60 | 0 | 0 | 0 | 0 | 0 | 0 | 238 | 0 | 0 | 0 | 25 | 0 | 50 | 0 | 0 | 528 | 1000 | 2 | 2 |
| 151 | 0 | 62 | 51 | 0 | 0 | 0 | 118 | 40 | 0 | 0 | 202 | 0 | 13 | 0 | 15 | 31 | 31 | 33 | 534 | 1000 | 3 | 1 |
| 152 | 62 | 0 | 4 | 0 | 0 | 0 | 118 | 0 | 0 | 0 | 0 | 0 | 0 | 0 | 0 | 31 | 31 | 21 | 642 | 1000 | 3 | 1 |
| 153 | 62 | 0 | 3 | 0 | 0 | 0 | 0 | 0 | 0 | 0 | 16 | 0 | 0 | 15 | 0 | 0 | 0 | 0 | 776 | 1000 | 3 | 1 |
| 154 | 62 | 0 | 191 | 0 | 0 | 183 | 0 | 0 | 131 | 197 | 0 | 0 | 0 | 15 | 0 | 31 | 0 | 41 | 492 | 1000 | 3 | 1 |
| 155 | 62 | 0 | 7 | 151 | 0 | 0 | 118 | 0 | 0 | 0 | 0 | 0 | 0 | 0 | 15 | 31 | 31 | 21 | 613 | 1000 | 3 | 1 |
| 156 | 62 | 0 | 12 | 0 | 0 | 0 | 40 | 0 | 0 | 0 | 0 | 0 | 0 | 15 | 0 | 0 | 31 | 0 | 623 | 1000 | 3 | 1 |
| 157 | 0 | 62 | 11 | 0 | 0 | 0 | 0 | 0 | 11 | 0 | 11 | 16 | 0 | 15 | 0 | 31 | 0 | 41 | 728 | 1000 | 3 | 1 |
| 158 | 62 | 0 | 361 | 0 | 121 | 0 | 121 | 0 | 0 | 0 | 0 | 0 | 0 | 0 | 0 | 0 | 0 | 41 | 708 | 1000 | 3 | 1 |
| 159 | 62 | 0 | 7 | 0 | 0 | 0 | 181 | 0 | 245 | 0 | 0 | 83 | 0 | 0 | 15 | 31 | 31 | 0 | 359 | 1000 | 3 | 1 |
| 160 | 62 | 0 | 4 | 0 | 0 | 0 | 48 | 0 | 0 | 0 | 0 | 16 | 0 | 0 | 0 | 0 | 0 | 41 | 689 | 1000 | 3 | 1 |
| 161 | 0 | 62 | 236 | 0 | 75 | 0 | 0 | 0 | 84 | 0 | 0 | 83 | 0 | 15 | 0 | 31 | 0 | 41 | 600 | 1000 | 3 | 1 |
| 162 | 62 | 0 | 202 | 0 | 75 | 0 | 0 | 0 | 131 | 0 | 0 | 0 | 0 | 0 | 15 | 31 | 31 | 21 | 478 | 1000 | 3 | 1 |
| 163 | 62 | 0 | 12 | 116 | 0 | 0 | 0 | 0 | 0 | 158 | 0 | 0 | 0 | 15 | 0 | 0 | 31 | 0 | 532 | 1000 | 3 | 1 |
| 164 | 0 | 62 | 101 | 0 | 32 | 0 | 0 | 0 | 0 | 156 | 0 | 0 | 0 | 0 | 0 | 0 | 0 | 41 | 624 | 1000 | 3 | 1 |
| 165 | 62 | 0 | 16 | 0 | 0 | 0 | 0 | 31 | 0 | 0 | 0 | 0 | 0 | 0 | 0 | 31 | 31 | 21 | 578 | 1000 | 3 | 1 |
| 166 | 62 | 0 | 4 | 0 | 0 | 0 | 0 | 0 | 0 | 0 | 0 | 0 | 0 | 0 | 15 | 31 | 0 | 41 | 714 | 1000 | 3 | 1 |
| 167 | 62 | 0 | 4 | 114 | 0 | 0 | 0 | 0 | 0 | 0 | 0 | 125 | 0 | 0 | 0 | 0 | 31 | 0 | 665 | 1000 | 3 | 1 |

-continued

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 168 | 0 | 62 | 123 | 0 | 0 | 116 | 0 | 0 | 0 | 128 | 0 | 0 | 0 | 0 | 15 | 0 | 0 | 41 | 515 | 1000 | 3 | 1 |
| 169 | 62 | 0 | 11 | 31 | 0 | 0 | 0 | 0 | 0 | 0 | 158 | 0 | 0 | 0 | 15 | 0 | 31 | 0 | 692 | 1000 | 3 | 1 |
| 170 | 0 | 62 | 12 | 0 | 0 | 0 | 94 | 0 | 0 | 0 | 0 | 104 | 0 | 15 | 0 | 31 | 0 | 0 | 683 | 1000 | 3 | 1 |
| 171 | 0 | 62 | 12 | 95 | 0 | 0 | 0 | 0 | 0 | 0 | 0 | 0 | 105 | 0 | 0 | 0 | 0 | 21 | 660 | 1000 | 3 | 1 |
| 172 | 0 | 62 | 12 | 0 | 0 | 0 | 75 | 0 | 0 | 83 | 0 | 0 | 0 | 0 | 0 | 0 | 0 | 0 | 770 | 1000 | 3 | 1 |
| 173 | 0 | 62 | 55 | 0 | 0 | 48 | 0 | 0 | 242 | 0 | 0 | 0 | 0 | 0 | 0 | 0 | 31 | 0 | 548 | 1000 | 3 | 1 |
| 174 | 0 | 62 | 357 | 0 | 119 | 0 | 0 | 0 | 11 | 0 | 0 | 0 | 0 | 15 | 0 | 0 | 0 | 21 | 431 | 1000 | 3 | 1 |
| 175 | 0 | 62 | 8 | 119 | 0 | 0 | 0 | 0 | 11 | 0 | 0 | 0 | 0 | 0 | 0 | 0 | 31 | 21 | 734 | 1000 | 3 | 1 |
| 176 | 62 | 0 | 104 | 0 | 48 | 0 | 0 | 0 | 0 | 0 | 0 | 0 | 0 | 15 | 0 | 0 | 31 | 0 | 520 | 1000 | 3 | 1 |
| 177 | 0 | 62 | 8 | 0 | 0 | 0 | 152 | 0 | 14 | 0 | 0 | 0 | 0 | 0 | 0 | 0 | 0 | 41 | 693 | 1000 | 3 | 1 |
| 178 | 62 | 0 | 179 | 0 | 75 | 0 | 0 | 0 | 85 | 0 | 0 | 0 | 0 | 0 | 15 | 0 | 0 | 21 | 563 | 1000 | 3 | 1 |
| 179 | 0 | 62 | 8 | 75 | 0 | 0 | 0 | 0 | 0 | 0 | 84 | 0 | 0 | 15 | 0 | 0 | 31 | 0 | 726 | 1000 | 3 | 1 |
| 180 | 62 | 0 | 296 | 0 | 149 | 0 | 0 | 0 | 0 | 0 | 0 | 13 | 0 | 0 | 0 | 0 | 31 | 0 | 434 | 1000 | 3 | 1 |
| 181 | 0 | 62 | 157 | 0 | 0 | 149 | 0 | 0 | 0 | 0 | 0 | 0 | 13 | 15 | 0 | 0 | 0 | 21 | 588 | 1000 | 3 | 1 |
| 182 | 62 | 0 | 97 | 0 | 40 | 0 | 0 | 31 | 0 | 0 | 0 | 0 | 197 | 0 | 0 | 0 | 31 | 0 | 537 | 1000 | 3 | 1 |
| 183 | 0 | 62 | 28 | 0 | 0 | 0 | 0 | 40 | 203 | 0 | 0 | 0 | 155 | 15 | 0 | 31 | 0 | 21 | 694 | 1000 | 3 | 1 |
| 184 | 0 | 62 | 46 | 0 | 0 | 0 | 0 | 0 | 0 | 0 | 0 | 0 | 0 | 15 | 0 | 0 | 31 | 41 | 577 | 1000 | 3 | 1 |
| 185 | 62 | 0 | 204 | 0 | 95 | 0 | 0 | 0 | 0 | 83 | 0 | 0 | 105 | 0 | 0 | 31 | 0 | 21 | 467 | 1000 | 3 | 1 |
| 186 | 62 | 0 | 85 | 0 | 0 | 75 | 0 | 0 | 108 | 0 | 0 | 0 | 0 | 0 | 15 | 0 | 0 | 41 | 643 | 1000 | 3 | 1 |
| 187 | 0 | 62 | 12 | 95 | 0 | 0 | 0 | 0 | 131 | 0 | 0 | 0 | 0 | 0 | 0 | 31 | 0 | 21 | 657 | 1000 | 3 | 1 |
| 188 | 62 | 0 | 307 | 0 | 116 | 0 | 0 | 0 | 0 | 0 | 0 | 0 | 106 | 15 | 0 | 31 | 0 | 41 | 313 | 1000 | 3 | 1 |
| 189 | 0 | 62 | 94 | 0 | 0 | 0 | 0 | 96 | 131 | 0 | 0 | 0 | 0 | 0 | 0 | 0 | 0 | 21 | 601 | 1000 | 3 | 1 |
| 190 | 62 | 0 | 3 | 116 | 0 | 0 | 0 | 75 | 0 | 0 | 85 | 0 | 0 | 0 | 15 | 31 | 0 | 41 | 632 | 1000 | 3 | 1 |
| 191 | 62 | 0 | 5 | 0 | 0 | 0 | 0 | 121 | 11 | 0 | 0 | 0 | 11 | 0 | 0 | 31 | 0 | 41 | 722 | 1000 | 3 | 1 |
| 192 | 0 | 62 | 87 | 0 | 0 | 94 | 0 | 0 | 0 | 0 | 107 | 0 | 0 | 15 | 0 | 31 | 0 | 21 | 679 | 1000 | 3 | 1 |
| 193 | 62 | 0 | 98 | 0 | 0 | 0 | 0 | 181 | 0 | 0 | 0 | 0 | 0 | 0 | 0 | 31 | 0 | 0 | 594 | 1000 | 3 | 1 |
| 194 | 0 | 62 | 7 | 0 | 0 | 0 | 0 | 152 | 14 | 0 | 0 | 0 | 16 | 15 | 0 | 0 | 31 | 41 | 705 | 1000 | 3 | 1 |
| 195 | 62 | 0 | 62 | 0 | 0 | 0 | 39 | 0 | 0 | 0 | 0 | 0 | 0 | 0 | 0 | 31 | 0 | 21 | 670 | 1000 | 3 | 1 |
| 196 | 0 | 62 | 4 | 182 | 0 | 0 | 0 | 0 | 198 | 0 | 0 | 16 | 0 | 0 | 0 | 0 | 31 | 41 | 701 | 1000 | 3 | 1 |
| 197 | 0 | 62 | 8 | 0 | 0 | 0 | 0 | 49 | 200 | 242 | 0 | 0 | 242 | 18 | 15 | 36 | 0 | 0 | 691 | 1000 | 3 | 1 |
| 198 | 62 | 0 | 131 | 0 | 48 | 151 | 0 | 0 | 0 | 0 | 0 | 237 | 0 | 0 | 15 | 0 | 0 | 21 | 608 | 1000 | 3 | 1 |
| 199 | 0 | 62 | 154 | 0 | 0 | 0 | 0 | 121 | 0 | 0 | 0 | 0 | 13 | 0 | 15 | 31 | 0 | 0 | 433 | 1000 | 3 | 1 |
| 200 | 62 | 0 | 87 | 118 | 0 | 0 | 0 | 0 | 133 | 0 | 0 | 0 | 11 | 0 | 18 | 36 | 0 | 41 | 679 | 1000 | 3 | 1 |
| 201 | 0 | 73 | 14 | 0 | 0 | 0 | 0 | 72 | 0 | 0 | 0 | 0 | 0 | 18 | 0 | 36 | 0 | 24 | 584 | 1000 | 3 | 1 |
| 202 | 73 | 0 | 32 | 0 | 0 | 0 | 0 | 95 | 108 | 0 | 0 | 0 | 79 | 0 | 0 | 0 | 0 | 48 | 650 | 1000 | 3 | 1 |
| 203 | 73 | 0 | 29 | 0 | 0 | 0 | 0 | 49 | 0 | 0 | 0 | 0 | 0 | 0 | 0 | 36 | 0 | 48 | 648 | 1000 | 3 | 1 |
| 204 | 73 | 0 | 56 | 0 | 0 | 0 | 0 | 0 | 198 | 0 | 0 | 0 | 0 | 0 | 0 | 36 | 0 | 0 | 581 | 1000 | 3 | 1 |
| 205 | 0 | 73 | 113 | 0 | 39 | 0 | 0 | 49 | 0 | 242 | 0 | 0 | 242 | 0 | 15 | 36 | 0 | 0 | 523 | 1000 | 3 | 1 |
| 206 | 73 | 0 | 21 | 0 | 0 | 0 | 0 | 0 | 0 | 0 | 0 | 0 | 0 | 0 | 15 | 36 | 0 | 0 | 580 | 1000 | 3 | 1 |
| 207 | 73 | 0 | 128 | 0 | 0 | 117 | 0 | 0 | 0 | 0 | 0 | 0 | 129 | 0 | 15 | 0 | 0 | 0 | 500 | 1000 | 3 | 1 |
| 208 | 0 | 73 | 61 | 0 | 0 | 0 | 0 | 149 | 0 | 0 | 0 | 13 | 0 | 0 | 0 | 0 | 0 | 24 | 680 | 1000 | 3 | 1 |
| 209 | 0 | 73 | 563 | 0 | 185 | 0 | 0 | 0 | 0 | 0 | 0 | 16 | 0 | 0 | 0 | 36 | 0 | 0 | 127 | 1000 | 3 | 1 |

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 210 | 73 | 0 | 138 | 0 | 49 | 0 | 0 | 0 | 0 | 0 | 249 | 0 | 0 | 18 | 0 | 0 | 0 | 24 | 448 | 1000 | 3 | 1 |
| 211 | 0 | 73 | 9 | 185 | 0 | 0 | 0 | 0 | 0 | 0 | 16 | 0 | 0 | 0 | 0 | 0 | 0 | 0 | 717 | 1000 | 3 | 1 |
| 212 | 0 | 73 | 75 | 0 | 0 | 0 | 0 | 185 | 0 | 0 | 0 | 0 | 16 | 0 | 0 | 0 | 36 | 0 | 615 | 1000 | 3 | 1 |
| 213 | 0 | 73 | 214 | 0 | 70 | 0 | 0 | 0 | 0 | 0 | 79 | 0 | 0 | 18 | 0 | 36 | 0 | 0 | 510 | 1000 | 3 | 1 |
| 214 | 73 | 0 | 8 | 186 | 0 | 0 | 0 | 0 | 0 | 0 | 17 | 0 | 0 | 0 | 0 | 36 | 0 | 24 | 638 | 1000 | 3 | 1 |
| 215 | 0 | 73 | 14 | 0 | 0 | 0 | 111 | 0 | 0 | 10 | 0 | 0 | 0 | 0 | 0 | 0 | 36 | 0 | 739 | 1000 | 3 | 1 |
| 216 | 0 | 73 | 40 | 0 | 0 | 0 | 0 | 94 | 0 | 0 | 0 | 196 | 0 | 0 | 18 | 0 | 0 | 24 | 628 | 1000 | 3 | 1 |
| 217 | 73 | 0 | 10 | 0 | 0 | 0 | 0 | 40 | 13 | 0 | 0 | 0 | 104 | 0 | 0 | 0 | 36 | 48 | 633 | 1000 | 3 | 1 |
| 218 | 0 | 73 | 482 | 0 | 0 | 0 | 0 | 0 | 0 | 0 | 0 | 0 | 0 | 0 | 0 | 0 | 36 | 48 | 215 | 1000 | 3 | 1 |
| 219 | 0 | 73 | 4 | 0 | 151 | 0 | 0 | 30 | 0 | 0 | 0 | 0 | 0 | 0 | 0 | 36 | 0 | 24 | 683 | 1000 | 3 | 1 |
| 220 | 73 | 0 | 120 | 0 | 0 | 119 | 0 | 0 | 0 | 0 | 150 | 0 | 0 | 18 | 0 | 0 | 36 | 48 | 454 | 1000 | 3 | 1 |
| 221 | 73 | 0 | 299 | 0 | 151 | 0 | 0 | 0 | 0 | 0 | 0 | 148 | 0 | 18 | 0 | 0 | 0 | 48 | 398 | 1000 | 3 | 1 |
| 222 | 0 | 73 | 14 | 30 | 0 | 0 | 0 | 0 | 0 | 0 | 0 | 104 | 13 | 0 | 0 | 36 | 0 | 48 | 651 | 1000 | 3 | 1 |
| 223 | 73 | 0 | 8 | 0 | 0 | 0 | 95 | 29 | 0 | 0 | 0 | 0 | 0 | 0 | 0 | 0 | 0 | 48 | 653 | 1000 | 3 | 1 |
| 224 | 0 | 73 | 10 | 0 | 0 | 0 | 0 | 0 | 0 | 0 | 0 | 0 | 145 | 0 | 18 | 0 | 0 | 0 | 744 | 1000 | 3 | 1 |
| 225 | 73 | 0 | 462 | 0 | 151 | 0 | 0 | 0 | 0 | 0 | 13 | 79 | 0 | 18 | 0 | 36 | 36 | 48 | 216 | 1000 | 3 | 1 |
| 226 | 73 | 0 | 197 | 0 | 72 | 0 | 0 | 0 | 0 | 16 | 0 | 16 | 0 | 0 | 18 | 0 | 36 | 48 | 514 | 1000 | 3 | 1 |
| 227 | 0 | 73 | 549 | 0 | 185 | 0 | 185 | 0 | 0 | 0 | 0 | 0 | 0 | 0 | 0 | 0 | 0 | 0 | 141 | 1000 | 3 | 1 |
| 228 | 0 | 73 | 9 | 0 | 0 | 0 | 0 | 0 | 0 | 0 | 0 | 0 | 13 | 18 | 0 | 36 | 36 | 24 | 663 | 1000 | 3 | 1 |
| 229 | 73 | 0 | 446 | 0 | 149 | 0 | 0 | 0 | 0 | 0 | 200 | 0 | 0 | 0 | 18 | 0 | 0 | 24 | 259 | 1000 | 3 | 1 |
| 230 | 0 | 73 | 19 | 0 | 0 | 0 | 0 | 39 | 0 | 0 | 0 | 0 | 0 | 0 | 18 | 36 | 0 | 24 | 606 | 1000 | 3 | 1 |
| 231 | 73 | 0 | 112 | 0 | 39 | 186 | 0 | 0 | 198 | 0 | 0 | 0 | 0 | 0 | 18 | 0 | 0 | 0 | 560 | 1000 | 3 | 1 |
| 232 | 0 | 73 | 189 | 0 | 0 | 111 | 0 | 0 | 17 | 0 | 0 | 0 | 0 | 0 | 18 | 36 | 36 | 24 | 456 | 1000 | 3 | 1 |
| 233 | 73 | 0 | 124 | 0 | 0 | 0 | 0 | 0 | 0 | 10 | 0 | 0 | 0 | 16 | 18 | 36 | 0 | 0 | 664 | 1000 | 3 | 1 |
| 234 | 73 | 0 | 43 | 0 | 0 | 0 | 0 | 186 | 0 | 16 | 0 | 0 | 0 | 0 | 0 | 0 | 0 | 24 | 621 | 1000 | 3 | 1 |
| 235 | 73 | 0 | 311 | 0 | 117 | 0 | 0 | 0 | 132 | 0 | 0 | 0 | 0 | 0 | 0 | 36 | 36 | 0 | 313 | 1000 | 3 | 1 |
| 236 | 0 | 73 | 100 | 0 | 29 | 0 | 0 | 0 | 0 | 0 | 0 | 144 | 0 | 0 | 18 | 0 | 0 | 0 | 635 | 1000 | 3 | 1 |
| 237 | 0 | 73 | 9 | 0 | 0 | 0 | 0 | 0 | 0 | 0 | 0 | 102 | 0 | 0 | 18 | 36 | 36 | 0 | 668 | 1000 | 3 | 1 |
| 238 | 73 | 0 | 282 | 0 | 93 | 0 | 93 | 0 | 0 | 103 | 0 | 0 | 0 | 0 | 0 | 0 | 0 | 0 | 431 | 1000 | 3 | 1 |
| 239 | 0 | 73 | 66 | 0 | 30 | 0 | 0 | 0 | 0 | 0 | 0 | 146 | 0 | 0 | 18 | 0 | 36 | 24 | 644 | 1000 | 3 | 1 |
| 240 | 73 | 0 | 140 | 0 | 49 | 0 | 0 | 0 | 0 | 242 | 0 | 0 | 0 | 16 | 0 | 0 | 0 | 0 | 460 | 1000 | 3 | 1 |
| 241 | 73 | 0 | 4 | 71 | 0 | 0 | 0 | 93 | 0 | 0 | 0 | 78 | 0 | 0 | 0 | 0 | 0 | 24 | 732 | 1000 | 3 | 1 |
| 242 | 0 | 73 | 94 | 0 | 0 | 0 | 0 | 49 | 0 | 103 | 0 | 0 | 0 | 0 | 0 | 0 | 36 | 0 | 600 | 1000 | 3 | 1 |
| 243 | 73 | 0 | 23 | 0 | 0 | 0 | 0 | 0 | 0 | 0 | 0 | 240 | 0 | 0 | 18 | 36 | 0 | 0 | 616 | 1000 | 3 | 1 |
| 244 | 73 | 0 | 252 | 0 | 118 | 40 | 0 | 0 | 0 | 0 | 0 | 129 | 0 | 0 | 0 | 0 | 0 | 24 | 386 | 1000 | 3 | 1 |
| 245 | 73 | 0 | 46 | 0 | 0 | 0 | 0 | 0 | 0 | 197 | 0 | 0 | 0 | 0 | 18 | 36 | 0 | 48 | 542 | 1000 | 3 | 1 |
| 246 | 73 | 0 | 28 | 0 | 0 | 0 | 0 | 93 | 0 | 0 | 0 | 102 | 0 | 0 | 18 | 0 | 0 | 0 | 704 | 1000 | 3 | 1 |
| 247 | 0 | 73 | 29 | 0 | 93 | 0 | 0 | 30 | 0 | 0 | 0 | 0 | 0 | 0 | 18 | 0 | 36 | 48 | 671 | 1000 | 3 | 1 |
| 248 | 0 | 73 | 74 | 0 | 0 | 70 | 0 | 0 | 0 | 0 | 79 | 0 | 0 | 18 | 18 | 36 | 0 | 0 | 650 | 1000 | 3 | 1 |
| 249 | 73 | 0 | 4 | 0 | 0 | 0 | 118 | 0 | 0 | 0 | 0 | 129 | 0 | 18 | 0 | 0 | 36 | 24 | 598 | 1000 | 3 | 1 |
| 250 | 0 | 73 | 74 | 0 | 118 | 70 | 0 | 0 | 0 | 77 | 0 | 0 | 0 | 0 | 18 | 0 | 36 | 0 | 652 | 1000 | 3 | 1 |
| 251 | 100 | 0 | 120 | 0 | 0 | 104 | 0 | 0 | 118 | 0 | 0 | 0 | 0 | 0 | 0 | 50 | 0 | 33 | 474 | 1000 | 2 | 2 |

-continued

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 252 | 100 | 0 | 11 | 0 | 0 | 0 | 116 | 0 | 0 | 0 | 0 | 10 | 0 | 0 | 0 | 0 | 0 | 67 | 696 | 1000 | 2 | 2 |
| 253 | 100 | 0 | 11 | 112 | 0 | 0 | 0 | 0 | 0 | 0 | 0 | 10 | 0 | 0 | 0 | 0 | 0 | 0 | 717 | 1000 | 2 | 2 |
| 254 | 100 | 0 | 119 | 0 | 0 | 103 | 0 | 0 | 0 | 114 | 0 | 0 | 0 | 0 | 0 | 50 | 0 | 0 | 514 | 1000 | 2 | 2 |
| 255 | 100 | 0 | 18 | 0 | 0 | 0 | 57 | 0 | 0 | 0 | 290 | 0 | 0 | 25 | 0 | 0 | 0 | 33 | 477 | 1000 | 2 | 2 |
| 256 | 100 | 0 | 5 | 0 | 0 | 0 | 112 | 0 | 0 | 81 | 0 | 0 | 0 | 0 | 0 | 50 | 0 | 0 | 723 | 1000 | 2 | 2 |
| 257 | 0 | 100 | 6 | 73 | 0 | 0 | 214 | 0 | 0 | 0 | 19 | 0 | 0 | 0 | 0 | 0 | 0 | 0 | 586 | 1000 | 2 | 2 |
| 258 | 100 | 0 | 5 | 0 | 0 | 0 | 0 | 44 | 0 | 0 | 0 | 0 | 283 | 25 | 0 | 0 | 50 | 0 | 599 | 1000 | 2 | 2 |
| 259 | 100 | 0 | 14 | 0 | 0 | 0 | 57 | 0 | 0 | 219 | 0 | 0 | 0 | 0 | 25 | 50 | 0 | 67 | 497 | 1000 | 2 | 2 |
| 260 | 100 | 0 | 135 | 0 | 0 | 0 | 0 | 0 | 0 | 0 | 0 | 0 | 0 | 0 | 0 | 0 | 0 | 33 | 657 | 1000 | 2 | 2 |
| 261 | 0 | 100 | 11 | 0 | 0 | 0 | 114 | 135 | 0 | 10 | 0 | 0 | 152 | 0 | 0 | 50 | 0 | 0 | 427 | 1000 | 2 | 2 |
| 262 | 100 | 0 | 19 | 0 | 0 | 0 | 0 | 138 | 0 | 0 | 0 | 0 | 0 | 25 | 0 | 0 | 50 | 33 | 681 | 1000 | 2 | 2 |
| 263 | 100 | 0 | 11 | 0 | 0 | 0 | 112 | 0 | 0 | 0 | 0 | 10 | 0 | 0 | 0 | 50 | 0 | 67 | 474 | 1000 | 2 | 2 |
| 264 | 100 | 0 | 39 | 0 | 0 | 30 | 0 | 0 | 0 | 0 | 0 | 0 | 147 | 0 | 25 | 0 | 0 | 0 | 692 | 1000 | 2 | 2 |
| 265 | 100 | 0 | 12 | 0 | 0 | 0 | 0 | 0 | 0 | 0 | 19 | 0 | 0 | 25 | 25 | 0 | 50 | 33 | 609 | 1000 | 2 | 2 |
| 266 | 100 | 0 | 11 | 114 | 0 | 0 | 0 | 0 | 10 | 0 | 0 | 0 | 0 | 0 | 25 | 50 | 0 | 0 | 655 | 1000 | 2 | 2 |
| 267 | 100 | 0 | 11 | 30 | 0 | 0 | 0 | 0 | 0 | 0 | 150 | 0 | 0 | 0 | 0 | 0 | 50 | 33 | 634 | 1000 | 2 | 2 |
| 268 | 0 | 100 | 91 | 0 | 0 | 72 | 0 | 0 | 82 | 0 | 0 | 0 | 0 | 0 | 0 | 0 | 0 | 0 | 572 | 1000 | 2 | 2 |
| 269 | 100 | 0 | 61 | 0 | 56 | 43 | 0 | 0 | 0 | 0 | 120 | 0 | 0 | 0 | 0 | 0 | 50 | 33 | 546 | 1000 | 2 | 2 |
| 270 | 100 | 0 | 140 | 0 | 108 | 0 | 0 | 0 | 0 | 216 | 0 | 0 | 0 | 0 | 0 | 0 | 0 | 0 | 375 | 1000 | 2 | 2 |
| 271 | 100 | 0 | 302 | 0 | 0 | 0 | 0 | 0 | 0 | 0 | 0 | 278 | 0 | 0 | 0 | 50 | 50 | 67 | 256 | 1000 | 2 | 2 |
| 272 | 100 | 0 | 5 | 43 | 0 | 0 | 0 | 0 | 0 | 216 | 82 | 0 | 0 | 25 | 25 | 0 | 0 | 33 | 527 | 1000 | 2 | 2 |
| 273 | 100 | 0 | 12 | 72 | 0 | 0 | 0 | 0 | 0 | 0 | 0 | 148 | 0 | 0 | 0 | 0 | 50 | 33 | 650 | 1000 | 2 | 2 |
| 274 | 100 | 0 | 40 | 0 | 0 | 0 | 0 | 135 | 0 | 152 | 0 | 0 | 0 | 25 | 25 | 0 | 0 | 0 | 527 | 1000 | 2 | 2 |
| 275 | 100 | 0 | 11 | 31 | 0 | 0 | 0 | 57 | 0 | 0 | 0 | 0 | 0 | 0 | 0 | 50 | 0 | 67 | 514 | 1000 | 2 | 2 |
| 276 | 100 | 0 | 14 | 0 | 0 | 0 | 0 | 0 | 0 | 150 | 0 | 0 | 285 | 0 | 0 | 0 | 0 | 67 | 426 | 1000 | 2 | 2 |
| 277 | 100 | 0 | 5 | 0 | 0 | 0 | 135 | 103 | 0 | 216 | 117 | 0 | 0 | 25 | 0 | 0 | 50 | 33 | 585 | 1000 | 2 | 2 |
| 278 | 100 | 0 | 18 | 0 | 0 | 0 | 43 | 0 | 0 | 0 | 80 | 0 | 0 | 0 | 25 | 50 | 0 | 0 | 514 | 1000 | 2 | 2 |
| 279 | 100 | 0 | 106 | 0 | 0 | 0 | 71 | 71 | 0 | 0 | 290 | 0 | 0 | 0 | 25 | 0 | 0 | 0 | 573 | 1000 | 2 | 2 |
| 280 | 100 | 0 | 11 | 0 | 0 | 0 | 167 | 0 | 0 | 0 | 0 | 14 | 0 | 25 | 25 | 50 | 0 | 67 | 663 | 1000 | 2 | 2 |
| 281 | 100 | 0 | 19 | 0 | 0 | 57 | 0 | 0 | 0 | 0 | 0 | 10 | 0 | 0 | 0 | 50 | 0 | 33 | 608 | 1000 | 2 | 2 |
| 282 | 100 | 0 | 65 | 0 | 116 | 0 | 0 | 0 | 0 | 0 | 15 | 0 | 15 | 25 | 0 | 50 | 0 | 67 | 405 | 1000 | 2 | 2 |
| 283 | 100 | 0 | 353 | 0 | 0 | 0 | 0 | 114 | 0 | 0 | 0 | 0 | 0 | 0 | 25 | 50 | 33 | 33 | 279 | 1000 | 2 | 2 |
| 284 | 100 | 0 | 170 | 167 | 0 | 165 | 0 | 0 | 0 | 0 | 10 | 0 | 0 | 0 | 0 | 0 | 67 | 67 | 466 | 1000 | 2 | 2 |
| 285 | 100 | 0 | 12 | 0 | 0 | 0 | 0 | 0 | 0 | 0 | 154 | 0 | 10 | 0 | 0 | 0 | 50 | 33 | 639 | 1000 | 2 | 2 |
| 286 | 100 | 0 | 18 | 136 | 0 | 0 | 0 | 0 | 0 | 78 | 0 | 0 | 0 | 25 | 0 | 0 | 0 | 33 | 724 | 1000 | 2 | 2 |
| 287 | 100 | 0 | 12 | 0 | 0 | 0 | 71 | 114 | 0 | 0 | 0 | 0 | 0 | 0 | 0 | 50 | 0 | 33 | 488 | 1000 | 2 | 2 |
| 288 | 100 | 0 | 19 | 0 | 0 | 0 | 116 | 0 | 0 | 0 | 0 | 0 | 10 | 25 | 25 | 0 | 50 | 0 | 657 | 1000 | 2 | 2 |
| 289 | 100 | 0 | 6 | 0 | 0 | 0 | 0 | 214 | 19 | 0 | 0 | 0 | 0 | 0 | 25 | 0 | 50 | 67 | 626 | 1000 | 2 | 2 |
| 290 | 100 | 0 | 9 | 0 | 0 | 0 | 0 | 0 | 0 | 286 | 0 | 0 | 114 | 0 | 0 | 0 | 0 | 0 | 658 | 1000 | 2 | 2 |
| 291 | 0 | 100 | 6 | 103 | 0 | 0 | 57 | 0 | 0 | 0 | 0 | 0 | 0 | 0 | 25 | 50 | 0 | 33 | 602 | 1000 | 2 | 2 |
| 292 | 100 | 0 | 5 | 0 | 0 | 0 | 0 | 0 | 0 | 0 | 0 | 0 | 0 | 25 | 0 | 50 | 0 | 67 | 410 | 1000 | 2 | 2 |
| 293 | 100 | 0 | 44 | 0 | 0 | 0 | 0 | 163 | 0 | 0 | 15 | 0 | 0 | 0 | 0 | 0 | 50 | 0 | 628 | 1000 | 2 | 2 |

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 294 | 0 | 100 | 89 | 0 | 30 | 0 | 0 | 0 | 0 | 0 | 150 | 0 | 0 | 25 | 0 | 0 | 0 | 0 | 608 | 1000 | 2 | 2 |
| 295 | 0 | 100 | 233 | 0 | 0 | 214 | 0 | 0 | 19 | 0 | 0 | 0 | 0 | 25 | 0 | 0 | 0 | 0 | 350 | 1000 | 2 | 2 |
| 296 | 0 | 100 | 147 | 135 | 43 | 0 | 0 | 0 | 0 | 214 | 0 | 0 | 0 | 0 | 0 | 50 | 0 | 0 | 447 | 1000 | 2 | 2 |
| 297 | 100 | 0 | 18 | 104 | 0 | 0 | 0 | 0 | 0 | 0 | 0 | 150 | 0 | 25 | 0 | 50 | 0 | 0 | 522 | 1000 | 2 | 2 |
| 298 | 100 | 0 | 18 | 0 | 216 | 0 | 0 | 0 | 0 | 0 | 118 | 0 | 0 | 0 | 25 | 0 | 50 | 33 | 551 | 1000 | 2 | 2 |
| 299 | 0 | 100 | 645 | 0 | 0 | 0 | 0 | 0 | 0 | 80 | 19 | 0 | 158 | 0 | 0 | 0 | 0 | 33 | 39 | 1000 | 2 | 2 |
| 300 | 100 | 0 | 5 | 72 | 0 | 0 | 32 | 0 | 0 | 0 | 0 | 0 | 0 | 15 | 0 | 0 | 31 | 3 | 710 | 1000 | 3 | 1 |
| 301 | 0 | 62 | 4 | 0 | 0 | 0 | 0 | 0 | 0 | 0 | 0 | 194 | 0 | 0 | 15 | 0 | 31 | 41 | 658 | 1000 | 3 | 1 |
| 302 | 62 | 0 | 3 | 39 | 0 | 0 | 0 | 0 | 0 | 197 | 0 | 0 | 0 | 0 | 0 | 0 | 0 | 0 | 656 | 1000 | 3 | 1 |
| 303 | 0 | 62 | 8 | 40 | 0 | 0 | 0 | 0 | 162 | 0 | 0 | 0 | 0 | 15 | 0 | 0 | 0 | 21 | 673 | 1000 | 3 | 1 |
| 304 | 62 | 0 | 3 | 32 | 0 | 0 | 0 | 0 | 0 | 0 | 0 | 125 | 0 | 0 | 0 | 0 | 31 | 41 | 670 | 1000 | 3 | 1 |
| 305 | 0 | 62 | 117 | 0 | 0 | 114 | 0 | 114 | 0 | 126 | 0 | 0 | 0 | 15 | 0 | 0 | 0 | 0 | 565 | 1000 | 3 | 1 |
| 306 | 62 | 0 | 5 | 0 | 0 | 0 | 0 | 181 | 16 | 0 | 0 | 0 | 13 | 0 | 0 | 31 | 31 | 21 | 662 | 1000 | 3 | 1 |
| 307 | 0 | 62 | 127 | 0 | 0 | 0 | 0 | 151 | 0 | 0 | 0 | 0 | 0 | 0 | 0 | 0 | 0 | 0 | 614 | 1000 | 3 | 1 |
| 308 | 62 | 0 | 141 | 0 | 0 | 0 | 0 | 0 | 0 | 10 | 0 | 0 | 0 | 0 | 15 | 31 | 31 | 21 | 582 | 1000 | 3 | 1 |
| 309 | 0 | 62 | 8 | 119 | 0 | 0 | 0 | 0 | 0 | 0 | 0 | 0 | 0 | 15 | 0 | 0 | 0 | 21 | 734 | 1000 | 3 | 1 |
| 310 | 62 | 0 | 30 | 0 | 0 | 31 | 0 | 0 | 160 | 0 | 0 | 0 | 0 | 15 | 0 | 0 | 31 | 21 | 651 | 1000 | 3 | 1 |
| 311 | 0 | 62 | 12 | 0 | 0 | 0 | 48 | 0 | 242 | 0 | 0 | 0 | 0 | 15 | 0 | 0 | 0 | 0 | 591 | 1000 | 3 | 1 |
| 312 | 62 | 0 | 44 | 0 | 0 | 40 | 0 | 0 | 0 | 0 | 200 | 0 | 0 | 15 | 0 | 31 | 0 | 21 | 592 | 1000 | 3 | 1 |
| 313 | 0 | 62 | 4 | 0 | 0 | 0 | 0 | 39 | 0 | 0 | 0 | 196 | 0 | 0 | 0 | 0 | 0 | 0 | 695 | 1000 | 3 | 1 |
| 314 | 62 | 0 | 5 | 0 | 0 | 0 | 0 | 75 | 0 | 0 | 84 | 82 | 0 | 0 | 0 | 0 | 0 | 0 | 777 | 1000 | 3 | 1 |
| 315 | 0 | 62 | 12 | 140 | 0 | 75 | 0 | 39 | 0 | 0 | 0 | 0 | 0 | 0 | 15 | 0 | 0 | 0 | 734 | 1000 | 3 | 1 |
| 316 | 62 | 0 | 66 | 0 | 0 | 0 | 0 | 0 | 0 | 0 | 85 | 194 | 13 | 0 | 0 | 31 | 31 | 0 | 667 | 1000 | 3 | 1 |
| 317 | 0 | 62 | 46 | 0 | 76 | 0 | 0 | 0 | 0 | 0 | 0 | 0 | 0 | 15 | 0 | 0 | 0 | 41 | 659 | 1000 | 3 | 1 |
| 318 | 62 | 0 | 206 | 0 | 0 | 0 | 0 | 0 | 11 | 0 | 11 | 0 | 0 | 15 | 0 | 31 | 0 | 41 | 483 | 1000 | 3 | 1 |
| 319 | 0 | 62 | 6 | 118 | 0 | 0 | 121 | 0 | 0 | 0 | 0 | 0 | 0 | 0 | 0 | 0 | 31 | 0 | 712 | 1000 | 3 | 1 |
| 320 | 62 | 0 | 11 | 0 | 0 | 0 | 0 | 119 | 0 | 199 | 0 | 0 | 0 | 0 | 0 | 0 | 0 | 0 | 753 | 1000 | 3 | 1 |
| 321 | 0 | 62 | 98 | 0 | 40 | 0 | 0 | 114 | 0 | 0 | 120 | 0 | 0 | 0 | 0 | 31 | 31 | 41 | 545 | 1000 | 3 | 1 |
| 322 | 62 | 0 | 30 | 0 | 0 | 0 | 0 | 0 | 0 | 0 | 0 | 0 | 10 | 15 | 0 | 31 | 0 | 21 | 727 | 1000 | 3 | 1 |
| 323 | 0 | 62 | 110 | 0 | 0 | 0 | 0 | 0 | 0 | 0 | 129 | 0 | 155 | 15 | 0 | 0 | 0 | 0 | 554 | 1000 | 3 | 1 |
| 324 | 62 | 0 | 12 | 31 | 0 | 0 | 114 | 0 | 0 | 0 | 0 | 155 | 0 | 0 | 15 | 31 | 0 | 0 | 695 | 1000 | 3 | 1 |
| 325 | 0 | 62 | 7 | 0 | 0 | 31 | 0 | 0 | 244 | 0 | 0 | 0 | 0 | 0 | 0 | 0 | 0 | 21 | 673 | 1000 | 3 | 1 |
| 326 | 62 | 0 | 43 | 48 | 0 | 0 | 0 | 31 | 16 | 155 | 0 | 0 | 0 | 0 | 0 | 0 | 31 | 21 | 642 | 1000 | 3 | 1 |
| 327 | 62 | 0 | 11 | 0 | 0 | 0 | 181 | 0 | 0 | 158 | 0 | 0 | 0 | 0 | 0 | 31 | 31 | 0 | 585 | 1000 | 3 | 1 |
| 328 | 62 | 0 | 4 | 0 | 0 | 0 | 0 | 0 | 0 | 0 | 0 | 0 | 0 | 15 | 15 | 31 | 31 | 41 | 707 | 1000 | 3 | 1 |
| 329 | 62 | 0 | 28 | 0 | 32 | 0 | 0 | 0 | 14 | 0 | 0 | 0 | 10 | 0 | 15 | 31 | 31 | 21 | 694 | 1000 | 3 | 1 |
| 330 | 0 | 62 | 106 | 0 | 0 | 0 | 0 | 0 | 0 | 0 | 0 | 0 | 0 | 15 | 0 | 0 | 0 | 41 | 555 | 1000 | 3 | 1 |
| 331 | 62 | 0 | 3 | 119 | 152 | 0 | 0 | 0 | 0 | 0 | 0 | 0 | 0 | 0 | 15 | 0 | 31 | 21 | 739 | 1000 | 3 | 1 |
| 332 | 62 | 0 | 301 | 0 | 0 | 0 | 0 | 118 | 0 | 0 | 160 | 0 | 0 | 0 | 15 | 31 | 0 | 41 | 385 | 1000 | 3 | 1 |
| 333 | 0 | 62 | 12 | 31 | 0 | 0 | 0 | 0 | 0 | 0 | 0 | 0 | 10 | 0 | 0 | 0 | 0 | 0 | 715 | 1000 | 3 | 1 |
| 334 | 62 | 0 | 5 | 0 | 0 | 0 | 0 | 0 | 0 | 0 | 0 | 0 | 0 | 0 | 0 | 31 | 0 | 21 | 774 | 1000 | 3 | 1 |
| 335 | 0 | 62 | 87 | 0 | 0 | 75 | 0 | 0 | 85 | 0 | 0 | 0 | 0 | 0 | 0 | 0 | 31 | 21 | 639 | 1000 | 3 | 1 |

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 336 | 62 | 0 | 116 | 0 | 0 | 116 | 0 | 0 | 0 | 0 | 0 | 127 | 0 | 0 | 15 | 0 | 31 | 41 | 492 | 1000 | 3 | 1 |
| 337 | 62 | 0 | 30 | 0 | 0 | 0 | 0 | 119 | 0 | 0 | 0 | 10 | 0 | 0 | 0 | 0 | 31 | 21 | 727 | 1000 | 3 | 1 |
| 338 | 0 | 62 | 74 | 0 | 0 | 0 | 0 | 183 | 0 | 0 | 15 | 0 | 0 | 0 | 0 | 0 | 31 | 41 | 593 | 1000 | 3 | 1 |
| 339 | 62 | 0 | 11 | 182 | 0 | 0 | 0 | 0 | 0 | 0 | 0 | 0 | 16 | 0 | 15 | 0 | 0 | 21 | 663 | 1000 | 3 | 1 |
| 340 | 0 | 62 | 39 | 0 | 0 | 32 | 0 | 0 | 0 | 0 | 0 | 0 | 158 | 0 | 15 | 0 | 31 | 41 | 622 | 1000 | 3 | 1 |
| 341 | 62 | 0 | 14 | 0 | 0 | 0 | 0 | 116 | 0 | 0 | 0 | 127 | 0 | 0 | 0 | 31 | 0 | 21 | 641 | 1000 | 3 | 1 |
| 342 | 0 | 62 | 189 | 0 | 0 | 182 | 0 | 0 | 0 | 240 | 0 | 0 | 0 | 0 | 0 | 0 | 0 | 41 | 531 | 1000 | 3 | 1 |
| 343 | 62 | 0 | 8 | 48 | 0 | 0 | 0 | 0 | 0 | 199 | 0 | 16 | 0 | 15 | 0 | 0 | 31 | 21 | 566 | 1000 | 3 | 1 |
| 344 | 0 | 62 | 9 | 0 | 0 | 0 | 0 | 40 | 0 | 0 | 0 | 0 | 128 | 0 | 0 | 0 | 0 | 41 | 618 | 1000 | 3 | 1 |
| 345 | 62 | 0 | 3 | 116 | 0 | 0 | 0 | 0 | 0 | 0 | 0 | 84 | 0 | 0 | 15 | 0 | 31 | 41 | 604 | 1000 | 3 | 1 |
| 346 | 62 | 0 | 68 | 0 | 0 | 75 | 0 | 0 | 0 | 156 | 0 | 0 | 0 | 0 | 15 | 31 | 31 | 41 | 624 | 1000 | 3 | 1 |
| 347 | 0 | 62 | 4 | 0 | 0 | 0 | 31 | 0 | 15 | 0 | 0 | 237 | 0 | 0 | 15 | 31 | 0 | 21 | 680 | 1000 | 3 | 1 |
| 348 | 62 | 0 | 22 | 0 | 0 | 0 | 0 | 48 | 79 | 0 | 0 | 0 | 106 | 0 | 0 | 0 | 31 | 21 | 581 | 1000 | 3 | 1 |
| 349 | 0 | 62 | 7 | 96 | 0 | 0 | 0 | 182 | 0 | 0 | 0 | 0 | 0 | 0 | 0 | 0 | 31 | 41 | 658 | 1000 | 3 | 1 |
| 350 | 0 | 62 | 168 | 0 | 0 | 0 | 70 | 0 | 0 | 0 | 0 | 13 | 16 | 0 | 0 | 0 | 31 | 21 | 521 | 1000 | 3 | 1 |
| 351 | 0 | 73 | 9 | 0 | 0 | 0 | 0 | 0 | 0 | 0 | 0 | 0 | 0 | 0 | 0 | 0 | 0 | 0 | 769 | 1000 | 3 | 1 |
| 352 | 73 | 0 | 120 | 0 | 149 | 148 | 0 | 0 | 0 | 0 | 0 | 13 | 16 | 0 | 0 | 36 | 0 | 24 | 602 | 1000 | 3 | 1 |
| 353 | 73 | 0 | 184 | 0 | 70 | 186 | 0 | 0 | 0 | 0 | 0 | 0 | 0 | 18 | 18 | 36 | 0 | 24 | 462 | 1000 | 3 | 1 |
| 354 | 73 | 0 | 296 | 0 | 0 | 0 | 0 | 0 | 0 | 0 | 79 | 0 | 0 | 0 | 0 | 0 | 36 | 0 | 391 | 1000 | 3 | 1 |
| 355 | 0 | 73 | 222 | 0 | 0 | 85 | 0 | 0 | 0 | 105 | 0 | 0 | 0 | 0 | 0 | 0 | 0 | 48 | 557 | 1000 | 3 | 1 |
| 356 | 0 | 73 | 109 | 0 | 0 | 0 | 0 | 0 | 0 | 0 | 80 | 0 | 193 | 0 | 0 | 0 | 36 | 0 | 551 | 1000 | 3 | 1 |
| 357 | 73 | 0 | 14 | 71 | 39 | 0 | 0 | 0 | 0 | 0 | 0 | 0 | 0 | 18 | 18 | 36 | 0 | 24 | 684 | 1000 | 3 | 1 |
| 358 | 73 | 0 | 86 | 0 | 0 | 0 | 29 | 0 | 0 | 0 | 0 | 144 | 0 | 18 | 18 | 0 | 0 | 0 | 591 | 1000 | 3 | 1 |
| 359 | 73 | 0 | 13 | 0 | 0 | 149 | 0 | 0 | 0 | 0 | 13 | 0 | 0 | 18 | 0 | 36 | 36 | 24 | 587 | 1000 | 3 | 1 |
| 360 | 73 | 0 | 158 | 0 | 0 | 0 | 0 | 0 | 0 | 10 | 0 | 79 | 0 | 0 | 0 | 0 | 0 | 48 | 564 | 1000 | 3 | 1 |
| 361 | 73 | 0 | 172 | 0 | 72 | 0 | 0 | 0 | 0 | 13 | 0 | 0 | 105 | 0 | 0 | 0 | 0 | 48 | 502 | 1000 | 3 | 1 |
| 362 | 73 | 0 | 205 | 0 | 95 | 0 | 0 | 0 | 0 | 0 | 0 | 0 | 242 | 0 | 0 | 0 | 0 | 48 | 456 | 1000 | 3 | 1 |
| 363 | 73 | 0 | 4 | 0 | 0 | 0 | 0 | 0 | 0 | 104 | 0 | 0 | 0 | 0 | 16 | 36 | 36 | 0 | 615 | 1000 | 3 | 1 |
| 364 | 0 | 73 | 71 | 0 | 0 | 0 | 49 | 94 | 0 | 0 | 0 | 0 | 0 | 18 | 18 | 0 | 0 | 24 | 597 | 1000 | 3 | 1 |
| 365 | 73 | 0 | 4 | 151 | 0 | 0 | 0 | 0 | 0 | 13 | 0 | 0 | 0 | 0 | 0 | 0 | 36 | 48 | 693 | 1000 | 3 | 1 |
| 366 | 0 | 73 | 86 | 0 | 112 | 72 | 0 | 0 | 0 | 10 | 0 | 79 | 0 | 0 | 0 | 36 | 0 | 48 | 606 | 1000 | 3 | 1 |
| 367 | 0 | 73 | 318 | 0 | 149 | 0 | 0 | 0 | 0 | 13 | 0 | 0 | 0 | 18 | 0 | 0 | 0 | 24 | 463 | 1000 | 3 | 1 |
| 368 | 73 | 0 | 446 | 0 | 0 | 0 | 0 | 30 | 0 | 0 | 0 | 0 | 149 | 0 | 16 | 0 | 0 | 0 | 277 | 1000 | 3 | 1 |
| 369 | 0 | 73 | 10 | 0 | 0 | 0 | 0 | 0 | 249 | 0 | 0 | 16 | 0 | 0 | 0 | 0 | 0 | 0 | 654 | 1000 | 3 | 1 |
| 370 | 73 | 0 | 4 | 0 | 0 | 0 | 185 | 0 | 0 | 0 | 0 | 0 | 0 | 18 | 18 | 0 | 0 | 48 | 704 | 1000 | 3 | 1 |
| 371 | 0 | 73 | 9 | 0 | 0 | 30 | 49 | 0 | 0 | 0 | 0 | 16 | 149 | 0 | 0 | 0 | 36 | 48 | 578 | 1000 | 3 | 1 |
| 372 | 73 | 0 | 34 | 0 | 0 | 185 | 0 | 0 | 16 | 16 | 0 | 0 | 0 | 0 | 0 | 0 | 0 | 0 | 630 | 1000 | 3 | 1 |
| 373 | 0 | 73 | 160 | 0 | 0 | 0 | 0 | 0 | 0 | 0 | 0 | 0 | 149 | 0 | 18 | 36 | 36 | 0 | 548 | 1000 | 3 | 1 |
| 374 | 73 | 0 | 189 | 0 | 0 | 186 | 49 | 0 | 249 | 0 | 0 | 0 | 0 | 0 | 18 | 0 | 0 | 0 | 511 | 1000 | 3 | 1 |
| 375 | 0 | 73 | 13 | 0 | 0 | 0 | 0 | 0 | 0 | 16 | 0 | 0 | 105 | 0 | 0 | 36 | 0 | 24 | 537 | 1000 | 3 | 1 |
| 376 | 73 | 0 | 4 | 0 | 0 | 0 | 95 | 0 | 0 | 0 | 0 | 0 | 0 | 0 | 0 | 0 | 0 | 48 | 574 | 1000 | 3 | 1 |
| 377 | 0 | 73 | 333 | 0 | 118 | 0 | 0 | 0 | 0 | 0 | 133 | 0 | 0 | 0 | 0 | 0 | 0 | 24 | 319 | 1000 | 3 | 1 |

| Expt # (Stock) | 1 MES [0.5M] | 4 HEPE [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 378 | 73 | 0 | 13 | 30 | 0 | 0 | 0 | 0 | 0 | 0 | 0 | 148 | 0 | 0 | 0 | 0 | 36 | 48 | 652 | 1000 | 3 | 1 |
| 379 | 73 | 0 | 4 | 0 | 0 | 0 | 72 | 0 | 0 | 0 | 0 | 0 | 79 | 18 | 0 | 0 | 0 | 48 | 706 | 1000 | 3 | 1 |
| 380 | 73 | 0 | 125 | 0 | 0 | 114 | 0 | 0 | 0 | 0 | 0 | 10 | 0 | 0 | 0 | 36 | 0 | 48 | 594 | 1000 | 3 | 1 |
| 381 | 0 | 73 | 58 | 0 | 0 | 49 | 0 | 0 | 247 | 0 | 0 | 0 | 0 | 0 | 0 | 36 | 0 | 0 | 538 | 1000 | 3 | 1 |
| 382 | 0 | 73 | 9 | 40 | 0 | 0 | 0 | 0 | 0 | 0 | 0 | 0 | 197 | 0 | 0 | 0 | 0 | 48 | 633 | 1000 | 3 | 1 |
| 383 | 0 | 73 | 32 | 0 | 0 | 0 | 0 | 72 | 0 | 0 | 0 | 79 | 0 | 18 | 0 | 0 | 0 | 48 | 697 | 1000 | 3 | 1 |
| 384 | 73 | 0 | 8 | 29 | 0 | 0 | 0 | 0 | 0 | 246 | 0 | 0 | 0 | 0 | 0 | 0 | 0 | 0 | 544 | 1000 | 3 | 1 |
| 385 | 73 | 0 | 4 | 49 | 0 | 0 | 0 | 0 | 0 | 0 | 0 | 144 | 0 | 0 | 0 | 36 | 0 | 48 | 543 | 1000 | 3 | 1 |
| 386 | 73 | 0 | 13 | 0 | 0 | 0 | 49 | 0 | 0 | 0 | 0 | 0 | 244 | 18 | 0 | 0 | 36 | 24 | 552 | 1000 | 3 | 1 |
| 387 | 0 | 73 | 14 | 0 | 0 | 39 | 0 | 0 | 132 | 0 | 0 | 0 | 0 | 18 | 0 | 36 | 0 | 48 | 634 | 1000 | 3 | 1 |
| 388 | 73 | 0 | 8 | 0 | 0 | 0 | 49 | 0 | 200 | 246 | 0 | 0 | 0 | 0 | 0 | 36 | 0 | 0 | 606 | 1000 | 3 | 1 |
| 389 | 73 | 0 | 4 | 0 | 0 | 0 | 117 | 0 | 200 | 0 | 0 | 0 | 0 | 18 | 0 | 0 | 36 | 24 | 584 | 1000 | 3 | 1 |
| 390 | 73 | 0 | 52 | 0 | 0 | 39 | 39 | 0 | 0 | 0 | 200 | 0 | 0 | 0 | 0 | 0 | 0 | 24 | 512 | 1000 | 3 | 1 |
| 391 | 73 | 0 | 98 | 0 | 39 | 0 | 0 | 0 | 0 | 0 | 0 | 0 | 0 | 0 | 18 | 0 | 36 | 46 | 705 | 1000 | 3 | 1 |
| 392 | 0 | 73 | 14 | 0 | 0 | 0 | 114 | 0 | 0 | 0 | 198 | 0 | 0 | 18 | 0 | 0 | 36 | 0 | 638 | 1000 | 3 | 1 |
| 393 | 73 | 0 | 53 | 0 | 0 | 39 | 0 | 0 | 0 | 0 | 0 | 10 | 0 | 0 | 0 | 0 | 36 | 48 | 687 | 1000 | 3 | 1 |
| 394 | 73 | 0 | 13 | 0 | 0 | 0 | 114 | 0 | 10 | 0 | 107 | 0 | 0 | 0 | 18 | 36 | 0 | 24 | 604 | 1000 | 3 | 1 |
| 395 | 73 | 0 | 8 | 0 | 0 | 0 | 49 | 0 | 0 | 244 | 0 | 242 | 0 | 18 | 0 | 0 | 0 | 24 | 518 | 1000 | 3 | 1 |
| 396 | 0 | 73 | 56 | 0 | 40 | 0 | 0 | 0 | 0 | 0 | 148 | 0 | 197 | 0 | 18 | 36 | 0 | 48 | 676 | 1000 | 3 | 1 |
| 397 | 73 | 0 | 8 | 0 | 0 | 0 | 94 | 49 | 0 | 0 | 0 | 0 | 0 | 0 | 0 | 0 | 36 | 48 | 525 | 1000 | 3 | 1 |
| 398 | 73 | 0 | 99 | 0 | 0 | 0 | 0 | 0 | 10 | 0 | 15 | 0 | 0 | 25 | 0 | 0 | 36 | 48 | 705 | 1000 | 2 | 2 |
| 399 | 73 | 0 | 14 | 114 | 0 | 0 | 0 | 0 | 0 | 10 | 154 | 0 | 10 | 25 | 25 | 0 | 0 | 0 | 709 | 1000 | 2 | 2 |
| 400 | 0 | 73 | 4 | 0 | 0 | 0 | 115 | 29 | 0 | 0 | 118 | 0 | 0 | 0 | 25 | 0 | 36 | 67 | 664 | 1000 | 2 | 2 |
| 401 | 100 | 0 | 18 | 0 | 0 | 0 | 165 | 0 | 0 | 150 | 0 | 0 | 115 | 0 | 0 | 50 | 0 | 33 | 643 | 1000 | 2 | 2 |
| 402 | 0 | 100 | 19 | 0 | 0 | 0 | 0 | 0 | 153 | 0 | 0 | 79 | 0 | 25 | 25 | 50 | 50 | 0 | 166 | 1000 | 2 | 2 |
| 403 | 0 | 100 | 421 | 0 | 135 | 136 | 0 | 0 | 0 | 19 | 287 | 0 | 0 | 25 | 0 | 50 | 0 | 33 | 420 | 1000 | 2 | 2 |
| 404 | 0 | 100 | 155 | 0 | 0 | 104 | 216 | 0 | 153 | 0 | 153 | 0 | 114 | 0 | 25 | 0 | 0 | 33 | 478 | 1000 | 2 | 2 |
| 405 | 0 | 100 | 94 | 0 | 30 | 0 | 0 | 0 | 0 | 0 | 0 | 0 | 0 | 25 | 25 | 50 | 50 | 33 | 619 | 1000 | 2 | 2 |
| 406 | 100 | 0 | 12 | 0 | 0 | 104 | 0 | 0 | 0 | 0 | 0 | 79 | 10 | 25 | 0 | 50 | 0 | 33 | 529 | 1000 | 2 | 2 |
| 407 | 0 | 100 | 80 | 72 | 135 | 0 | 0 | 0 | 0 | 19 | 0 | 0 | 0 | 0 | 25 | 0 | 50 | 33 | 484 | 1000 | 2 | 2 |
| 408 | 100 | 0 | 110 | 0 | 0 | 116 | 0 | 0 | 0 | 150 | 0 | 0 | 0 | 0 | 25 | 0 | 0 | 0 | 621 | 1000 | 2 | 2 |
| 409 | 0 | 100 | 19 | 0 | 0 | 0 | 115 | 0 | 224 | 0 | 0 | 0 | 0 | 25 | 0 | 0 | 0 | 67 | 206 | 1000 | 2 | 2 |
| 410 | 100 | 0 | 384 | 0 | 0 | 0 | 0 | 0 | 0 | 0 | 0 | 79 | 0 | 25 | 0 | 50 | 0 | 67 | 560 | 1000 | 2 | 2 |
| 411 | 0 | 100 | 122 | 44 | 0 | 167 | 0 | 0 | 0 | 0 | 15 | 0 | 10 | 0 | 0 | 50 | 0 | 67 | 485 | 1000 | 2 | 2 |
| 412 | 100 | 0 | 5 | 0 | 0 | 0 | 0 | 0 | 224 | 0 | 154 | 0 | 115 | 0 | 0 | 0 | 50 | 33 | 397 | 1000 | 2 | 2 |
| 413 | 0 | 100 | 179 | 0 | 0 | 104 | 0 | 0 | 0 | 0 | 0 | 0 | 0 | 25 | 25 | 50 | 0 | 67 | 526 | 1000 | 2 | 2 |
| 414 | 100 | 0 | 120 | 0 | 0 | 44 | 0 | 0 | 0 | 0 | 287 | 0 | 0 | 0 | 25 | 0 | 0 | 33 | 434 | 1000 | 2 | 2 |
| 415 | 0 | 100 | 56 | 0 | 56 | 0 | 0 | 0 | 19 | 0 | 0 | 0 | 114 | 25 | 0 | 0 | 50 | 67 | 392 | 1000 | 2 | 2 |
| 416 | 100 | 0 | 140 | 0 | 0 | 0 | 214 | 0 | 0 | 0 | 0 | 0 | 0 | 0 | 25 | 0 | 0 | 0 | 637 | 1000 | 2 | 2 |
| 417 | 100 | 0 | 5 | 0 | 0 | 0 | 103 | 0 | 0 | 0 | 153 | 0 | 0 | 0 | 0 | 50 | 0 | 0 | 628 | 1000 | 2 | 2 |
| 418 | 100 | 0 | 5 | 0 | 0 | 0 | 103 | 0 | 0 | 0 | 0 | 0 | 0 | 0 | 25 | 50 | 0 | 0 | 628 | 1000 | 2 | 2 |
| 419 | 100 | 0 | 11 | 0 | 0 | 0 | 135 | 0 | 0 | 0 | 153 | 0 | 0 | 0 | 25 | 50 | 0 | 0 | 526 | 1000 | 2 | 2 |

-continued

| Expt # (Stock) | 1 MES [0.5M] | 4 HEPES [0.5M] | 1 Sodium Hydroxide [2M] | 1 Sodium Chloride [2M] | 2 Citric Acid [2M] | 3 Acetic Acid [2M] | 4 Ammonium Sulfate [2M] | 5 Monosodium Phosphate [2M] | 1 MPD [30%] | 2 PEG 400 [30%] | 3 PEG 2K [30%] | 4 PEG 4000 [30%] | 5 PEG 6K [30%] | 2 MgCl2 [0.2M] | 3 CaCl2 [0.2M] | 2 Arginine HCl [0.5M] | 3 Beta-OG [0.5M] | 1 Glycerol [75% w/v] | 1 Water | Total | Recipe dispensed | Protein dispensed |
|---|---|---|---|---|---|---|---|---|---|---|---|---|---|---|---|---|---|---|---|---|---|---|
| 420 | 0 | 100 | 88 | 0 | 0 | 0 | 0 | 114 | 0 | 10 | 0 | 0 | 0 | 0 | 0 | 0 | 0 | 33 | 654 | 1000 | 2 | 2 |
| 421 | 0 | 100 | 12 | 73 | 0 | 0 | 0 | 0 | 83 | 0 | 0 | 0 | 0 | 0 | 25 | 0 | 0 | 67 | 589 | 1000 | 2 | 2 |
| 422 | 100 | 0 | 67 | 0 | 30 | 0 | 0 | 0 | 0 | 0 | 0 | 146 | 0 | 0 | 0 | 0 | 50 | 0 | 607 | 1000 | 2 | 2 |
| 423 | 100 | 0 | 78 | 0 | 0 | 71 | 0 | 0 | 0 | 0 | 0 | 78 | 0 | 0 | 25 | 0 | 50 | 0 | 598 | 1000 | 2 | 2 |
| 424 | 0 | 100 | 6 | 153 | 0 | 0 | 0 | 0 | 0 | 0 | 0 | 14 | 0 | 0 | 25 | 50 | 0 | 0 | 642 | 1000 | 2 | 2 |
| 425 | 0 | 100 | 208 | 0 | 72 | 0 | 0 | 0 | 0 | 80 | 0 | 0 | 0 | 0 | 0 | 50 | 0 | 33 | 505 | 1000 | 2 | 2 |
| 426 | 100 | 0 | 9 | 0 | 0 | 0 | 0 | 214 | 0 | 19 | 0 | 0 | 0 | 0 | 0 | 0 | 0 | 0 | 658 | 1000 | 2 | 2 |
| 427 | 0 | 100 | 50 | 0 | 0 | 0 | 0 | 114 | 0 | 10 | 0 | 0 | 0 | 0 | 0 | 50 | 0 | 33 | 643 | 1000 | 2 | 2 |
| 428 | 0 | 100 | 19 | 30 | 0 | 0 | 0 | 0 | 0 | 0 | 0 | 0 | 0 | 0 | 0 | 50 | 50 | 0 | 654 | 1000 | 2 | 2 |
| 429 | 100 | 0 | 5 | 115 | 0 | 0 | 0 | 0 | 0 | 0 | 10 | 0 | 0 | 0 | 25 | 0 | 0 | 67 | 677 | 1000 | 2 | 2 |
| 430 | 0 | 100 | 75 | 0 | 0 | 57 | 0 | 0 | 0 | 0 | 290 | 0 | 0 | 0 | 0 | 50 | 0 | 33 | 394 | 1000 | 2 | 2 |
| 431 | 100 | 0 | 7 | 0 | 0 | 0 | 0 | 0 | 118 | 0 | 0 | 0 | 0 | 0 | 0 | 0 | 0 | 33 | 637 | 1000 | 2 | 2 |
| 432 | 100 | 0 | 18 | 0 | 0 | 0 | 73 | 104 | 0 | 0 | 83 | 0 | 0 | 0 | 25 | 0 | 50 | 67 | 584 | 1000 | 2 | 2 |
| 433 | 100 | 0 | 5 | 0 | 0 | 0 | 104 | 0 | 0 | 115 | 0 | 148 | 0 | 0 | 0 | 50 | 0 | 33 | 592 | 1000 | 2 | 2 |
| 434 | 100 | 0 | 11 | 135 | 114 | 0 | 0 | 0 | 0 | 0 | 10 | 0 | 0 | 25 | 0 | 0 | 0 | 0 | 530 | 1000 | 2 | 2 |
| 435 | 100 | 0 | 272 | 0 | 0 | 0 | 0 | 0 | 0 | 0 | 0 | 0 | 0 | 0 | 0 | 50 | 50 | 33 | 445 | 1000 | 2 | 2 |
| 436 | 100 | 0 | 5 | 0 | 43 | 0 | 43 | 0 | 218 | 0 | 0 | 0 | 0 | 25 | 0 | 0 | 0 | 0 | 559 | 1000 | 2 | 2 |
| 437 | 0 | 100 | 126 | 0 | 0 | 57 | 0 | 0 | 0 | 256 | 219 | 0 | 0 | 0 | 0 | 50 | 0 | 0 | 482 | 1000 | 2 | 2 |
| 438 | 100 | 0 | 54 | 0 | 163 | 0 | 0 | 0 | 0 | 14 | 0 | 0 | 0 | 0 | 25 | 0 | 50 | 67 | 436 | 1000 | 2 | 2 |
| 439 | 0 | 100 | 480 | 0 | 0 | 0 | 214 | 0 | 0 | 0 | 19 | 0 | 0 | 0 | 0 | 50 | 0 | 0 | 208 | 1000 | 2 | 2 |
| 440 | 100 | 0 | 18 | 0 | 0 | 0 | 0 | 0 | 116 | 147 | 0 | 0 | 0 | 25 | 0 | 0 | 50 | 0 | 599 | 1000 | 2 | 2 |
| 441 | 100 | 0 | 5 | 30 | 0 | 0 | 0 | 0 | 0 | 0 | 0 | 0 | 80 | 0 | 25 | 50 | 0 | 0 | 643 | 1000 | 2 | 2 |
| 442 | 100 | 0 | 18 | 103 | 0 | 0 | 72 | 0 | 0 | 0 | 0 | 0 | 0 | 0 | 0 | 50 | 50 | 33 | 588 | 1000 | 2 | 2 |
| 443 | 0 | 100 | 6 | 0 | 0 | 0 | 0 | 0 | 0 | 0 | 117 | 0 | 14 | 0 | 25 | 50 | 0 | 0 | 659 | 1000 | 2 | 2 |
| 444 | 0 | 100 | 19 | 103 | 0 | 165 | 0 | 0 | 0 | 0 | 0 | 0 | 0 | 0 | 0 | 0 | 0 | 33 | 611 | 1000 | 2 | 2 |
| 445 | 100 | 0 | 180 | 0 | 0 | 0 | 0 | 0 | 10 | 0 | 0 | 0 | 14 | 25 | 0 | 0 | 50 | 67 | 507 | 1000 | 2 | 2 |
| 446 | 100 | 0 | 11 | 116 | 163 | 0 | 0 | 0 | 0 | 0 | 0 | 0 | 0 | 0 | 25 | 0 | 0 | 0 | 671 | 1000 | 2 | 2 |
| 447 | 100 | 0 | 435 | 0 | 0 | 0 | 0 | 0 | 0 | 0 | 19 | 0 | 0 | 0 | 0 | 50 | 50 | 67 | 238 | 1000 | 2 | 2 |
| 448 | 0 | 100 | 12 | 214 | 0 | 0 | 0 | 0 | 0 | 0 | 0 | 0 | 0 | 25 | 0 | 0 | 50 | 0 | 579 | 1000 | 2 | 2 |
| 449 | 0 | 100 | 294 | 0 | 103 | 0 | 0 | 0 | 0 | 114 | 0 | 0 | 0 | 0 | 25 | 0 | 0 | 0 | 364 | 1000 | 2 | 2 |
| 450 | 0 | 100 | 6 | 138 | 0 | 0 | 0 | 0 | 0 | 0 | 0 | 151 | 0 | 0 | 0 | 0 | 50 | 67 | 488 | 1000 | 2 | 2 |

We claim:

1. A method for forming dyed protein crystals comprising:
   (a) providing a protein solution, wherein the protein solution contains at least one dye, which dye is capable of dyeing at least a portion of protein crystals formed from the protein solution;
   (b) subjecting the protein solution to environmental conditions effective to form protein crystals; and
   (c) detecting the presence of dyed protein crystals, whereby the presence of the dyed protein crystals indicates the presence of protein crystals.

2. The method of claim 1, wherein the dye is selected from the group consisting of methylene blue, methylene green, Izit and crystal violet.

3. The method of claim 1, wherein the dye binds to protein molecules of the protein crystals formed from the protein solution.

4. The method of claim 1, wherein the dye does not bind to protein molecules of the protein crystals formed from the protein solution and wherein molecules of the dye reside in channels present in the protein crystals.

5. The method of claim 1, wherein the protein solution is partitioned from the atmosphere.

6. The method of claim 5, wherein the protein solution is overlayed with an oil selected from the group consisting of paraffin oil, silicone oil and combinations thereof.

7. The method of claim 1, wherein the protein solution further comprises a component selected from the group consisting of salts, buffers, precipitants, crystallization aids and any combination thereof.

8. The method of claim 7, wherein the component crystallizes under the environmental conditions of (b).

9. The method of claim 8, wherein step (b) comprises addition of a precipitate solution.

10. The method of claim 8, wherein the component crystals are undyed component crystals.

11. The method of claim 8, further comprising detecting crystals formed in the provided protein solution and distinguishing dyed protein crystals from undyed component crystals.

12. The method of claim 11, wherein the protein crystals and the component crystals are detected by microscopy.

13. A method for screening protein crystal growth conditions, comprising:
   (a) providing a set of at least two protein solutions, wherein the protein solutions contain a dye, which dye (i) is capable of dyeing at least a portion of protein crystals formed from the protein solution and (ii) does not dye a significant portion of component crystals formed from the protein solution;
   (b) subjecting the protein solutions to predetermined conditions, wherein the environmental conditions to which each member of the set of protein solutions is subjected is not identical to the environmental conditions to which another member of the set is subjected; and
   (c) detecting the presence or non-presence of dyed protein crystals and/or undyed component crystals, wherein; (i) the presence of the dyed protein crystals indicates the formation of protein crystals; and (ii) the presence of undyed component crystals indicates formation of component crystals.

14. The method of 13, wherein the set of protein solutions consists of greater than 10 protein solutions.

15. The method of 14, wherein the set of protein solutions consists of greater than 100 protein solutions.

16. The method of claim 13, wherein the dye is selected from the group consisting of methylene blue, methylene green, Izit and crystal violet.

17. The method of claim 13, wherein the protein solutions are partitioned from the atmosphere.

18. The method of claim 17, wherein the protein solutions are overlayed with an oil selected from the group consisting of paraffin oil, silicone oil and combinations thereof.

19. The method of claim 13, wherein the protein solution further comprises a component selected from the group consisting of salt, buffer, precipitant, crystallization aid and any combination thereof.

20. The method of claim 13, wherein the component crystallizes under the environmental conditions of (b).

21. The method of claim 20, wherein step (b) comprises addition of a precipitate solution.

22. The method of claim 20, wherein the component crystals comprise undyed component crystals.

23. The method of claim 22, further comprising distinguishing dyed protein crystals from undyed component crystals.

24. The method of claim 23, wherein dyed protein crystals are distinguished from component crystals by use of microscopy.

25. The method of claim 13, wherein detection of dyed protein crystals indicates a combination of conditions to promote crystal growth of a protein in the provided protein solution.

26. The method of claim 25, wherein the detected dyed protein crystals are evaluated in respect to protein crystal quality.

27. The method of claim 26, wherein the evaluation of protein crystal quality includes criterion selected from the group consisting of size of crystals, volume of crystals, intensity of coloration of crystals by dye, color of coloration of crystals by dye, sharpness of crystal edges, crystal shape and combinations thereof.

28. A method for forming dyed component crystals comprising
   (a) providing a component solution, wherein the component solution contains at least one dye, which dye is capable of dyeing at least a portion of component crystals formed from the component solution;
   (b) subjecting the component solution to environmental conditions effective to form component crystals; and
   (c) detecting the presence of dyed component crystals, whereby the presence of the dyed component crystals indicates the presence of component crystals.

29. The method of claim 28, wherein the component solution is partitioned from the atmosphere.

30. The method of claim 29, wherein the component solution is overlayed with an oil selected from the group consisting of paraffin oil, silicone oil and combinations thereof.

31. The method of claim 28, wherein the component solution further comprises a protein.

32. The method of claim 31, wherein the protein crystallizes under the environmental conditions of (b).

33. The method of claim 32, wherein step (b) comprises addition of a precipitate solution.

34. The method of claim 32, wherein the protein crystals comprises undyed protein crystals.

35. The method of claim 32, further comprising detecting any crystals formed in the provided component solution and distinguishing the undyed protein crystals from the dyed component crystals on the basis that the component crystals are dyed component crystals and the protein crystals are undyed protein crystals.

36. The method of claim 35, wherein the protein crystals and the component crystals are detected by microscopy.

37. A method for screening protein crystal growth conditions, comprising:
(a) providing a set of at least two protein solutions, wherein the protein solutions contain a dye, which dye (i) is capable of dyeing at least a portion of component crystal formed from the protein solution and (ii) does not dye a significant portion of protein crystals formed from the protein solution;
(b) subjecting the protein solutions to predetermined conditions, wherein the environmental conditions to which each member of the set of protein solutions is subjected is not identical to the environmental conditions to which another member of the set is subjected; and
(c) detecting the presence or non-presence of undyed protein crystals and/or dyed component crystals, wherein; (i) the presence of undyed protein crystals indicates the formation of protein crystals; and (ii) the presence of dyed component crystals indicates formation of component crystals.

38. The method of 37, wherein the set of protein solutions consists of greater than 10 protein solutions.

39. The method of 38, wherein the set of protein solutions consists of greater than 100 protein solutions.

40. The method of claim 37, wherein the protein solution is partitioned from the atmosphere.

41. The method of claim 40, wherein the protein solution is overlayed with an oil selected from the group consisting of paraffin oil, silicone oil and combinations thereof.

42. The method of claim 37, wherein the protein solution further comprises a component selected from the group consisting of salt, buffer, precipitant, crystallization aid and any combination thereof.

43. The method of claim 37, wherein the protein crystallizes under the environmental conditions of (b).

44. The method of claim 43, wherein step (b) comprises addition of a precipitate solution.

45. The method of claim 43, wherein the protein crystals comprise undyed protein crystals.

46. The method of claim 45, further comprising distinguishing the undyed protein crystals from the dyed component crystals.

47. The method of claim 46, wherein the undyed protein crystal is distinguished from the component crystals by use of microscopy.

48. The method of claim 37, wherein detection of the undyed protein crystals indicates a combination of conditions to promote crystal growth of a protein in the provided protein solutions.

49. The method of claim 48, wherein the detected undyed protein crystals are evaluated in respect to protein crystal quality.

50. The method of claim 49, wherein the evaluation of protein crystal quality includes criterion selected from the group consisting of size of crystals, volume of crystals, intensity of coloration of crystals by dye, color of coloration of crystals by dye, sharpness of crystal edges, crystal shape or combinations thereof.

51. An automated method of screening protein crystal growth conditions comprising the steps of:
a) providing a set of at least two protein solutions, wherein the protein solutions contain a dye, which dye (i) is capable of dyeing at least a portion of protein crystals formed from the protein solution and (ii) does not dye a significant portion of component crystals formed from the protein solution;
b) dispensing the protein solutions onto a platform, wherein the protein solutions are dispensed using an automated dispensing system in accordance with a predetermined program;
c) controlling the protein crystal growth conditions of the protein solutions; and
d) detecting the presence or non-presence of dyed protein crystals and/or undyed component crystals, wherein the presence of the dyed protein crystals indicates the formation of protein crystals; and the presence of undyed component crystals indicates the formation of component crystals.

52. The method according to claim 51 wherein protein solutions on the platform are overlayed with an oil.

53. A method for screening protein crystal growth conditions, comprising:
a) providing a set of at least two protein solutions, wherein the protein solutions contain a dye, which dye (i) is capable of dyeing at least a portion of component crystals formed from the protein solution and (ii) does not dye a significant portion of protein crystals formed from the protein solution;
b) dispensing the protein solutions onto a platform, wherein the protein solutions are dispensed using an automated dispensing system in accordance with a predetermined program;
c) controlling the protein crystal growth conditions of the protein solutions; and
d) detecting the presence or non-presence of undyed protein crystals and/or dyed component crystals, wherein the presence of the undyed protein crystals indicates the formation of protein crystals; and the presence of the dyed component crystals indicates formation of component crystals.

54. The method according to claim 53 wherein the protein solutions on the platform are overlayed with an oil.

55. The method of claim 31, wherein the component solution is partitioned from the atmosphere.

* * * * *